US012740791B2

(12) United States Patent
DiGeorgio et al.

(10) Patent No.: US 12,740,791 B2
(45) Date of Patent: Sep. 22, 2026

(54) DEVICES AND LESS INVASIVE TECHNIQUES FOR TREATING LESSER METATARSALS OF THE FOOT

(71) Applicant: Treace Medical Concepts, Inc., Ponte Vedra, FL (US)

(72) Inventors: Caitlin DiGeorgio, Ponte Vedra, FL (US); Sean F. Scanlan, Jacksonville, FL (US); Jason May, St. John's, FL (US); Jody McAleer, Jefferson City, MO (US); Jonathan M. Dewey, Ponte Vedra, FL (US); Adam Hausman, Jacksonville, FL (US); Steve Norton, Jacksonville, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 65 days.

(21) Appl. No.: 18/801,171

(22) Filed: Aug. 12, 2024

(65) Prior Publication Data

US 2025/0049449 A1 Feb. 13, 2025

Related U.S. Application Data

(60) Provisional application No. 63/519,180, filed on Aug. 11, 2023.

(51) Int. Cl.
*A61B 17/17* (2006.01)

(52) U.S. Cl.
CPC ................................ *A61B 17/1775* (2016.11)

(58) Field of Classification Search
CPC ........................ A61B 17/1775; A61B 17/1682
See application file for complete search history.

(56) References Cited

U.S. PATENT DOCUMENTS

| | | | |
|---|---|---|---|
| 2,251,209 | A | 7/1941 | Stader |
| 2,432,695 | A | 12/1947 | Speas |

(Continued)

FOREIGN PATENT DOCUMENTS

| | | | |
|---|---|---|---|
| AU | 2009227957 | B2 | 7/2014 |
| CA | 2491824 | A1 | 9/2005 |

(Continued)

OTHER PUBLICATIONS

"Arthrodesis of the Tarsometatarsal Joint," Retrieved from https://musculoskeletalkey.com/arthrodesis-of-the-tarsometatarsal-joint/, posted Apr. 18, 2019, 11 pages.

(Continued)

*Primary Examiner* — Andrew Yang
(74) *Attorney, Agent, or Firm* — Fredrikson & Byron, P.A.

(57) ABSTRACT

A variety of surgical procedures may be performed on the bones of the foot, such as on one or more lesser metatarsals of the foot positioned laterally of the first metatarsal. For example, a surgical procedure may involve cutting an end of one or both of a second metatarsal and an intermediate cuneiform and/or cutting an end of one or both of a third metatarsal and a lateral cuneiform. The tarsometatarsal joints defined be one or both sets of bones may be cut to treat an arthritic joint, metatarsus adductus, and/or other clinical condition. In any case, various surgical instruments can be utilized during a procedure to help increase the accuracy and repeatability of the procedure patient-to-patient, improving overall patient outcomes and making it less invasive. For example, one or more cut guides having tissue control features may be utilized during procedure.

17 Claims, 21 Drawing Sheets

(56) References Cited

U.S. PATENT DOCUMENTS

| | | | |
|---|---|---|---|
| 3,664,022 | A | 5/1972 | Small |
| 4,069,824 | A | 1/1978 | Weinstock |
| 4,159,716 | A | 7/1979 | Borchers |
| 4,187,840 | A | 2/1980 | Watanabe |
| 4,187,841 | A | 2/1980 | Knutson |
| 4,335,715 | A | 6/1982 | Kirkley |
| 4,338,927 | A | 7/1982 | Volkov et al. |
| 4,349,018 | A | 9/1982 | Chambers |
| 4,409,973 | A | 10/1983 | Neufeld |
| 4,440,168 | A | 4/1984 | Warren |
| 4,501,268 | A | 2/1985 | Comparetto |
| 4,502,474 | A | 3/1985 | Comparetto |
| 4,509,511 | A | 4/1985 | Neufeld |
| 4,565,191 | A | 1/1986 | Slocum |
| 4,570,624 | A | 2/1986 | Wu |
| 4,627,425 | A | 12/1986 | Reese |
| 4,628,919 | A | 12/1986 | Clyburn |
| 4,632,102 | A | 12/1986 | Comparetto |
| 4,664,102 | A | 5/1987 | Comparetto |
| 4,708,133 | A | 11/1987 | Comparetto |
| 4,730,608 | A | 3/1988 | Schlein |
| 4,736,737 | A | 4/1988 | Fargie et al. |
| 4,750,481 | A | 6/1988 | Reese |
| 4,754,746 | A | 7/1988 | Cox |
| 4,757,810 | A | 7/1988 | Reese |
| 4,895,141 | A | 1/1990 | Koeneman et al. |
| 4,952,214 | A | 8/1990 | Comparetto |
| 4,959,066 | A | 9/1990 | Dunn et al. |
| 4,978,347 | A | 12/1990 | Ilizarov |
| 4,988,349 | A | 1/1991 | Pennig |
| 4,995,875 | A | 2/1991 | Coes |
| 5,021,056 | A | 6/1991 | Hofmann et al. |
| 5,035,698 | A | 7/1991 | Comparetto |
| 5,042,983 | A | 8/1991 | Rayhack |
| 5,049,149 | A | 9/1991 | Schmidt |
| 5,053,039 | A | 10/1991 | Hofmann et al. |
| 5,078,719 | A | 1/1992 | Schreiber |
| 5,112,334 | A | 5/1992 | Alchermes et al. |
| 5,147,364 | A | 9/1992 | Comparetto |
| 5,176,685 | A | 1/1993 | Rayhack |
| 5,207,676 | A | 5/1993 | Canadell et al. |
| 5,246,444 | A | 9/1993 | Schreiber |
| 5,254,119 | A | 10/1993 | Schreiber |
| 5,304,177 | A | 4/1994 | Pennig |
| 5,312,412 | A | 5/1994 | Whipple |
| 5,358,504 | A | 10/1994 | Paley et al. |
| 5,364,402 | A | 11/1994 | Mumme et al. |
| 5,374,271 | A | 12/1994 | Hwang |
| 5,413,579 | A | 5/1995 | Tom Du Toit |
| 5,415,663 | A | 5/1995 | Luckman et al. |
| 5,417,694 | A | 5/1995 | Marik et al. |
| 5,449,360 | A | 9/1995 | Schreiber |
| 5,470,335 | A | 11/1995 | Du Toit |
| 5,490,854 | A | 2/1996 | Fisher et al. |
| 5,529,075 | A | 6/1996 | Clark |
| 5,540,695 | A | 7/1996 | Levy |
| 5,578,038 | A | 11/1996 | Slocum |
| 5,586,564 | A | 12/1996 | Barrett et al. |
| 5,601,565 | A | 2/1997 | Huebner |
| 5,611,802 | A | 3/1997 | Samuelson et al. |
| 5,613,969 | A | 3/1997 | Jenkins, Jr. |
| 5,620,442 | A | 4/1997 | Bailey et al. |
| 5,620,448 | A | 4/1997 | Puddu |
| D380,548 | S | 7/1997 | Koros et al. |
| 5,643,270 | A | 7/1997 | Combs |
| 5,667,510 | A | 9/1997 | Combs |
| H1706 | H | 1/1998 | Mason |
| 5,722,978 | A | 3/1998 | Jenkins, Jr. |
| 5,749,875 | A | 5/1998 | Puddu |
| 5,779,709 | A | 7/1998 | Harris, Jr. et al. |
| 5,788,695 | A | 8/1998 | Richardson |
| 5,792,159 | A | 8/1998 | Amin |
| 5,803,924 | A | 9/1998 | Oni et al. |
| 5,810,822 | A | 9/1998 | Mortier |
| D403,066 | S | 12/1998 | Defonzo |
| 5,843,085 | A | 12/1998 | Graser |
| 5,893,553 | A | 4/1999 | Pinkous |
| 5,911,724 | A | 6/1999 | Wehrli |
| 5,935,128 | A | 8/1999 | Carter et al. |
| 5,941,877 | A | 8/1999 | Viegas et al. |
| 5,951,556 | A | 9/1999 | Faccioli et al. |
| D417,276 | S | 11/1999 | Defonzo |
| 5,980,526 | A | 11/1999 | Johnson et al. |
| 5,984,931 | A | 11/1999 | Greenfield |
| 6,007,535 | A | 12/1999 | Rayhack et al. |
| 6,027,504 | A | 2/2000 | Mcguire |
| 6,030,391 | A | 2/2000 | Brainard et al. |
| 6,162,223 | A | 12/2000 | Orsak et al. |
| 6,171,309 | B1 | 1/2001 | Huebner |
| 6,203,545 | B1 | 3/2001 | Stoffella |
| D443,059 | S | 5/2001 | Endo |
| 6,248,109 | B1 | 6/2001 | Stoffella |
| 6,391,031 | B1 | 5/2002 | Toomey |
| 6,416,465 | B2 | 7/2002 | Brau |
| 6,478,799 | B1 | 11/2002 | Williamson |
| 6,511,481 | B2 | 1/2003 | Von Hoffmann et al. |
| 6,547,793 | B1 | 4/2003 | Mcguire |
| 6,676,662 | B1 | 1/2004 | Bagga et al. |
| 6,719,773 | B1 | 4/2004 | Boucher et al. |
| 6,743,233 | B1 | 6/2004 | Baldwin et al. |
| 6,755,838 | B2 | 6/2004 | Trnka |
| 6,796,986 | B2 | 9/2004 | Duffner |
| 6,859,661 | B2 | 2/2005 | Tuke |
| 6,964,645 | B1 | 11/2005 | Smits |
| 7,018,383 | B2 | 3/2006 | Mcguire |
| 7,033,361 | B2 | 4/2006 | Collazo |
| 7,097,647 | B2 | 8/2006 | Segler |
| 7,112,204 | B2 | 9/2006 | Justin et al. |
| 7,153,310 | B2 | 12/2006 | Ralph et al. |
| 7,182,766 | B1 | 2/2007 | Mogul |
| 7,241,298 | B2 | 7/2007 | Nemec et al. |
| 7,282,054 | B2 | 10/2007 | Steffensmeier et al. |
| D566,271 | S | 4/2008 | Gao et al. |
| 7,377,924 | B2 | 5/2008 | Raistrick et al. |
| 7,465,303 | B2 | 12/2008 | Riccione et al. |
| 7,540,874 | B2 | 6/2009 | Trumble et al. |
| D597,666 | S | 8/2009 | George et al. |
| 7,572,258 | B2 | 8/2009 | Stiernborg |
| 7,578,822 | B2 | 8/2009 | Rezach et al. |
| 7,618,424 | B2 | 11/2009 | Wilcox et al. |
| 7,641,660 | B2 | 1/2010 | Lakin et al. |
| D610,257 | S | 2/2010 | Horton |
| 7,686,811 | B2 | 3/2010 | Byrd et al. |
| 7,691,108 | B2 | 4/2010 | Lavallee |
| 7,763,026 | B2 | 7/2010 | Egger et al. |
| D629,900 | S | 12/2010 | Fisher |
| 7,967,823 | B2 | 6/2011 | Ammann et al. |
| 7,972,338 | B2 | 7/2011 | O'Brien |
| D646,389 | S | 10/2011 | Claypool et al. |
| 8,057,478 | B2 | 11/2011 | Kuczynski et al. |
| 8,062,301 | B2 | 11/2011 | Ammann et al. |
| D651,315 | S | 12/2011 | Bertoni et al. |
| D651,316 | S | 12/2011 | May et al. |
| 8,080,010 | B2 | 12/2011 | Schulz et al. |
| 8,080,045 | B2 | 12/2011 | Wotton, III |
| 8,083,746 | B2 | 12/2011 | Novak |
| 8,123,753 | B2 | 2/2012 | Poncet |
| D656,610 | S | 3/2012 | Kleiner |
| 8,137,406 | B2 | 3/2012 | Novak et al. |
| 8,147,530 | B2 | 4/2012 | Strnad et al. |
| 8,167,918 | B2 | 5/2012 | Strnad et al. |
| 8,172,848 | B2 | 5/2012 | Tomko et al. |
| 8,192,441 | B2 | 6/2012 | Collazo |
| 8,197,487 | B2 | 6/2012 | Poncet et al. |
| 8,231,623 | B1 | 7/2012 | Jordan |
| 8,231,663 | B2 | 7/2012 | Kay et al. |
| 8,236,000 | B2 | 8/2012 | Ammann et al. |
| 8,246,561 | B1 | 8/2012 | Agee et al. |
| D666,721 | S | 9/2012 | Wright et al. |
| 8,262,664 | B2 | 9/2012 | Justin et al. |
| 8,277,459 | B2 | 10/2012 | Sand et al. |
| 8,282,644 | B2 | 10/2012 | Edwards |
| 8,282,645 | B2 | 10/2012 | Lawrence et al. |
| 8,292,966 | B2 | 10/2012 | Morton |

(56) References Cited

U.S. PATENT DOCUMENTS 8,303,596 B2 11/2012 Plaky et al.
8,313,492 B2 11/2012 Wong et al.
8,323,289 B2 12/2012 Re
8,337,503 B2 12/2012 Lian
8,343,159 B2 1/2013 Bennett
8,377,105 B2 2/2013 Bscher
D679,395 S 4/2013 Wright et al.
8,409,209 B2 4/2013 Ammann et al.
8,435,246 B2 5/2013 Fisher et al.
8,475,462 B2 7/2013 Thomas et al.
8,496,662 B2 7/2013 Novak et al.
8,518,045 B2 8/2013 Szanto
8,523,870 B2 9/2013 Green, II et al.
8,529,571 B2 9/2013 Horan et al.
8,540,777 B2 9/2013 Ammann et al.
8,545,508 B2 10/2013 Collazo
D694,884 S 12/2013 Mooradian et al.
D695,402 S 12/2013 Dacosta et al.
8,652,142 B2 2/2014 Geissler
8,657,820 B2 2/2014 Kubiak et al.
D701,303 S 3/2014 Cook
8,672,945 B2 3/2014 Lavallee et al.
8,696,716 B2 4/2014 Kartalian et al.
8,702,715 B2 4/2014 Ammann et al.
D705,929 S 5/2014 Frey
8,715,363 B2 5/2014 Ratron et al.
8,728,084 B2 5/2014 Berelsman et al.
8,758,354 B2 6/2014 Habegger et al.
8,764,760 B2 7/2014 Metzger et al.
8,764,763 B2 7/2014 Wong et al.
8,771,279 B2 7/2014 Philippon et al.
8,777,948 B2 7/2014 Bernsteiner
8,784,427 B2 7/2014 Fallin et al.
8,784,457 B2 7/2014 Graham
8,795,286 B2 8/2014 Sand et al.
8,801,727 B2 8/2014 Chan et al.
8,808,303 B2 8/2014 Stemniski et al.
8,828,012 B2 9/2014 May et al.
8,858,602 B2 10/2014 Weiner et al.
8,882,778 B2 11/2014 Ranft
8,882,816 B2 11/2014 Kartalian et al.
8,888,785 B2 11/2014 Ammann et al.
D720,456 S 12/2014 Dacosta et al.
8,900,247 B2 12/2014 Tseng et al.
8,906,026 B2 12/2014 Ammann et al.
8,945,132 B2 2/2015 Play et al.
8,998,903 B2 4/2015 Price et al.
8,998,904 B2 4/2015 Zeetser et al.
9,023,052 B2 5/2015 Lietz et al.
9,044,250 B2 6/2015 Olsen et al.
9,060,822 B2 6/2015 Wright et al.
9,078,710 B2 7/2015 Thoren et al.
9,089,376 B2 7/2015 Medoff et al.
9,101,421 B2 8/2015 Blacklidge
9,107,715 B2 8/2015 Blitz et al.
9,113,920 B2 8/2015 Ammann et al.
D740,424 S 10/2015 Dacosta et al.
D747,479 S 1/2016 Knight
D765,844 S 9/2016 Dacosta
D766,434 S 9/2016 Dacosta
D766,437 S 9/2016 Dacosta
D766,438 S 9/2016 Dacosta
D766,439 S 9/2016 Dacosta
9,452,057 B2 9/2016 Dacosta et al.
9,522,023 B2 12/2016 Haddad et al.
9,592,084 B2 3/2017 Grant
9,622,805 B2 4/2017 Santrock et al.
D796,671 S 9/2017 Khouri
9,750,538 B2 9/2017 Soffiatti et al.
9,770,272 B2 9/2017 Thoren et al.
9,785,747 B2 10/2017 Geebelen
9,924,969 B2 3/2018 Triplett et al.
9,936,994 B2 4/2018 Smith et al.
9,980,760 B2 5/2018 Dacosta et al.
10,028,750 B2 7/2018 Rose
10,064,631 B2 9/2018 Dacosta et al.
10,159,499 B2 12/2018 Dacosta et al.
10,292,713 B2 5/2019 Fallin et al.
10,327,829 B2 6/2019 Dacosta et al.
10,376,268 B2 8/2019 Fallin et al.
D865,173 S 10/2019 Hartson et al.
10,470,779 B2 11/2019 Fallin et al.
10,524,808 B1 1/2020 Hissong et al.
10,779,867 B2 9/2020 Penzimer et al.
D904,609 S 12/2020 Dacosta et al.
10,939,939 B1 3/2021 Gil et al.
D915,588 S 4/2021 Dacosta et al.
D931,449 S 9/2021 Tanabe
D943,741 S 2/2022 Hartson et al.
D945,610 S 3/2022 Wilson et al.
11,304,705 B2 4/2022 Fallin et al.
D956,227 S 6/2022 Dacosta et al.
2002/0099381 A1 7/2002 Maroney
2002/0107519 A1 8/2002 Dixon et al.
2002/0165552 A1 11/2002 Duffner
2002/0198531 A1 12/2002 Millard et al.
2004/0010259 A1 1/2004 Keller et al.
2004/0039394 A1 2/2004 Conti et al.
2004/0097946 A1 5/2004 Dietzel et al.
2004/0138669 A1 7/2004 Horn
2005/0004676 A1 1/2005 Schon et al.
2005/0021040 A1 1/2005 Bertagnoli
2005/0059978 A1 3/2005 Sherry et al.
2005/0070909 A1 3/2005 Egger et al.
2005/0075641 A1 4/2005 Singhatat et al.
2005/0101961 A1 5/2005 Huebner et al.
2005/0149042 A1 7/2005 Metzger
2005/0203509 A1 9/2005 Chinnaian et al.
2005/0228389 A1 10/2005 Stiernborg
2005/0251147 A1 11/2005 Novak
2005/0267482 A1 12/2005 Hyde
2005/0273112 A1 12/2005 Mcnamara
2006/0122597 A1 6/2006 Jones et al.
2006/0129163 A1 6/2006 Mcguire
2006/0206044 A1 9/2006 Simon
2006/0217733 A1 9/2006 Plassky et al.
2006/0229604 A1 10/2006 Olsen et al.
2006/0229621 A1 10/2006 Cadmus
2006/0235383 A1 10/2006 Hollawell
2006/0241607 A1 10/2006 Myerson et al.
2006/0241608 A1 10/2006 Myerson et al.
2006/0247649 A1 11/2006 Rezach et al.
2006/0264961 A1 11/2006 Murray-Brown
2007/0010818 A1 1/2007 Stone et al.
2007/0055233 A1 3/2007 Brinker
2007/0123857 A1 5/2007 Deffenbaugh et al.
2007/0233138 A1 10/2007 Figueroa et al.
2007/0265634 A1 11/2007 Weinstein
2007/0276383 A1 11/2007 Rayhack
2008/0009863 A1 1/2008 Bond et al.
2008/0015603 A1 1/2008 Collazo
2008/0039850 A1 2/2008 Rowley et al.
2008/0091197 A1 4/2008 Coughlin
2008/0140081 A1 6/2008 Heavener et al.
2008/0147073 A1 6/2008 Ammann et al.
2008/0172054 A1 7/2008 Claypool et al.
2008/0195215 A1 8/2008 Morton
2008/0208252 A1 8/2008 Holmes
2008/0262500 A1 10/2008 Collazo
2008/0269908 A1 10/2008 Warburton
2008/0288004 A1 11/2008 Schendel
2009/0036893 A1 2/2009 Kartalian et al.
2009/0036931 A1 2/2009 Pech et al.
2009/0054899 A1 2/2009 Ammann et al.
2009/0093849 A1 4/2009 Grabowski
2009/0105767 A1 4/2009 Reiley
2009/0118733 A1 5/2009 Orsak et al.
2009/0187189 A1 7/2009 Mirza et al.
2009/0198244 A1 8/2009 Leibel
2009/0198279 A1 8/2009 Zhang et al.
2009/0216089 A1 8/2009 Davidson
2009/0222047 A1 9/2009 Graham
2009/0254092 A1 10/2009 Albiol Llorach
2009/0254126 A1 10/2009 Orbay et al.

(56) References Cited

U.S. PATENT DOCUMENTS

2009/0287309 A1 11/2009 Walch et al.
2010/0030283 A1 2/2010 King et al.
2010/0069910 A1 3/2010 Hasselman
2010/0121334 A1 5/2010 Couture et al.
2010/0130981 A1 5/2010 Richards
2010/0152782 A1 6/2010 Stone et al.
2010/0168799 A1 7/2010 Schumer
2010/0185245 A1 7/2010 Paul et al.
2010/0249779 A1 9/2010 Hotchkiss et al.
2010/0256687 A1 10/2010 Neufeld et al.
2010/0318088 A1 12/2010 Warne et al.
2010/0324556 A1 12/2010 Tyber et al.
2011/0009865 A1 1/2011 Orfaly
2011/0093084 A1 4/2011 Morton
2011/0118739 A1 5/2011 Tyber et al.
2011/0172662 A1 7/2011 Keilen
2011/0178524 A1 7/2011 Lawrence et al.
2011/0245835 A1 10/2011 Dodds et al.
2011/0288550 A1 11/2011 Orbay et al.
2011/0301648 A1 12/2011 Lofthouse et al.
2012/0016426 A1 1/2012 Robinson
2012/0065689 A1 3/2012 Prasad et al.
2012/0078258 A1 3/2012 Lo et al.
2012/0123420 A1 5/2012 Honiball
2012/0123484 A1 5/2012 Lietz et al.
2012/0130376 A1 5/2012 Loring et al.
2012/0130382 A1 5/2012 Iannotti et al.
2012/0130383 A1 5/2012 Budoff
2012/0184961 A1 7/2012 Johannaber
2012/0185056 A1 7/2012 Warburton
2012/0191199 A1 7/2012 Raemisch
2012/0239045 A1 9/2012 Li
2012/0253350 A1 10/2012 Anthony et al.
2012/0265301 A1 10/2012 Demers et al.
2012/0277745 A1 11/2012 Lizee
2012/0303033 A1 11/2012 Weiner et al.
2012/0330135 A1 12/2012 Millahn et al.
2013/0012949 A1 1/2013 Fallin et al.
2013/0035694 A1 2/2013 Grimm et al.
2013/0085499 A1 4/2013 Lian
2013/0085502 A1 4/2013 Harrold
2013/0096563 A1 4/2013 Meade et al.
2013/0131821 A1 5/2013 Cachia
2013/0150900 A1 6/2013 Haddad et al.
2013/0150903 A1 6/2013 Vincent
2013/0158556 A1 6/2013 Jones et al.
2013/0165936 A1 6/2013 Myers
2013/0165938 A1 6/2013 Chow et al.
2013/0172942 A1 7/2013 Wright et al.
2013/0184714 A1 7/2013 Kaneyama et al.
2013/0190765 A1 7/2013 Harris et al.
2013/0190766 A1 7/2013 Harris et al.
2013/0204259 A1 8/2013 Zajac
2013/0226248 A1 8/2013 Hatch et al.
2013/0226252 A1 8/2013 Mayer
2013/0231668 A1 9/2013 Olsen et al.
2013/0237987 A1 9/2013 Graham
2013/0237989 A1 9/2013 Bonutti
2013/0267956 A1 10/2013 Terrill et al.
2013/0310836 A1 11/2013 Raub et al.
2013/0325019 A1 12/2013 Thomas et al.
2013/0325076 A1 12/2013 Palmer et al.
2013/0331845 A1 12/2013 Horan et al.
2013/0338785 A1 12/2013 Wong
2014/0005672 A1 1/2014 Edwards et al.
2014/0025127 A1 1/2014 Richter
2014/0039501 A1 2/2014 Schickendantz et al.
2014/0039561 A1 2/2014 Weiner et al.
2014/0046387 A1 2/2014 Waizenegger
2014/0074099 A1 3/2014 Vigneron et al.
2014/0074101 A1 3/2014 Collazo
2014/0094861 A1 4/2014 Fallin
2014/0094924 A1 4/2014 Hacking et al.
2014/0135775 A1 5/2014 Maxson et al.
2014/0163563 A1 6/2014 Reynolds et al.
2014/0171953 A1 6/2014 Gonzalvez et al.
2014/0180342 A1 6/2014 Lowery et al.
2014/0188139 A1 7/2014 Fallin et al.
2014/0194884 A1 7/2014 Martin et al.
2014/0194999 A1 7/2014 Orbay et al.
2014/0207144 A1 7/2014 Lee et al.
2014/0228899 A1 8/2014 Thoren et al.
2014/0243825 A1 8/2014 Yapp et al.
2014/0249537 A1 9/2014 Wong et al.
2014/0257308 A1 9/2014 Johannaber
2014/0257509 A1 9/2014 Dacosta et al.
2014/0276815 A1 9/2014 Riccione
2014/0276853 A1 9/2014 Long et al.
2014/0277176 A1 9/2014 Buchanan et al.
2014/0277214 A1 9/2014 Helenbolt et al.
2014/0288562 A1 9/2014 Von Zabern et al.
2014/0296995 A1 10/2014 Reiley et al.
2014/0303621 A1 10/2014 Gerold et al.
2014/0336658 A1 11/2014 Luna et al.
2014/0343555 A1 11/2014 Russi et al.
2014/0350561 A1 11/2014 Dacosta et al.
2015/0032168 A1 1/2015 Orsak et al.
2015/0045801 A1 2/2015 Axelson, Jr. et al.
2015/0045839 A1 2/2015 Dacosta et al.
2015/0051650 A1 2/2015 Verstreken et al.
2015/0057667 A1 2/2015 Ammann et al.
2015/0066088 A1 3/2015 Brinkman et al.
2015/0066094 A1 3/2015 Anderson et al.
2015/0112446 A1 4/2015 Melamed et al.
2015/0119944 A1 4/2015 Geldwert
2015/0142064 A1 5/2015 Perez et al.
2015/0150608 A1 6/2015 Sammarco
2015/0182273 A1 7/2015 Stemniski et al.
2015/0223851 A1 8/2015 Hill et al.
2015/0230843 A1 8/2015 Palmer et al.
2015/0245858 A1 9/2015 Weiner et al.
2016/0015426 A1 1/2016 Dayton
2016/0022315 A1 1/2016 Soffiatti et al.
2016/0135858 A1 5/2016 Dacosta et al.
2016/0151165 A1 6/2016 Fallin et al.
2016/0175089 A1 6/2016 Fallin et al.
2016/0192950 A1 7/2016 Dayton et al.
2016/0192970 A1 7/2016 Dayton et al.
2016/0199076 A1 7/2016 Fallin et al.
2016/0213384 A1 7/2016 Fallin et al.
2016/0235414 A1 8/2016 Hatch et al.
2016/0242791 A1 8/2016 Fallin et al.
2016/0256204 A1 9/2016 Patel et al.
2016/0270800 A1 9/2016 Sanders
2016/0324532 A1 11/2016 Montoya et al.
2016/0354127 A1 12/2016 Lundquist et al.
2017/0014143 A1 1/2017 Dayton et al.
2017/0042598 A1 2/2017 Santrock et al.
2017/0042599 A1 2/2017 Bays et al.
2017/0079669 A1 3/2017 Bays et al.
2017/0135706 A1 5/2017 Frey et al.
2017/0143511 A1 5/2017 Cachia
2017/0164989 A1 6/2017 Weiner et al.
2017/0290614 A1 10/2017 Weiner et al.
2018/0021145 A1 1/2018 Seavey et al.
2018/0132868 A1 5/2018 Dacosta et al.
2018/0235765 A1 8/2018 Welker et al.
2018/0344334 A1 12/2018 Kim et al.
2019/0099189 A1 4/2019 Fallin et al.
2019/0336140 A1 11/2019 Dacosta et al.
2019/0350598 A1 11/2019 Jacobson
2020/0015856 A1 1/2020 Treace et al.
2020/0060721 A1 2/2020 Cermak
2020/0253641 A1 8/2020 Treace et al.
2021/0236180 A1 8/2021 Decarbo et al.
2021/0244443 A1 8/2021 Coyne et al.
2021/0361330 A1 11/2021 Mcaleer et al.
2022/0117611 A1 4/2022 Milella, Jr. et al.
2022/0211387 A1 7/2022 Perler et al.
2022/0257267 A1 8/2022 Decarbo et al.
2022/0323085 A1 10/2022 Hales et al.
2022/0370082 A1 11/2022 Kuyler et al.

(56) References Cited

U.S. PATENT DOCUMENTS

| | | | |
|---|---|---|---|
| 2023/0043129 | A1 | 2/2023 | Mcaleer et al. |
| 2023/0263536 | A1 | 8/2023 | Kuyler et al. |

FOREIGN PATENT DOCUMENTS

| | | | |
|---|---|---|---|
| CA | 2854997 | A1 | 5/2013 |
| CH | 695846 | A5 | 9/2006 |
| CN | 2930668 | Y | 8/2007 |
| CN | 201558162 | U | 8/2010 |
| CN | 201572172 | U | 9/2010 |
| CN | 201586060 | U | 9/2010 |
| CN | 201912210 | U | 8/2011 |
| CN | 101237835 | B | 11/2012 |
| CN | 202801773 | U | 3/2013 |
| CN | 103462675 | A | 12/2013 |
| CN | 103505276 | A | 1/2014 |
| CN | 203458450 | U | 3/2014 |
| CN | 102860860 | B | 5/2014 |
| CN | 203576647 | U | 5/2014 |
| CN | 104490460 | A | 4/2015 |
| CN | 104510523 | A | 4/2015 |
| CN | 104523327 | A | 4/2015 |
| CN | 104546102 | A | 4/2015 |
| CN | 204379413 | U | 6/2015 |
| CN | 204410951 | U | 6/2015 |
| CN | 204428143 | U | 7/2015 |
| CN | 204428144 | U | 7/2015 |
| CN | 204428145 | U | 7/2015 |
| CN | 204446081 | U | 7/2015 |
| DE | 202006010241 | U1 | 3/2007 |
| DE | 102007053058 | B3 | 4/2009 |
| EP | 685206 | B1 | 9/2000 |
| EP | 1508316 | B1 | 5/2007 |
| EP | 1897509 | B1 | 7/2009 |
| EP | 2124772 | A1 | 12/2009 |
| EP | 2124832 | B1 | 8/2012 |
| EP | 2632349 | A1 | 9/2013 |
| EP | 2665428 | A1 | 11/2013 |
| EP | 2742878 | A1 | 6/2014 |
| EP | 2750617 | A1 | 7/2014 |
| EP | 2849684 | A1 | 3/2015 |
| EP | 2932925 | A1 | 10/2015 |
| EP | 2624764 | B1 | 12/2015 |
| EP | 3023068 | A2 | 5/2016 |
| FR | 2362616 | A1 | 3/1978 |
| FR | 2764183 | B1 | 11/1999 |
| FR | 2953120 | B1 | 1/2012 |
| FR | 3030221 | A1 | 6/2016 |
| GB | 2154143 | A | 9/1985 |
| GB | 2154144 | A | 9/1985 |
| GB | 2334214 | B | 1/2003 |
| IN | 200903719 | P1 | 4/2010 |
| IN | 200904479 | P2 | 5/2010 |
| IN | 2004/KOLNP/2013 | | 1/2013 |
| IN | 140/DELNP/2012 | | 2/2013 |
| JP | 63005739 | A | 1/1988 |
| JP | 2004174265 | A | 6/2004 |
| JP | 2006158972 | A | 6/2006 |
| JP | 4134243 | B2 | 8/2008 |
| JP | 4162380 | B2 | 10/2008 |
| JP | 2011092405 | A | 5/2011 |
| JP | 2011523889 | A | 8/2011 |
| JP | 4796943 | B2 | 10/2011 |
| JP | 5466647 | B2 | 4/2014 |
| JP | 2014511207 | A | 5/2014 |
| JP | 2014521384 | A | 8/2014 |
| JP | 5628875 | B2 | 11/2014 |
| KR | 100904142 | B1 | 6/2009 |
| MD | 756 | B1 | 7/1997 |
| RU | 2098036 | C1 | 12/1997 |
| RU | 2195892 | C2 | 1/2003 |
| RU | 2320287 | C1 | 3/2008 |
| RU | 2321366 | C2 | 4/2008 |
| RU | 2321369 | C1 | 4/2008 |
| RU | 2346663 | C2 | 2/2009 |
| RU | 2412662 | C1 | 2/2011 |
| SU | 1333328 | A2 | 8/1987 |
| WO | 0166022 | A1 | 9/2001 |
| WO | 03075775 | A1 | 9/2003 |
| WO | 2004089227 | A2 | 10/2004 |
| WO | 2005009209 | A2 | 2/2005 |
| WO | 2005122923 | A1 | 12/2005 |
| WO | 2008051064 | A1 | 5/2008 |
| WO | 2009029798 | A1 | 3/2009 |
| WO | 2009032101 | A2 | 3/2009 |
| WO | 2011037885 | A1 | 3/2011 |
| WO | 2012029008 | A1 | 3/2012 |
| WO | 2013090392 | A1 | 6/2013 |
| WO | 2013134387 | A1 | 9/2013 |
| WO | 2013169475 | A1 | 11/2013 |
| WO | 2014020561 | A1 | 2/2014 |
| WO | 2014022055 | A1 | 2/2014 |
| WO | 2014035991 | A1 | 3/2014 |
| WO | 2014085882 | A1 | 6/2014 |
| WO | 2014147099 | A1 | 9/2014 |
| WO | 2014152219 | A2 | 9/2014 |
| WO | 2014152535 | A1 | 9/2014 |
| WO | 2014177783 | A1 | 11/2014 |
| WO | 2014200017 | A1 | 12/2014 |
| WO | 2015094409 | A1 | 6/2015 |
| WO | 2015105880 | A1 | 7/2015 |
| WO | 2015127515 | A2 | 9/2015 |
| WO | 2016134160 | A1 | 8/2016 |
| WO | 2017134486 | A1 | 8/2017 |

OTHER PUBLICATIONS

Accu-Cut Osteotomy Guide System, BioPro, Brochure, Oct. 2018, 2 pages.

"Acumed Osteotomiesystem Operationstechnik", Acumed, 2014, 19 pages (including 3 pages English translation).

Aiyer et al., "Prevalence of Metatarsus Adductus in Patients Undergoing Hallux Valgus Surgery," Foot & Ankle International, vol. 35, No. 12, 2014, pp. 1292-1297.

Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.

Alvine et al., "Peg and Dowel Fusion of the Proximal Interphalangeal Joint," Foot & Ankle, vol. 1, No. 2, 1980, pp. 90-94.

Anderson et al., "Uncemented STAR Total Ankle Prostheses," The Journal of Bone and Joint Surgery, vol. 86(1, Suppl 2), Sep. 2004, pp. 103-111, (Abstract Only).

Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.

Baravarian, "Why the Lapidus Procedure is Ideal for Bunions," Podiatry Today, Retrieved online from <https://www.hmpglobal-learhmpgloballe.com/site/podipodi/article/5542>, dated May 2006, 8 pages.

Bauer et al., "Offset-V Osteotomy of the First Metatarsal Shaft in Hallux Abducto Valgus," McGlamrys Comprehensive Textbook of Foot and Ankle Surgery, Fourth Edition, vol. 1, Chapter 29, 2013, 26 pages.

Bednarz et al., "Modified Lapidus Procedure for the Treatment of Hypermobile Hallux Valgus," Foot & Ankle International, vol. 21, No. 10, Oct. 2000, pp. 816-821.

Bennett et al., "Intraosseous Sliding Plate Fixation Used in Double Osteotomy Bunionectomy," Foot & Ankle International, vol. 40, No. 1, 2019, pp. 85-88.

Blomer, "Knieendoprothetik—Herstellerische Probleme und technologische Entwicklungen," Orthopade, vol. 29, 2000, pp. 688-696, including English Abstract on p. 689.

Bouaicha et al., "Fixation of Maximal Shift Scarf Osteotomy with Inside-Out Plating: Technique Tip," Foot & Ankle International, vol. 32, No. 5, May 2011, pp. 567-569.

Buda et al., "Effect of Fixation Type and Bone Graft on Tarsometatarsal Fusion," Foot & Ankle International, vol. 39, No. 12, 2018, pp. 1394-1402.

(56) References Cited

OTHER PUBLICATIONS

Carr et al., "Correctional Osteotomy for Metatarsus Primus Varus and Hallux Valgus," The Journal of Bone and Joint Surgery, vol. 50-A, No. 7, Oct. 1968, pp. 1353-1367.
Catanese et al., "Measuring Sesamoid Position in Hallux Valgus: When Is the Sesamoid Axial View Necessary," Foot and Ankle Specialist, 2014, 3 pages.
Chesser et al., "New Advances With The Tarsometatarsal Arthrodesis," Podiatry Today, vol. 30, No. 10, Sep. 27, 2017, 15 pages.
Chomej et al., "Lateralising DMMO (MIS) for simultaneous correction of a pes adductus during surgical treatment of a hallux valgus," The Foot, vol. 45, Dec. 2020, 33 pages.
Cichero et al., "Different fixation constructs and the risk of non-union following first metatarsophalangeal joint arthrodesis," Foot and Ankle Surgery, vol. 27, 2021, pp. 789-792.
Coetzee et al., "Revision Hallux Valgus Correction," Operative Techniques in Foot and Ankle Surgery, Section I, Chapter 15, 2011, pp. 84-96.
Coetzee et al., "The Lapidus Procedure: A Prospective Cohort Outcome Study," Foot & Ankle International, vol. 25, No. 8, Aug. 2004, pp. 526-531.
Collan et al., "The biomechanics of the first metatarsal bone in hallux valgus: A preliminary study utilizing a weight bearing extremity CT," Foot and Ankle Surgery, vol. 19, 2013, pp. 155-161.
Conti et al., "Effect of the Modified Lapidus Procedure for Hallux Valgus on Foot Width," Foot & Ankle International, Feb. 1, 2020, published online: Oct. 30, 2019, 6 pages.
Conti et al., "Effect of the Modified Lapidus Procedure on Pronation of the First Ray in Hallux Valgus," Foot & Ankle International, Feb. 1, 2020, published online: Oct. 16, 2019, 8 pages.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Coughlin, "Fixation of the Lapidus Arthrodesis with a Plantar Interfragmentary Screw and Medial Low Profile Locking Plate," Orthopaedics and Traumatology, vol. 7, 1999, pp. 133-143.
Crawford et al., "Metatarsus Adductus: Radiographic and Pathomechanical Analysis," Chapter 5, 2014, 6 pages.
Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.
Curran et al., "Functional Capabilities After First Metatarsal Phalangeal Joint Arthrodesis Using a Locking Plate and Compression Screw Construct," The Journal of Foot & Ankle Surgery, vol. 61, No. 1, Jan./Feb. 2022, pp. 79-83.
D'Amico et al., "Motion of the First Ray: Clarification Through Investigation," Journal of the American Podiatry Association, vol. 69, No. 1, Jan. 1979, pp. 17-23.
Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.
Dalat et al., "Does arthrodesis of the first metatarsophalangeal joint correct the intermetatarsal M1M2 angle?Analysis of a continuous series of 208 arthrodeses fixed with plates," Orthopaedics & Traumatology: Surgery & Research, vol. 101, 2015, pp. 709-714.
Dayton et al., "Biomechanical Characteristics of Biplane Multiplanar Tension-Side Fixation for Lapidus Fusion," The Journal of Foot & Ankle Surgery, vol. 57, 2018, pp. 761-765.
Dayton et al., "Biwinged Excision for Round Pedal Lesions," The Journal of Foot and Ankle Surgery, vol. 35, No. 3, 1996, pp. 244-249.
Dayton et al., "Comparison of Radiographic Measurements Before and After Triplane Tarsometatarsal Arthrodesis for Hallux Valgus," The Journal of Foot & Ankle Surgery, vol. 59, 2020, pp. 291-297.
Dayton et al., "Comparison of Tibial Sesamoid Position on Anteroposterior and Axial Radiographs Before and After Triplane Tarsal Metatarsal Joint Arthrodesis," The Journal of Foot & Ankle Surgery, vol. 56, 2017, pp. 1041-1046.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
Dayton et al., "Evidence-Based Bunion Surgery: A Critical Examination of Current and Emerging Concepts and Techniques," Springer International Publishing, 2017, 254 pages.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Medial Incision Approach to the First Metatarsophalangeal Joint," The Journal of Foot and Ankle Surgery, vol. 40, No. 6, Nov./Dec. 2001, pp. 414-417.
Dayton et al., "Observed Changes in Radiographic Measurements of the First Ray after Frontal and Transverse Plane Rotation of the Hallux: Does the Hallux Drive the Metatarsal in a Bunion Deformity? ," The Journal of Foot and Ankle Surgery, vol. 53, 2014, pp. 584-587.
Dayton et al., "Progression of Healing on Serial Radiographs Following First Ray Arthrodesis in the Foot Using a Biplanar Plating Technique Without Compression," The Journal of Foot & Ankle Surgery, 2018, 7 pages.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton, "Tarsal-Metatarsal Joint: Primary & Revision Arthrodesis," Apr. 2014, 38 pages.
Boffeli et al., "Can We Abandon Saw Wedge Resection in Lapidus Fusion? A Comparative Study of Joint Preparation Techniques Regarding Correction of Deformity, Union Rate, and Preservation of First Ray Length," The Journal of Foot and Ankle Surgery, vol. 58, No. 6, Nov. 2019, published online: Sep. 25, 2019, pp. 1118-1124.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
"Foot and Ankle Instrument Set," Smith & Nephew, 2013, 2 pages.
"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.
"Reconstructive Surgery of the Foot & Ankle," The Podiatry Institute, Update 2015, Conference Program, May 2015, 28 pages.
"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
Dayton et al., "A new triplanar paradigm for bunion management," Lower Extremity Review, Apr. 2015, 9 pages.
Dayton et al., "A User-Friendly Method of Pin Site Management for External Fixators," Foot and Ankle Specialist, Sep. 16, 2011, 4 pages.
Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.

(56) References Cited

OTHER PUBLICATIONS

Dayton et al., "Clarification of the Anatomic Definition of the Bunion Deformity," The Journal of Foot and Ankle Surgery, vol. 53, 2014, pp. 160-163.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "Complications of Metatarsal Suture Techniques for Bunion Correction: A Systematic Review of the Literature," The Journal of Foot and Ankle Surgery, Article in Press, 2015, 3 pages.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.
Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length on Plain Radiographs: Reliability of a New Method," Foot and Ankle Specialist, vol. 4, No. 5, Oct. 2011, pp. 280-283.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.
Dayton et al., "Principles of Management of Growth Plate Fractures in the Foot and Ankle," Clinics in Podiatric Medicine and Surgery, Pediatric Foot Deformities, Oct. 2013, 17 pages.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton et al., "The Extended Knee Hemilithotomy Position for Gastrocnemius Recession," The Journal of Foot and Ankle Surgery, vol. 49, 2010, pp. 214-216.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
Decarbo et al., "Locking Plates: Do They Prevent Complications?," Podiatry Today, Apr. 2014, 7 pages.
Decarbo et al., "Resurfacing Interpositional Arthroplasty for Degenerative Joint Diseas of the First Metatarsalphalangeal Joint," Podiatry Management, Jan. 2013, pp. 137-142.
Decarbo et al., "The Weil Osteotomy: A Refresher," Techniques in Foot and Ankle Surgery, vol. 13, No. 4, Dec. 2014, pp. 191-198.
Deheer et al., "Procedure-Specific Hardware Removal After Evans Osteotomy," Journal of the American Podiatric Medical Association, vol. 110, No. 2, Mar./Apr. 2020, 7 pages.
Didomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Didomenico et al., "Lapidus Bunionectomy: First Metatarsal-Cuneiform Arthrodesis," McGlamrys Comprehensive Textbook of Foot and Ankle Surgery, Fourth Edition, vol. 1, Chapter 31, 2013, 24 pages.
Dinapoli et al., "Metatarsal Osteotomy for the Correction of Metatarsus Adductus," Reconstructive Surgery of the Foot and Leg, 1989, pp. 242-250.
"Futura Forefoot Implant Arthroplasty Products", Tornier, Inc., 2008, 14 pages.
Hat-Trick Lesser Toe Repair System, Foot and Ankle Technique Guide, Metatarsal Shortening Osteotomy Surgical Technique, Smith & Nephew, 2014, 16 pages.
Hat-Trick Lesser Toe Repair System, Smith & Nephew, Brochure, Aug. 2014, 12 pages.
Hoffmann II Compact External Fixation System, Stryker, Brochure, Literature No. 5075-1-500, 2006, 12 pages.
Hoffmann II Micro Lengthener, Stryker, Operative Technique, Literature No. 5075-2-002, 2008, 12 pages.
Hoffmann Small System External Fixator Orthopedic Instruments, Stryker, retrieved Dec. 19, 2014, from the Internet: <http://www.alibaba.com/product-detail/Stryker-Hoffmann-Small-System-External-Fixator_1438850129.html>, 3 pages.
"Patient to Patient Precision, Accu-Cut, Osteotomy Guide System," BioPro, Foot & Ankle International Journal, vol. 23, No. 8, Aug. 2002, 2 pages.
"Prophecy Inbone Preoperative Navigation Guides," Wright Medical Technology, Inc., Nov. 2013, 6 pages.
Rayhack Ulnar Shortening Generation II Low-Profile Locking System Surgical Technique, Wright Medical Technology, Inc., Dec. 2013, 20 pages.
Smith & Nephew scores a Hat-Trick with its entry into the high-growth hammer toe repair market, Smith & Nephew, Jul. 31, 2014, 2 pages.
"Lag Screw Target Bow," Stryker Leibinger GmbH & Co. KG, Germany 2004, 8 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.

(56) References Cited

OTHER PUBLICATIONS

Defendant Fusion Orthopedics LLC's Invalidity Contentions, No. CV-22-00490-PHX-SRB, US District Court for the District of Arizona, Aug. 27, 2022, 41 pages.
Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.
Rx-Fix Mini Rail External Fixator, Wright Medical Technology, Brochure, Aug. 15, 2014, 2 pages.
Saltzman et al., "Prospective Controlled Trial of STAR Total Ankle Replacement Versus Ankle Fusion: Initial Results," Foot & Ankle International, vol. 30, No. 7, Jul. 2009, pp. 579-596.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Santrock et al., "Hallux Valgus Deformity and Treatment: A Three-Dimensional Approach: Lapiplasty," Foot & Ankle Clinics, vol. 23, No. 2, 2018, pp. 281-295.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Schon et al., "Cuneiform-Metatarsal Arthrodesis for Hallux Valgus," The Foot and Ankle, Second Edition, Chapter 8, 2002, pp. 99-117.
Scranton Jr. et al., "Anatomic Variations in the First Ray: Part I. Anatomic Aspects Related to Bunion Surgery," Clinical Orthopaedics and Related Research, vol. 151, Sep. 1980, pp. 244-255.
Shima et al., "Operative Treatment for Hallux Valgus With Moderate to Severe Metatarsus Adductus," Foot & Ankle International, vol. 40, No. 6, 2019, pp. 641-647.
Shurnas et al., "Proximal Metatarsal Opening Wedge Osteotomy," Operative Techniques in Foot and Ankle Surgery, Section I, Chapter 13, 2011, pp. 73-78.
Siddiqui et al. "Fixation Of Metatarsal Fracture With Bone Plate In A Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simons et al., "Short-Term Clinical Outcome of Hemiarthroplasty Versus Arthrodesis for End-Stage Hallux Rigidus," The Journal of Foot & Ankle Surgery, vol. 54, 2015, pp. 848-851.
Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
Smith et al., "Intraoperative Multiplanar Alignment System to Guide Triplanar Correction of Hallux Valgus Deformity," Techniques in Foot & Ankle Surgery, 2017, 8 pages.
Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Smith et al., "Understanding Frontal Plane Correction in Hallux Valgus Repair," Clinics in Podiatric Medicine and Surgery, vol. 35, 2018, pp. 27-36.
Sokoloff, "Lapidus Procedure," Textbook of Bunion Surgery, Chapter 15, 1981, pp. 277-287.
Stableloc External Fixation System, Acumed, Product Overview, Effective date Sep. 2015, 4 pages.
Stahl et al., "Derotation Of Post-Traumatic Femoral Deformities By Closed Intramedullary Sawing," Injury, vol. 37, No. 2, Feb. 2006, pp. 145-151, (Abstract Only).
Stamatis et al., "Mini Locking Plate as Medial Buttress for Oblique Osteotomy for Hallux Valgus," Foot & Ankle International, vol. 31, No. 10, Oct. 2010, pp. 920-922.
Talbot et al., "Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Tricot et al., "3D-corrective osteotomy using surgical guides for posttraumatic distal humeral deformity," Acta Orthopaedica Belgica, vol. 78, No. 4, 2012, pp. 538-542.
Use for BME Speed Nitinol Staple Fixation for the Lapidus Procedure, "date unknown, 1 page."
Vaida et al., "Effect on Foot Width With Triplanar Tarsometatarsal Arthrodesis for Hallux Valgus," Foot & Ankle Orthopaedics, vol. 5, No. 3, 2020, pp. 1-5.
Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.
Vitek, "Neue Techniken in der Fuchirurgie Das V-tek-System," ABW Wissenschaftsverlag GmbH, 2009, 11 pages, including English Abstract.
Walker et al., "The Role of First Ray Insufficiency in the Development of Metatarsalgia," Foot and Ankle Clinics, vol. 24, No. 4, Dec. 2019, published online: Sep. 5, 2019, pp. 641-648.
Weber et al., "A Simple System For Navigation Of Bone Alignment Osteotomies Of The Tibia," International Congress Series, vol. 1268, Jan. 2004, pp. 608-613, (Abstract Only).
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Weigelt et al., "Risk Factors for Nonunion After First Metatarsophalangeal Joint Arthrodesis With a Dorsal Locking Plate and Compression Screw Construct: Correction of Hallux Valgus Is Key," The Journal of Foot & Ankle Surgery, vol. 60, No. 6, Nov./Dec. 2021, pp. 1179-1183.
Weil et al., "Anatomic Plantar Plate Repair Using the Weil Metatarsal Osteotomy Approach," Foot & Ankle Specialist, vol. 4, No. 3, 2011, pp. 145-150.
Wendl et al., "Navigation in der Knieendoprothetik," OP-Journal, vol. 17, 2002, pp. 22-27, including English Abstract.
Whipple et al., "Zimmer Herbert Whipple Bone Screw System: Surgical Techniques for Fixation of Scaphoid and Other Small Bone Fractures," Zimmer, 2003, 59 pages.
Wienke et al., "Bone Stimulation For Nonunions: What the Evidence Reveals," Podiatry Today, vol. 24, No. 9, Sep. 2011, pp. 52-57.
Williams et al., "Metatarsus adductus: Development of a nonsurgical treatment pathway," Journal of Paediatrics and Child Health, vol. 49, 2013, pp. E428-433.
Wukich et al., "Hypermobility of the First Tarsometatarsal Joint," Foot and Ankle Clinics, vol. 10, No. 1, Mar. 2005, pp. 157-166.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Yasuda et al., "Proximal Supination Osteotomy of the First Metatarsal for Hallux Valgus," Foot and Ankle International, vol. 36, No. 6, Jun. 2015, pp. 696-704.
Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).
Doty et al., "Hallux valgus and hypermobility of the first ray: facts and fiction," International Orthopaedics, vol. 37, 2013, pp. 1655-1660.

(56) References Cited

OTHER PUBLICATIONS

Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Easley et al., "Current Concepts Review: Hallux Valgus Part II: Operative Treatment," Foot and Ankle International, vol. 28, No. 6, Jun. 2007, pp. 748-758.
Easley et al., "What is the Best Treatment for Hallux Valgus?," Evidence-Based Orthopaedics—The Best Answers to Clinical Questions, Chapter 73, 2009, pp. 479-491.
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
Eustace et al., "Hallux valgus, first metatarsal pronation and collapse of the medial longitudinal arch—a radiological correlation," Skeletal Radiology, vol. 23, 1994, pp. 191-194.
Fallin et al., US Provisional Application Entitled Indexed Tri-Planar Osteotomy Guide and Method, U.S. Appl. No. 62/118,378, filed Feb. 19, 2015, 62 pages.
Fazal et al., "First metatarsophalangeal joint arthrodesis with two orthogonal two hole plates," Acta Orthopaedica et Traumatologica Turcica, vol. 52, 2018, pp. 363-366.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
Ferrari et al., "A Radiographic Study of the Relationship Between Metatarsus Adductus and Hallux Valgus," The Journal of Foot and Ankle Surgery, vol. 42, No. 1, 2003, pp. 9-14.
Ferreyra et al., "Can we correct first metatarsal rotation and sesamoid position with the 3D Lapidus procedure?," Foot and Ankle Surgery, vol. 28, No. 3, Apr. 2022, pp. 313-318.
Fishco, "A Straightforward Guide To The Lapidus Bunionectomy," Podiatry Today, Retrieved online from <https://www.hmpglobal-learningnetwork.com/site/podiatry/blogged/straightforward-guide-lapidus-bunionectomy>, dated Sep. 6, 2013, 5 pages.
Fishco, "Making the Lapidus Easy," The Podiatry Institute, Update 2014, Chapter 14, 2014, pp. 91-93.
Flavin et al., "Arthrodesis of the First Metatarsophalangeal Joint Using a Dorsal Titanium Contoured Plate," Foot & Ankle International, vol. 25, No. 11, Nov. 2004, pp. 783-787.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Fraissler et al., "Treatment of hallux valgus deformity," Efort Open Reviews, vol. 1, Aug. 2016, pp. 295-302.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.
Garthwait, "Accu-Cut System Facilitates Enhanced Precision," Podiatry Today, vol. 18, No. 6, Jun. 2005, 6 pages.
Gerard et al., "The Modified Lapidus Procedure," Orthopedics, vol. 31, No. 3, Mar. 2008, 7 pages.
Ghali et al., "The Management of Metatarsus Adductus et Supinatus," The Journal of Bone and Joint Surgery, vol. 66-B, No. 3, May 1984, pp. 376-380.
Giannoudis et al., "Hallux Valgus Correction," Practical Procedures in Elective Orthopaedic Surgery, Pelvis and Lower Extremity, Chapter 38, 2012, 22 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Gotte, "Entwicklung eines Assistenzrobotersystems fr die Knieendoprothetik," Forschungsberichte, Technische Universitat Munchen, 165, 2002, 11 pages, including partial English Translation.
Gould et al., "A Prospective Evaluation of First Metatarsophalangeal Fusion Using an Innovative Dorsal Compression Plating System," The Journal of Foot & Ankle Surgery, vol. 60, 2021, pp. 891-896.
Gregg et al., "Plantar plate repair and Weil osteotomy for metatarsophalangeal joint instability," Foot and Ankle Surgery, vol. 13, 2007, pp. 116-121.
Greiner, "The Jargon of Pedal Movements," Foot & Ankle International, vol. 28, No. 1, Jan. 2007, pp. 109-125.
Grondal et al., "A Guide Plate for Accurate Positioning of First Metatarsophalangeal Joint during Fusion," Operative Orthopdie Und Traumatologie, vol. 16, No. 2, 2004, pp. 167-178 (Abstract Only).
Groves, "Functional Position Joint Sectioning: Pre-Load Method for Lapidus Arthrodesis," The Podiatry Institute, Update 2015, Chapter 6, 2015, pp. 23-29.
Groves, "Operative Report," St. Tammany Parish Hospital, Date of Procedure, Mar. 26, 2014, 2 pages.
Gutteck et al., "Comparative study of Lapidus bunionectomy using different osteosynthesis methods," Foot and Ankle Surgery, vol. 19, 2013, pp. 218-221.
Gutteck et al., "Is it feasible to rely on intraoperative X ray in correcting hallux valgus?," Archives of Orthopaedic and Trauma Surgery, vol. 133, 2013, pp. 753-755.
Hardy et al., "Observations on Hallux Valgus," The Journal of Bone and Joint Surgery, vol. 33B, No. 3, Aug. 1951,pp. 376-391.
Hatch et al., "Analysis of Shortening and Elevation of the First Ray With Instrumented Triplane First Tarsometatarsal Arthrodesis," Foot & Ankle Orthopaedics, vol. 5, No. 4, 2020, pp. 1-8.
Hatch et al., "Triplane Hallux Abducto Valgus Classification," The Journal of Foot & Ankle Surgery, vol. 57, No. 5, Sep./Oct. 2018, published online: May 18, 2018, pp. 972-981.
Hetherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
Ho et al., "Hallux rigidus," Efort Open Reviews, vol. 2, Jan. 2017, pp. 13-20.
Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.
Hunt et al., "Locked Versus Nonlocked Plate Fixation For Hallux MTP Arthrodesis," Foot and Ankle International, vol. 32, No. 7, Jul. 2011, pp. 704-709.
Integra, "Integra Large Qwix Positioning and Fixation Screw, Surgical Technique," 2012, 16 pages.
International Search Report and Written Opinion, International Patent Application No. PCT/US204/041964, mailed Aug. 12, 2024, 13 pages.
Jackson III et al., "The Surgical Learning Curve for Modified Lapidus Procedure for Hallux Valgus Deformity," Foot & Ankle Specialist, Jul. 2021, 5 pages.
Jeuken et al., "Long-term Follow-up of a Randomized Controlled Trial Comparing Scarf to Chevron Osteotomy in Hallux Valgus Correction," Foot & Ankle International, vol. 37, No. 7, 2016, pp. 687-695.
Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.
Kim et al., "A Multicenter Retrospective Review of Outcomes for Arthrodesis, Hemi-Metallic Joint Implant, and Resectional Arthroplasty

(56) References Cited

OTHER PUBLICATIONS in the Surgical Treatment of End-Stage Hallux Rigidus," The Journal of Foot and Ankle Surgery, vol. 51, 2012, pp. 50-56.
Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
Klos et al., "Modified Lapidus arthrodesis with plantar plate and compression screw for treatment of hallux valgus with hypermobility of the first ray: A preliminary report," Foot and Ankle Surgery, vol. 19, 2013, pp. 239-244.
Kurup et al., "Midfoot arthritis—current concepts review," Journal of Clinical Orthopaedics and Trauma, vol. 11, 2020, pp. 399-405.
La Reaux et al., "Metatarsus adductus and hallux abducto valgus: their correlation," The Journal of Foot Surgery, vol. 26, No. 4, Jul. 1987, pp. 304-308, Abstract Only.
Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.
Lapidus, "The Author's Bunion Operation From 1931 to 1959," Clinical Orthopaedics, vol. 16, 1960, pp. 119-135.
Latif et al., "First metatarsophalangeal fusion using joint specific dorsal plate with interfragmentary screw augmentation: Clinical and radiological outcomes," Foot and Ankle Surgery, vol. 25, 2019, pp. 132-136.
Le et al., "Tarsometatarsal Arthrodesis," Operative Techniques in Foot and Ankle Surgery, Section II, Chapter 40, 2011, pp. 281-285.
Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.
Li et al., "Evolution of Thinking of the Lapidus Procedure and Fixation," Foot and Ankle Clinics, vol. 25, No. 1, Mar. 2020, published online: Dec. 16, 2019, pp. 18 pages.
Lieske et al., "Implantation einer Sprunggelenktotalendo-prothese vom Typ Salto 2," Operative Orthopdie und Traumatologie, vol. 26, No. 4, 2014, pp. 401-413, including English Abstract on p. 403.
Little, "Joint Arthrodesis For Hallux Valgus," Clinics in Podiatric Medicine and Surgery, Hallux Abducto Valgus Surgery, updated Apr. 19, 2014, retrieved online from <https://www.footankleinstitute.com/first-metatarsophalangeal-joint-arthrodesis-in-the-treatment-of-hallux-valgus>, 7 pages.
Lopez et al., "Metatarsalgia: Assessment Algorithm and Decision Making," Foot and Ankle Clinics, vol. 24, No. 4, Dec. 2019, published online: Sep. 25, 2019, pp. 561-569.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Machacek Jr. et al., "Salvage of a Failed Keller Resection Arthroplasty," The Journal of Bone and Joint Surgery, vol. 86A, No. 6, Jun. 2004, pp. 1131-1138.
Magin, "Computernavigierter Gelenkersatz am Knie mit dem Orthopilot," Operative Orthopdie und Traumatologie, vol. 22, No. 1, 2010, pp. 63-80, including English Abstract on p. 64.
Magin, "Die belastungsstabile Lapidus-Arthrodese bei Hallux-valgus-Deformitt mittels IVP-Plattenfixateur (V-TEK-System)," Operative Orthopdie und Traumatologie, vol. 26, No. 2, 2014, pp. 184-195, including English Abstract on p. 186.
Marshall et al., "The identification and appraisal of assessment tools used to evaluate metatarsus adductus: a systematic review of their measurement properties," Journal of Foot and Ankle Research, vol. 11, No. 25, 2018, 10 pages.
Mcaleer et al., "A systematic approach to the surgical correction of combined hallux valgus and metatarsus adductus deformities," The Journal of Foot & Ankle Surgery, May 21, 2021, 6 pages.
Mcaleer et al., "Radiographic Outcomes Following Triplanar Correction of Combined Hallux Valgus and Metatarsus Adductus Deformities," ACFAS Scientific Conference, Poster, Feb. 2022, 1 page.
Mccabe et al., "Anatomical reconstruction of first ray instability hallux valgus with a medial anatomical TMTJ1 plate," Foot and Ankle Surgery, vol. 27, No. 8, Dec. 2021, pp. 869-873.
Mehtar et al., "Outcomes of bilateral simultaneous hallux MTPJ fusion," Foot and Ankle Surgery, vol. 27, 2021, pp. 213-216.
Miller et al., "Variable Angle Locking Compression Plate as Alternative Fixation for Jones Fractures: A Case Series," Kansas Journal of Medicine, vol. 12, No. 2, May 2019, pp. 28-32.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Mizuno et al., "Detorsion Osteotomy of the First Metatarsal Bone in Hallux Valgus," Japanese Orthopaedic Association, Tokyo, 1956; 30:813-819.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect Of Ankle Flexion Angle On Axial Alignment Of Total Ankle Replacement," Foot and Ankle International, vol. 31, No. 12, Dec. 2010, pp. 1093-1098, (Abstract Only).
Mortier et al., "Axial Rotation of the First Metatarsal Head in a Normal Population and Hallux Valgus Patients," Orthopaedics and Traumatology: Surgery and Research, vol. 98, 2012, pp. 677-683.
Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.
Myerson, "Cuneiform-Metatarsal Arthrodesis," The Foot and Ankle, Chapter 9, 1997, pp. 107-117.
Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Nix et al., "Prevalence of hallux valgus in the general population: a systematic review and meta-analysis," Journal of Foot and Ankle Research, vol. 3, No. 21, 2010, 9 pages.
Odenbring et al., "A guide instrument for high tibial osteotomy," Acta Orthopaedica Scandinavica, vol. 60, No. 4, 1989, pp. 449-451.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.
Otsuki et al., "Developing a novel custom cutting guide for curved per-acetabular osteotomy," International Orthopaedics (SICOT), vol. 37, 2013, pp. 1033-1038.
Park et al., "Comparative analysis of clinical outcomes of fixed-angle versus variable-angle locking compression plate for the treatment of Lisfranc injuries," Foot and Ankle Surgery, vol. 26, 2020, pp. 338-342.

(56) References Cited

OTHER PUBLICATIONS

Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
Pentikainen et al., "Preoperative Radiological Factors Correlated to Long-Term Recurrence of Hallux Valgus Following Distal Chevron Osteotomy," Foot & Ankle International, vol. 35, No. 12, 2014, pp. 1262-1267.
Peters et al., "Flexor Hallucis Longus Tendon Laceration as a Complication of Total Ankle Arthroplasty," Foot & Ankle International, vol. 34, No. 1, 2013, pp. 148-149.
Ray et al., "Hallux Valgus," Foot & Ankle Orthopaedics, vol. 4, No. 2, 2019, pp. 1-12.
Ray et al., "Multicenter Early Radiographic Outcomes of Triplanar Tarsometatarsal Arthrodesis With Early Weightbearing," Foot & Ankle International, vol. 40, No. 8, 2019, pp. 955-960.
Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.
Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.
Michelangelo Bunion System, Surgical Technique, Instratek Incorporated, publication date unknown, 4 pages.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.

DEVICES AND LESS INVASIVE TECHNIQUES FOR TREATING LESSER METATARSALS OF THE FOOT

CROSS-REFERENCE

This application claims the benefit of U.S. Provisional Application No. 63/519,180, filed Aug. 11, 2023, the entire contents of which are incorporated herein by reference.

TECHNICAL FIELD

This disclosure relates to devices and less invasive techniques for treating bones of the foot, such as one or more lesser metatarsals of the foot.

BACKGROUND

Metatarsus adductus (MTA) is a deformity of the foot in which the metatarsals are angulated into adduction. MTA is typically characterized by a medial deviation of the metatarsals in the transverse plane. For example, MTA is often described as a structural deformity occurring at the Lisfranc joint (tarsometatarsal joints), with the metatarsals deviating medially with reference to the lesser tarsus.

In some patients, MTA presents with hallux valgus, also referred to as hallux abducto valgus. Hallux valgus is a complex progressive condition that is characterized by lateral deviation (valgus, abduction) of the hallux and medial deviation of the first metatarsophalangeal joint. Hallux valgus typically results in an increase in the hallux adductus angle, which is the angle between the long axes of the first metatarsal and proximal phalanx in the transverse plane.

In some cases, surgical intervention is needed to address MTA, hallux valgus, and/or other conditions of the foot. During orthopedic surgery, the clinician may make one or more incisions through the patient's skin to access the underlying bones to perform the procedure. A longer incision provides the surgeon with greater access to perform the procedure. However, a longer incision results in a longer scar for the patient after healing, which can be cosmetically undesirable. For this reason, the patient may prefer a shorter incision and/or fewer incisions. This can be challenging for the surgeon because it limits access for performing the procedure. Surgical instruments that can facilitate less invasive, efficient, accurate, and reproducible clinical results are useful for practitioners performing orthopedic surgical procedures.

SUMMARY

In general, this disclosure is directed to devices and less invasive techniques for using such devices for realignment and/or fusion of one or more bones in the foot. For example, various devices and techniques may be utilized to treat metatarsus adductus (MTA), hallux valgus, arthritis, and/or other conditions of the foot. In some implementations, the devices and techniques are configured for use on one or more lesser metatarsals and/or lesser tarsometatarsal (TMT) joint, such as one or more of the second, third, fourth, and/or fifth metatarsals and/or one or more of the intermediate cuneiform, lateral cuneiform, and/or cuboid. For example, one or more cut guides and/or other instruments may be designed to accommodate the specific anatomical conditions of one or more lesser metatarsals and/or TMT joints of the foot and facilitate a surgical procedure utilizing a comparatively small incision.

In some examples, surgical devices and/or techniques described herein may be implemented on a second and/or third TMT joint. For example, a clinician may surgically access the second and/or third tarsometatarsal joints of the foot to prepare the joints for realignment and fusion. The clinician may make an incision, e.g., providing dorsolateral and dorsomedial access, to the second and/or third tarsometatarsal joints. With the joints exposed, the clinician may prepare the end faces of the second and/or third metatarsals and opposed intermediate and/or lateral cuneiforms, respectively. Before or after preparing the one or more joints, the clinician may realign one or more lesser metatarsals in the transverse plane, frontal plane, and/or sagittal plane to realign the metatarsal. Additionally or alternatively, the clinician may compress the prepared end faces of the bones together. After suitable preparation and repositioning, the clinician can fixate one or more of the joins to promote fusion across the joints.

In some implementations, the second and third tarsometatarsal joints are prepared and the second and third metatarsals independently moved from each other in one or more planes, such as the transverse plane. In other implementations, the second and third tarsometatarsal joints can be prepared and the second and third metatarsals moved together to address the angular misalignment of the metatarsals. For example, when accessing and preparing the second and third tarsometatarsal joints, the plantar tarsometatarsal ligaments and the ligaments between the second and third metatarsals may be preserved (e.g., remain uncut or unbroken). This can maintain the connective tissue between the second and third metatarsals, allowing the second and third metatarsals to be manipulated as an interconnected block or group during angular realignment. In addition to realigning the second and third metatarsals, the fourth and fifth metatarsals may or may not also be realigned to help correct a bone deformity, such as metatarsus adductus.

While a less invasive surgical technique according to the disclosure may involve surgically accessing and preparing multiple lesser tarsometatarsal joints of the foot, such as the second and third tarsometatarsal joints, in some implementations a technique can be performed on a single lesser tarsometatarsal joint (e.g., the second tarsometatarsal joint, the third tarsometatarsal joint, the fourth tarsometatarsal joint, and/or the fifth tarsometatarsal joint). This procedure on the single lesser tarsometatarsal joint may be performed either alone or in combination with treatment of hallux valgus on the first metatarsal. For example, a MTA deformity or other bone deformity may be corrected by operating on a single lesser tarsometatarsal joint (e.g., the second tarsometatarsal joint, the third tarsometatarsal joint) without operating on other lesser tarsometatarsal joints, again optionally with alignment correction of the first metatarsal through a procedure performed on the first tarsometatarsal joint. In yet other examples, a clinician may utilize instruments and/or techniques according to the disclosure on the first metatarsal and/or first TMT joint without performing a surgical procedure on a lesser metatarsal and/or lesser TMT joint.

Independent of the specific surgical technique performed during a treatment procedure, a variety of different instruments may be provided to help facilitate bone preparation and/or realignment techniques. The instruments may be utilized as part of a metatarsal adductus treatment procedure or yet other treatment procedure (e.g., fusion of an arthritic joint, realignment of a bone other than a metatarsal). For example, a bone cutting guide may be used to help cut an end face of a metatarsal and/or cuneiform to facilitate realignment and/or fusion between bones through a small incision. In general, the bone cutting guide may be sized and shaped to be positioned over one or more bones to be cut.

According to some aspects of the disclosure, a less invasive technique for treating lesser metatarsals of a foot is disclosed. The technique including: making an incision through a skin of a patient; positioning at least a portion of a bone cutting guide comprising a body extending lengthwise from a medial side to a lateral side through the incision; retracting the skin along the incision to expose at least a portion of the bone cutting guide positioned over a first joint; guiding a cutting instrument along a first surface of the bone cutting guide to prepare the first joint; repositioning the skin along the incision to expose at least a portion of the bone cutting guide positioned over a second joint, thereby covering the portion of the first joint; and guiding a cutting instrument along a second surface of the bone cutting guide to prepare the second joint. The positioning of the skin along the incision may be done using at least one of a skin feature on the medial side of the body of the bone cutting guide and a second skin feature on the lateral side of the body of the bone cutting guide.

In additional aspects, the less invasive technique for treating lesser metatarsals of a foot may include: making an incision through a skin of a patient; positioning a portion of a bone cutting guide comprising a body extending lengthwise from a medial side to a lateral side through the incision, wherein each of the medial side and the lateral side includes a skin cutout feature; retracting the skin along the incision to expose at least a portion of a first bone under the lateral side of the bone cutting guide using the skin cutout feature of the medial side; guiding a cutting instrument along a first surface of the bone cutting guide to prepare the first bone; repositioning the skin along the incision to expose at least a portion of a second bone under the medial side of the bone cutting guide using the skin cutout feature of the lateral side; and guiding a cutting instrument along a second surface of the bone cutting guide to prepare the second bone.

In some examples, the technique additionally includes positioning the first surface of the bone cutting guide over at least one cuneiform of a foot and positioning the second surface of the bone cutting guide over at least one metatarsal of the foot. Further, after preparing the first bone and the second bone, a separation distance between the first bone and the second bone can be adjusted; and a moved position of the first bone and the second bone can be fixed using a bone connector.

The step of adjusting the separation distance between the first bone and the second bone can include correcting an alignment of the first bone in relation to the second bone in at least one plane and/or positioning an incision guide over a joint locator pin, wherein the incision guide defines a length of the incision.

In accordance with yet additional aspects, a bone cutting guide includes: a body extending lengthwise from a medial sidewall to a lateral sidewall and defining a cuneiform-side guide surface and a metatarsal-side guide surface; wherein the cuneiform-side guide surface is configured to be positioned over at least one cuneiform of a foot, and the cuneiform-side guide surface is configured to guide a cutting instrument to cut the at least one of cuneiform; the metatarsal-side guide surface is configured to be positioned over at least one metatarsal, and the metatarsal-side guide surface is configured to guide the cutting instrument to cut the at least one metatarsal; and at least one of the medial sidewall and the lateral sidewall extends from a top end to a bottom end and includes a cutout feature configured to enable the positioning of one or both of the at least one of the bottom end of the medial sidewall and the bottom end of the lateral sidewall inside a skin incision and of one or both of the at least one of the top end of the medial sidewall and the top end of the lateral sidewall outside of the skin incision.

In some embodiments, a seeker element extending between a bone contacting surface of the metatarsal-side guide surface and a bone contacting surface of the cuneiform-side guide surface may be included.

The medial sidewall and the lateral sidewall can converge at the bottom end and the cut guide may also be configured with a plurality of pin holes extending from the bone cutting guide configured for temporary fixation of the bone cutting guide on or near one or both of at least one cuneiform and at least one metatarsal. At least one of the plurality of pin holes may be at an angle that is relative to a position of the guide serving as a visualization orientation indicator. For example, the arrangement of the pin holes may be such that they extend in linearly in a direction that is about perpendicular to the plane of one or both of the metatarsal-side guide surface and the cuneiform-side guide surface.

The details of one or more examples are set forth in the accompanying drawings and the description below. Other features, objects, and advantages will be apparent from the description and drawings, and from the claims.

DETAILED DESCRIPTION

Figure 1B:
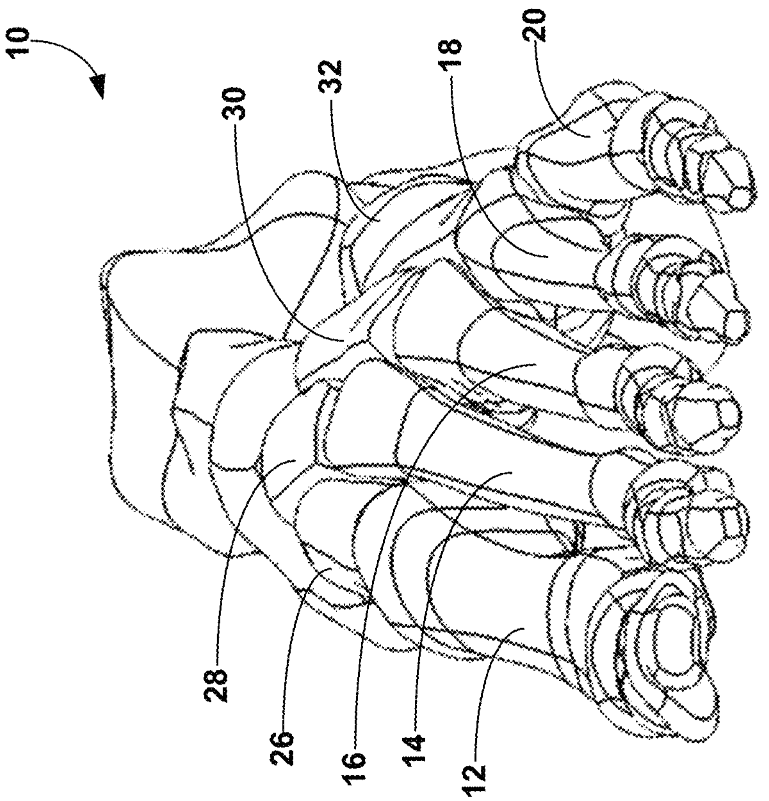
FIGS. 1A and 1B are top and front views, respectively, of a foot showing normal metatarsal alignment positions.

In general, the present disclosure is directed to devices and techniques for preparing one or more tarsometatarsal joints ("TMT joint") for fusion utilizing a comparatively small incision and realigning one or more metatarsals separated from an opposed bone by the tarsometatarsal joint. While a technique according to disclosure can be performed on any TMT joint, in some implementations, a surgical technique is performed on at least the second TMT joint and the third TMT joint. During the procedure, the clinician may cut an end of one or both of the second metatarsal and opposed intermediate cuneiform. Additionally or alternatively, the clinician may cut an end of one or both of the third metatarsal and opposed lateral cuneiform. In some examples the clinician advances a cutting instrument along a path (e.g., a linear path and/or a curved path) to cut one metatarsal end followed by another metatarsal end and/or to cut one cuneiform end followed by another cuneiform end. In either case, a bone portion may be removed from the TMT joint space, such as between both the second TMT joint space and the third TMT joint space. The bone portion and/or space from which the bone portion is removed may be shaped to facilitate subsequent repositioning of the metatarsal relative to the opposed cuneiform, e.g., by moving the metatarsal to partially or fully close the space created upon removal of the bone portion.

Some examples of the present disclosure provide a minimally invasive technique and bone cutting guide for treating one or more lesser metatarsals of a foot. The technique can involve making a comparatively small incision through the skin of a patient and positioning a bone cutting guide through the incision. The bone cutting guide may include a body extending from a medial side to a lateral side, with defined medial and lateral side skin cutout features. The method may include retracting the skin along the incision to expose a portion of a first bone, guiding a cutting instrument along a first side guide surface of the bone cutting guide to cut the first bone, repositioning the skin to expose a portion of a second bone, and guiding the cutting instrument along a second side guide surface to prepare the second bone. The bone cutting guide may include a medial side shelf positionable under the skin of the patient, a lateral side shelf positionable under the skin of the patient, and an intermediate portion projecting outwardly through the incision. In some examples, one or both of the medial and lateral sides of the bone cutting guide may include an upper portion positionable over the skin of the patient and a lower portion positionable under the skin of the patient, with the upper portion and lower portion collectively defining one or more guide surfaces for guiding a cutting instrument.

In some examples, the technique may involve making an incision to access two tarsometatarsal joints where the incision is shorter than a length necessary to simultaneously expose both tarsometatarsal joints under through the incision. For example, the incision may have a length less than or equal to 5.0 mm, such as less than or equal to 4.5 mm, less than or equal to 4.0 mm, or less than or equal to 3.5 mm. The clinician can manipulate positioning of the skin relative to one or more skin cutout features of the bone cutting guide to separately access the two tarsometatarsal joints.

For example, the clinician can retract (e.g., pull) the skin medially along the incision line to expose a medial one of the two tarsometatarsal joints, thereby causing the skin on the lateral side of the incision line to cover a lateral portion of the bone cutting guide (and position the skin at least partially over the lateral one of the two tarsometatarsal joints). The clinician can then use the bone cutting guide to guide a cutting instrument to cut the ends of the bones forming the medial one of the two tarsometatarsal joints (e.g., cutting off an end portion of an intermediate cuneiform and cutting off an end portion of a second metatarsal). The clinician can additionally or alternatively prepare the ends of the bones forming the medial one of the two tarsometatarsal joints using other bone preparation techniques (e.g., fenestration). Before or after preparing the ends of the bones forming the medial one of the two tarsometatarsal joints, the clinician can access and prepare the ends of the bones forming the lateral one of the two tarsometatarsal joints. For example, the clinician can retract (e.g., pull) the skin laterally along the incision line to expose a lateral one of the two tarsometatarsal joints, thereby causing the skin on the medial side of the incision line to cover a medial portion of the bone cutting guide (and position the skin at least partially over the medial one of the two tarsometatarsal joints). The clinician can then use the bone cutting guide to guide a cutting instrument to cut the ends of the bones forming the lateral one of the two tarsometatarsal joints (e.g., cutting off an end portion of a lateral cuneiform and cutting off an end portion of a third metatarsal). The clinician can additionally or alternatively prepare the ends of the bones forming the lateral one of the two tarsometatarsal joints using other bone preparation techniques (e.g., fenestration).

By configuring the bone cutting guide to be at least partially positionable under the skin of the patient and to facilitate repositioning of the skin medially and/or laterally relative to the bone cutting guide to expose different portions of the guide and corresponding bones thereunder, the bone cutting guide can facilitate a less invasive technique. This can allow the clinician to access and prepare multiple lesser tarsometatarsal joints through a single incision that is sized smaller than the length of an incision required to have both joints exposed for surgical access at the same time.

While a bone cutting guide according to the disclosure can have a variety of different configurations, in some examples, the bone cutting guide includes a seeker positionable in one or more tarsometatarsal joints. The seeker can be attached to (e.g., integrally connected with) and extend from a body of the bone cutting guide defining one or more guide surfaces. The seeker can be useful for orienting the one or more guide surfaces relative to the one or more tarsometatarsal joints. In some examples, the seeker is detachably attached to the body of the bone cutting guide. For example, the bone cutting guide may comprise multiple bodies each defining one or more guide surfaces, where the multiple bodies are separately attachable to the seeker. As one example, the bone cutting guide may include a medial body for preparing a medial one of the two tarsometatarsal joints and a lateral body for preparing a lateral one of the two tarsometatarsal joints. The clinician can detach one body and attach another of the bodies to sequentially prepare different ones of the two tarsometatarsal joints (e.g., prepare different sets of the bone pairs forming each tarsometatarsal joint).

Independent of how one or more TMT joints are prepared, the clinician can apply a force to one or more metatarsals, such as the second and/or third metatarsals, to rotate the one or more metatarsals in at least one plane (e.g., one or more of the transverse plane, frontal plane, and/or sagittal plane).

When repositioning both the second and third metatarsals, the second and third metatarsals may or may not remain interconnected through ligamentous attachments, such as the plantar ligaments and/or second-to-third intermetatarsal ligaments. When remaining interconnected, the second and third metatarsals may be pivoted together as a block (e.g., in at least one plane, such as the transverse plane). For example, the second and third metatarsals may pivot generally about a medial aspect (e.g., side) of the second TMT joint in the transverse plane, closing a larger opening on the lateral side of the joint. In some implementations, the second and/or third metatarsals may be pivoted in at least the transverse plane with the second metatarsal base being attached to the Lisfranc ligament to serve as a pivot point about which the bone block can rotate. The clinician can pivot the second and third metatarsals by hand and/or with the aid of a bone positioner that engages with at least one of the second and third metatarsals and a bone other than that with which the bone positioner is engaged.

The fourth and fifth metatarsals may also pivot in one or more planes (e.g., at least the transverse plane), such as concurrent with the second and/or third metatarsals being pivoted in one or more planes. The fourth and fifth metatarsals may realign without accessing or preparing the fourth or fifth TMT joints. That being said, in some examples, the fourth and/or fifth metatarsals may be surgically accessed and prepared by preparing an end of the fourth metatarsal and/or opposed cuboid bone and/or an end of the fifth metatarsal and/or opposed cuboid bonc. After suitably realigning one or more of the second, third, fourth and/or fifth metatarsals, the moved position of the one or more metatarsals may be fixated. In some examples, a provisional fixation step is performed in which one or more temporary fixation pins are deployed to hold the moved position of one or more metatarsals (e.g., by inserting the fixation pin through one or more moved metatarsal(s) and into one or more adjacent bones). A permanent fixation device can be used to hold a moved position of a bone for subsequent fusion. Example permanent fixation devices include, but are not limited to, pins (e.g., intramedullary nail, K-wire, Steinmann pin), plates, screws, staples, and combinations.

Before, after, or concurrent with preparing and moving one or more lesser metatarsals (e.g., one or more of the second, third, fourth, and/or fifth metatarsals), the clinician may prepare and move the first metatarsal. The clinician may prepare the end of the first metatarsal and also prepare the opposed end of the medial cuneiform. Before or after preparing one or both bone ends, the clinician can move the first metatarsal in one or more planes. For example the clinician may pivot the distal end of the first metatarsal in the transverse plane to close an intermetatarsal angle between the first and second metatarsals. Additionally or alternatively, the clinician may rotate the first metatarsal in the frontal plane and/or adjust the angular alignment of the first metatarsal in the sagittal plane. With the first metatarsal suitably realigned, the clinician can fixate the moved position of the first metatarsal.

Details on example realignment instruments and techniques that can be used in conjunction with the present disclosure are described in U.S. Pat. No. 9,622,805, issued Apr. 18, 2017 and entitled "BONE POSITIONING AND PREPARING GUIDE SYSTEMS AND METHODS," U.S. Pat. No. 10,245,088, issued Apr. 2, 2019 and entitled "BONE PLATING SYSTEM AND METHOD," US Patent Publication No. 2020/0015856, published Jan. 16, 2020 and entitled "COMPRESSOR-DISTRACTOR FOR ANGULARLY REALIGNING BONE PORTIONS," US Patent Publication No. 2020/0015870, published Jan. 16, 2020 and entitled "MULTI-DIAMETER BONE PIN FOR INSTALLING AND ALIGNING BONE FIXATION PLATE WHILE MINIMIZING BONE DAMAGE" and US Patent Publication No. 2021/0361330, published Nov. 25, 2021 and entitled "DEVICES AND TECHNIQUES FOR TREATING METATARSUS ADDUCTUS." The entire contents of each of these patent documents are incorporated herein by reference.

Preparation and fusion of one or more TMT joints may be performed according to the disclosure for a variety of clinical reasons and indications. Preparation and fusion of a TMT joint may be performed to treat metatarsus adductus, hallux valgus, arthritis, and/or other bone and/or joint conditions.

Metatarsus adductus is a deformity of the foot characterized by a transverse plane deformity where the metatarsals are adducted at the Lisfranc joint. The extent of a metatarsus adductus deformity can be characterized by a metatarsus adductus angle. The metatarsus adductus angle can be defined as the angle between the longitudinal axis of the second metatarsal (representing the longitudinal axis of the metatarsus) and the longitudinal axis of the lesser tarsus. The measurement of the longitudinal axis of the lesser tarsus can be characterized by a line perpendicular to the transverse axis of the lesser tarsus using the lateral joint of the fourth metatarsal with the cuboid as a reference.

Hallux valgus, also referred to as hallux abducto valgus, is a complex progressive condition that is characterized by lateral deviation (valgus, abduction) of the hallux and medial deviation of the first metatarsophalangeal joint. Hallux valgus typically results in a progressive increase in the hallux adductus angle, the angle between the long axes of the first metatarsal and proximal phalanx in the transverse plane. An increase in the hallux adductus angle may tend to laterally displace the plantar aponeurosis and tendons of the intrinsic and extrinsic muscles that cross over the first metatarsophalangeal joint from the metatarsal to the hallux. Consequently, the sesamoid bones may also be displaced, e.g., laterally relative to the first metatarsophalangeal joint, resulting in subluxation of the joints between the sesamoid bones and the head of the first metatarsal. This can increase the pressure between the medial sesamoid and the *crista* of the first metatarsal head.

While techniques and devices are described herein particularly in connection with TMT joints of the foot, the techniques and/or devices may be used on other similar bones separated by a joint in the hand or foot. For example, the techniques and devices may be performed on the carpometacarpal joints of the hand. As another example, one or more techniques and/or devices may be used on a metatarsal and/or phalanx, e.g., across a metatarsophalangeal joint. In various implementations, the devices and/or techniques can be used as part of a bone alignment, osteotomy, fusion, fracture repair, and/or other procedure where one or more bones are to be prepared and/or moved to a desired position. For example, the devices and/or techniques may be utilized during an osteotomy procedure in which one bone (e.g., a metatarsal) is cut into a first bone portion and a second bone portion. Accordingly, reference to a metatarsal and an opposed cuneiform herein may be replaced with other bone pairs as described herein.

Further, while the techniques and devices described herein are generally discussed in connection with preparation and fusion of the second and/or third TMT joints, the devices and techniques are not limited to these specific anatomical locations or being performed together. In various examples, devices and/or techniques of the disclosure may be utilized to prepare and promote fusion across a single TMT joint (e.g., the first TMT joint the second TMT joint, the third TMT joint, the fourth TMT joint, the fifth TMT joint) and/or any combination of TMT joints (e.g., the first and second TMT joints; the second and third TMT joints; the first and third TMT joints; the first, second, and third TMT joints; the first and fourth TMT joints; the first, second, and fourth TMT joints, etc.).

To further understand example techniques of the disclosure, the anatomy of the foot will first be described with respect to FIGS. 1-3 along with example misalignments that may occur and be corrected according to the present disclosure. As noted, a bone misalignment may be caused by metatarsus adductus, hallux valgus (bunion), arthritis, and/or other condition. The condition may present with a misalignment of one or more bones in the foot.

Figure 1A:
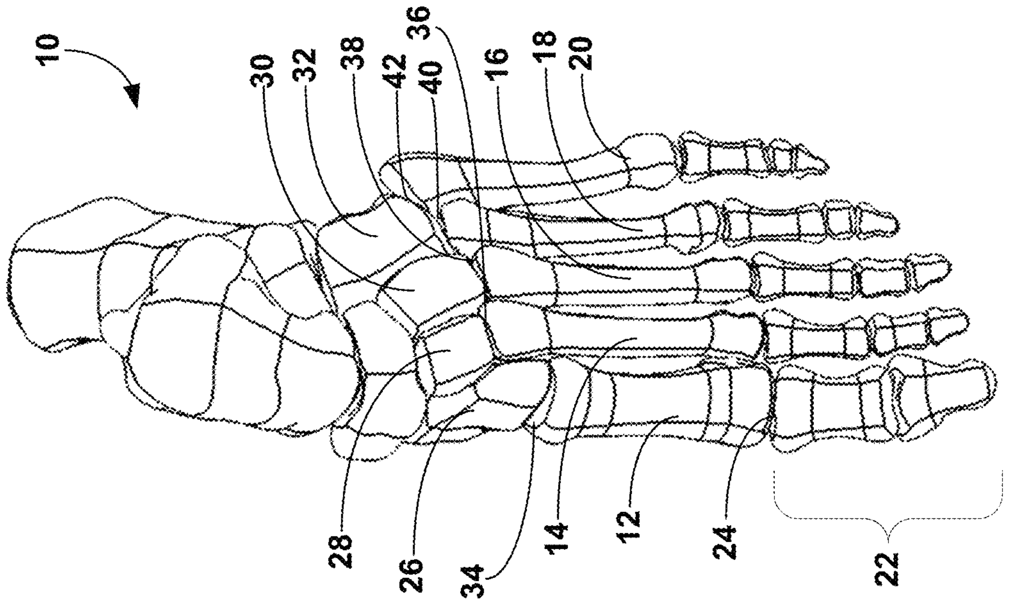

FIGS. 1A and 1B are top and front views, respectively, of a foot 10 showing normal metatarsal alignment positions. Foot 10 is composed of multiple bones including a first metatarsal 12, a second metatarsal 14, a third metatarsal 16, a fourth metatarsal 18, and a fifth metatarsal 20. First metatarsal 12 is on a medial-most side of the foot while fifth metatarsal 20 is on a lateral-most side of the foot. The metatarsals are connected distally to phalanges 22 and, more particularly, each to a respective proximal phalanx. The joint 24 between a metatarsal and a corresponding opposed proximal phalanx is referred to as a metatarsophalangeal ("MTP") joint. The first MTP joint is labeled as joint 24 in FIG. 1A, although second, third, fourth, and fifth MTP joints are also illustrated in series adjacent to the first MTP joint.

The first metatarsal 12 is connected proximally to a medial cuneiform 26, while the second metatarsal 14 is connected proximally to an intermediate cuneiform 28, and the third metatarsal 16 is connected proximally to lateral cuneiform 30. The fourth and fifth metatarsals 18, 20 are connected proximally to the cuboid bone 32. The joint between a metatarsal and opposed bone (cuneiform, cuboid) is referred to as the tarsometatarsal ("TMT") joint. FIG. 1A designates a first TMT joint 34, a second TMT joint 36, a third TMT joint 38, a fourth TMT joint 40, and a fifth TMT joint 42. The angle between adjacent metatarsals is referred to as the intermetatarsal angle ("IMA").

In the example of FIGS. 1A and 1B, foot 10 is illustrates as having generally normally aligned metatarsals. Normal metatarsal alignment may be characterized, among other attributes, by a low intermetatarsal angle (e.g., 9 degrees or less, such as 5 degrees or less) between the first metatarsal and the second metatarsal. In addition, the lesser metatarsals may be generally parallel to a longitudinal axis bisecting the foot proximally to distally.

Figure 3A:
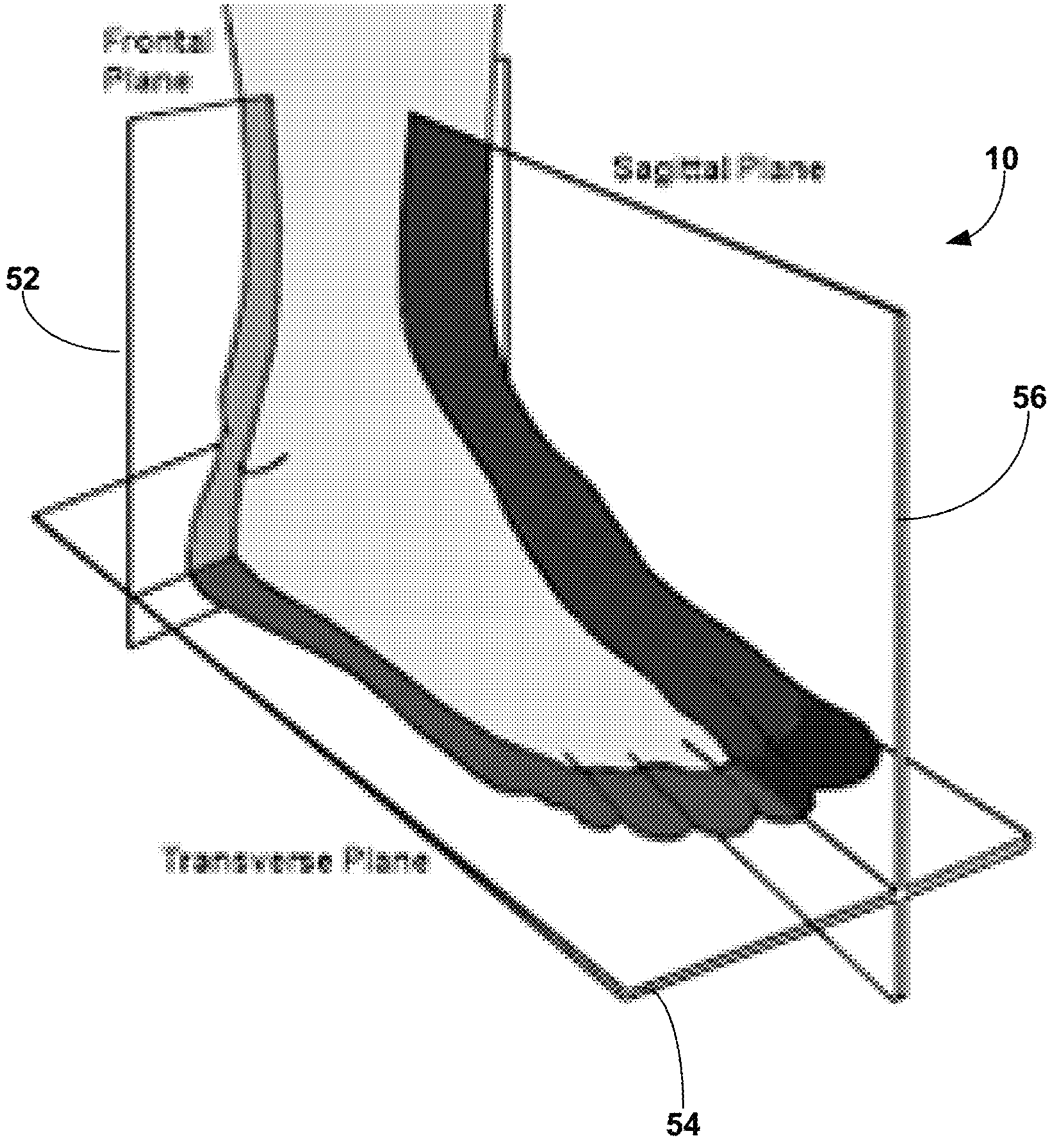
FIG. 3A illustrates the different anatomical planes of a foot.

FIG. 3A illustrates the different anatomical planes of foot 10, including frontal plane 52, transverse plane 54, and sagittal plane 56. The frontal plane 52, which is also known as the coronal plane, is generally considered any vertical plane that divides the body into anterior and posterior sections. On foot 10, the frontal plane 52 is a plane that extends vertically and is perpendicular to an axis extending proximally to distally along the length of the foot. The transverse plane 54, which is also known as the horizontal plane, axial plane, or transaxial plane, is considered any plane that divides the body into superior and inferior parts. On foot 10, the transverse plane 54 is a plane that extends horizontally and is perpendicular to an axis extending dorsally to plantarly (top to bottom) across the foot. Further, the sagittal plane 56 is a plane parallel to the sagittal suture which divides the body into right and left halves. On foot 10, the sagittal plane 56 is a plane that extends vertically and intersects an axis extending proximally to distally along the length of the foot.

Figure 2B:
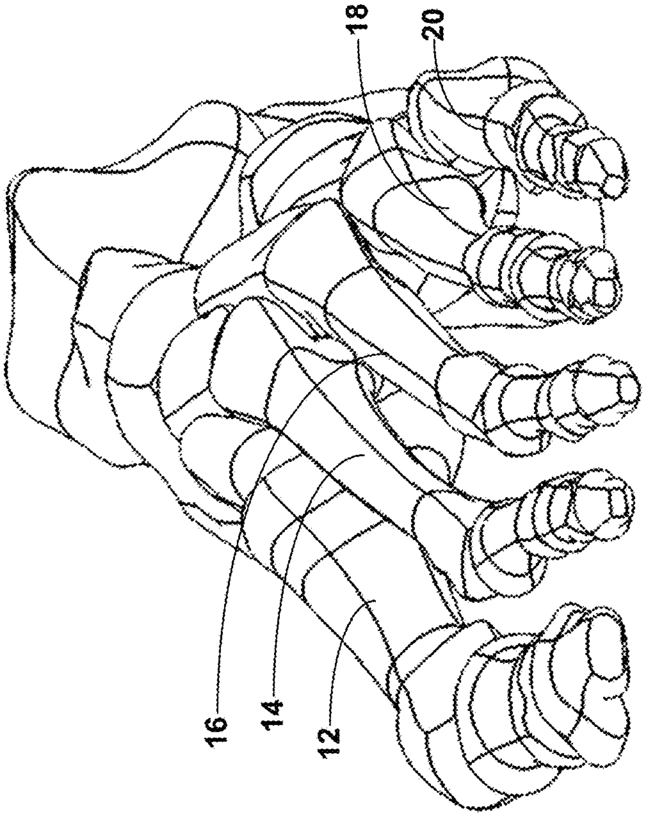
FIGS. 2A and 2B are top and front views, respectively, of a foot showing an example metatarsal adductus bone misalignment.
Figure 2A:
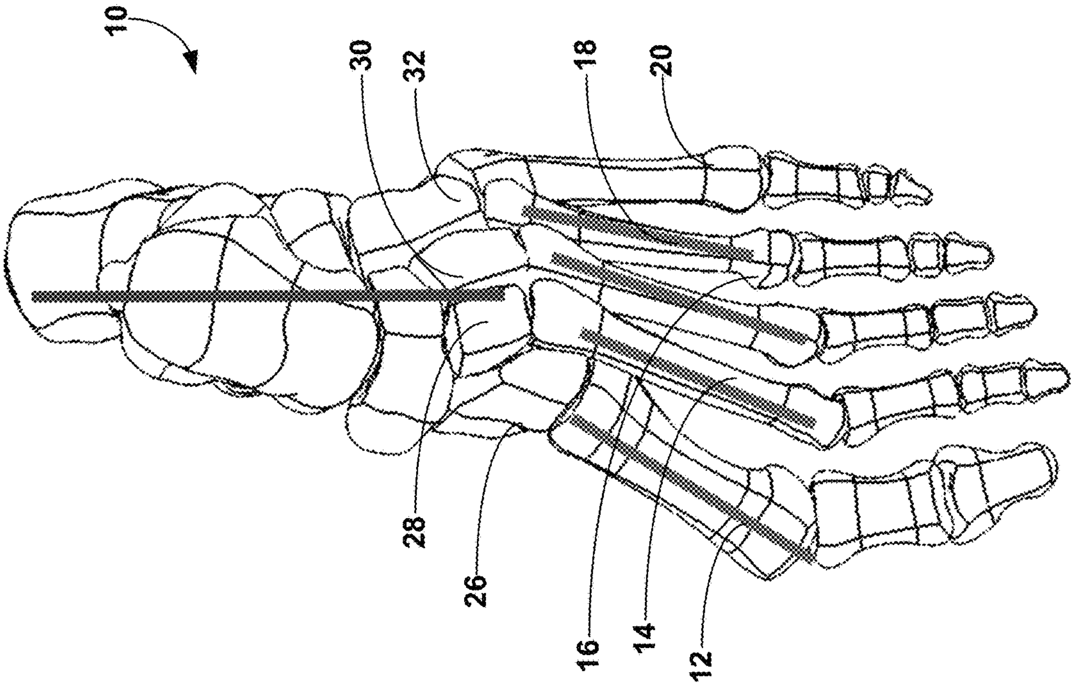
Figure 3B:
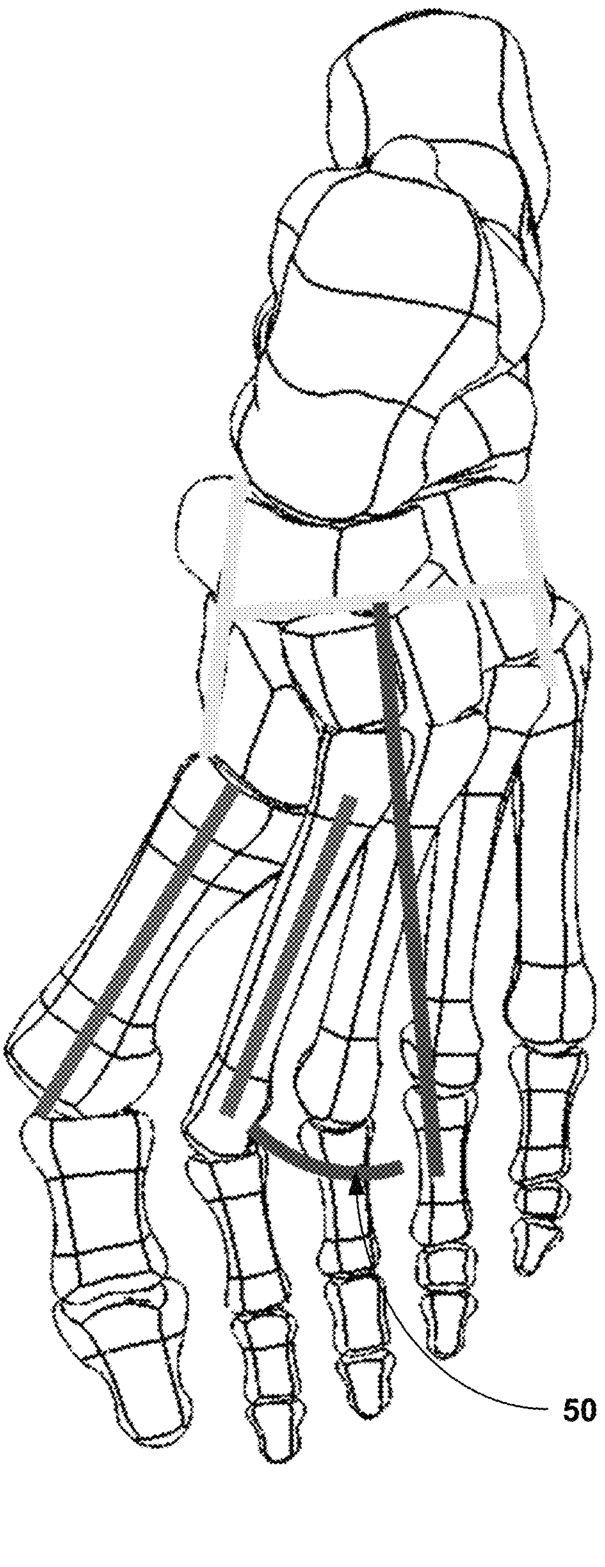
FIG. 3B illustrates the metatarsus adductus of the foot from FIGS. 2A and 2B characterized by a metatarsus adductus angle.

For patients afflicted with metatarsal adductus, at least one or more of the lesser metatarsals (the second through fifth metatarsals) may be deviated medially in the transverse plane (e.g., in addition to or in lieu of being rotated in the frontal plane and/or being deviated in the sagittal plane relative to clinically defined normal anatomical alignment for a standard patient population). FIGS. 2A and 2B are top and front views, respectively, of foot 10 showing an example metatarsal adductus bone misalignment. As shown in this example, the metatarsals are deviated medially relative to an axis bisecting the foot. This can result in an abnormal biomechanical structure benefiting from surgical intervention. FIG. 3B illustrates the metatarsus adductus of foot 10 from FIGS. 2A and 2B being characterized by a metatarsus adductus angle 50.

Figure 4:
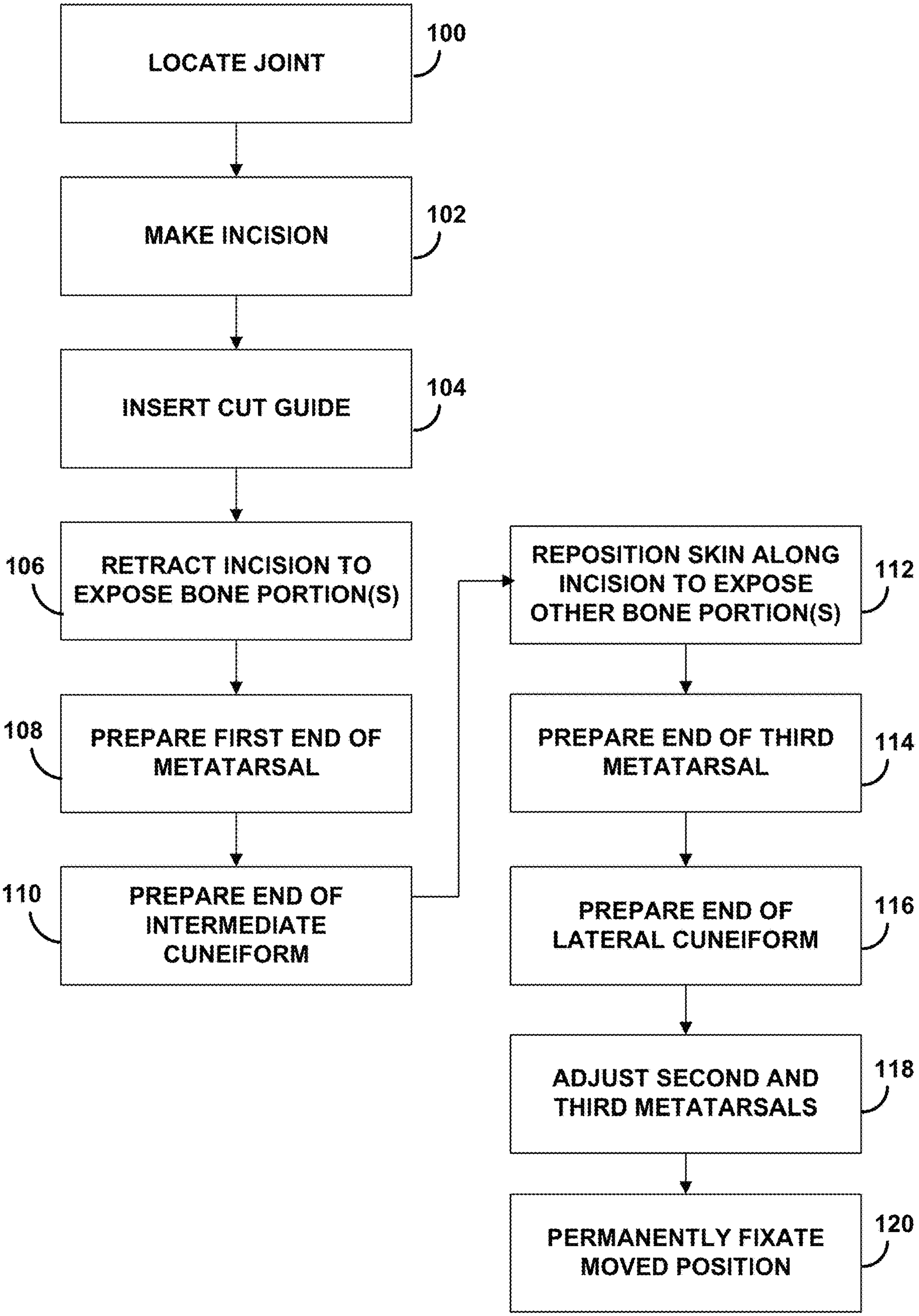
FIG. 4 is a flow diagram illustrating an example technique for preparing TMT joints for fusion and realigning multiple metatarsals to less invasively treat a metatarsus adductus deformity.

Bone positioning techniques and instruments can be useful to correct a misalignment of one or more bones, such as a metatarsal adductus and/or hallux valgus metatarsal misalignment, and/or to promote fusion across a joint (e.g., such as an arthritis joint fusion procedure). FIG. 4 is a flow diagram illustrating an example less invasive technique for preparing TMT joints for fusion and realigning one or more (e.g., multiple) metatarsals to treat at least a metatarsus adductus deformity. The technique will be described with respect to the bone numbering introduced with respect to FIGS. 1A and 1B, although may be performed on other bones. For purposes of discussion, the technique of FIG. 4 will be discussed with respect to different example images, although may be performed without such instrumentation or with different instrumentation, as discussed herein.

Figure 6A:
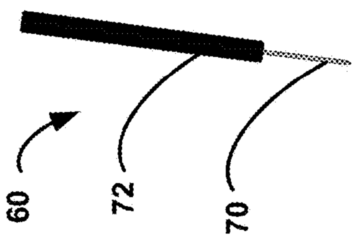
FIGS. 6A and 6B illustrate an example joint locator pin that may be used to help locate a joint and position an incision guide.
Figure 6B:
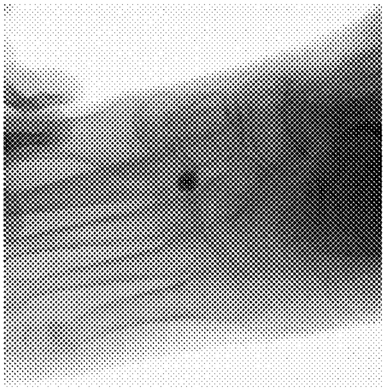

With reference to FIG. 4, the example technique includes locating a joint, such as, the second TMT and third TMT joints (100). As shown in FIGS. 6A and 6B, in connection with locating a joint, a pin 60 may be inserted percutaneously through the skin of the patient at a target location, such as into an underlying TMT joint (e.g., into the second TMT, into third TMT joint) and/or into a space between the second TMT and third TMT joints (e.g., between the second and third metatarsals and/or between the intermediate and lateral cuneiforms). The pin 60 may have a comparatively smaller distal portion 70 insertable percutaneously into the TMT joint and a comparatively larger proximal portion 72. Larger proximal portion 72 may have a cross-sectional width (e.g., diameter) at least 50% bigger than distal portion 70. In use, a clinician can insert distal portion 70 through the skin of the patient and into an underlying joint space. The clinician can view the location of pin 60 relative to the patient's anatomy before, during, and/or after insertion fluoroscopically (e.g., as shown in FIG. 6B). The clinician can insert pin 60 into a TMT joint and/or check that the pin 60 is in the correct location with the aid of fluoroscopic examination.

Figure 7A:
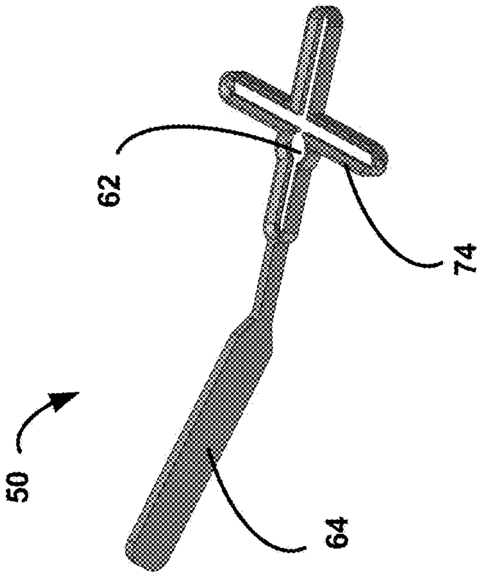
FIGS. 7A and 7D illustrate example incision guides that may be used to help set the size and/or location of an incision prior to making the incision.
Figure 7B:
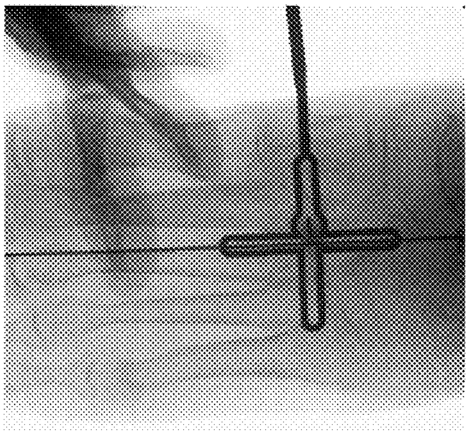

To surgically access at least the second TMT and third TMT joints a clinician can make an incision (102), optionally with the aid of an incision guide (e.g., as shown in FIGS. 7A and 7B). The example incision guide 50 can include a guide surface (e.g., a pair of guide surfaces defining a channel 74 therebetween) that is connected to a pin receiving hole 62. Pin receiving hole 62 is illustrated in the example of FIGS. 7A and 7B as being parallel to (e.g., co-linear with) handle 64 of the incision guide. The clinician can orient incision guide 50 relative to pin 60 by positioning the pin in pin receiving hole 62, e.g., by sliding guide 50 over pin 60. By using pin 60 and incision guide 50 as references, the clinician can accurately control the location of the incision in relation to the joints that are to be accessed and the length of the incision.

In various implementations, whether using guide 50, a different guide, or making an incision without the aid of a guide, the clinician can control the length of the incision to be less than or equal to 4.5 cm, such as less than or equal to 4.0 mm. For example, in some embodiments the incision may be approximately 4 cm in length. The length of the incision may be set by the length of the guide surface (e.g., channel 74) of guide 50. The incision may be orientated generally parallel to the long axis of the second metatarsal and/or third metatarsal (extending in a generally proximal to distal direction). In some examples, the incision may be substantially centered in a proximal to distal direction at the second and/or third TMT joints. Additionally or alternatively, the incision may be substantially centered in a medial to lateral direction between the second and/or third TMT joints.

Figure 7D:
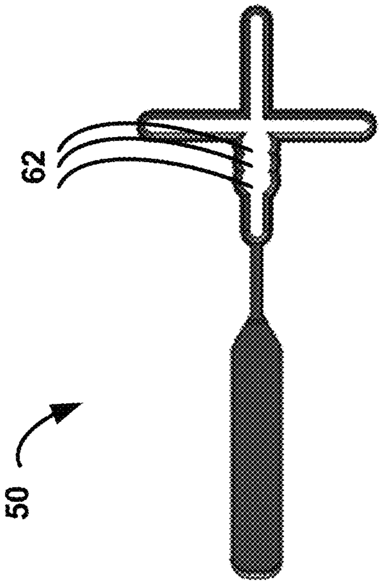
Figure 7C:
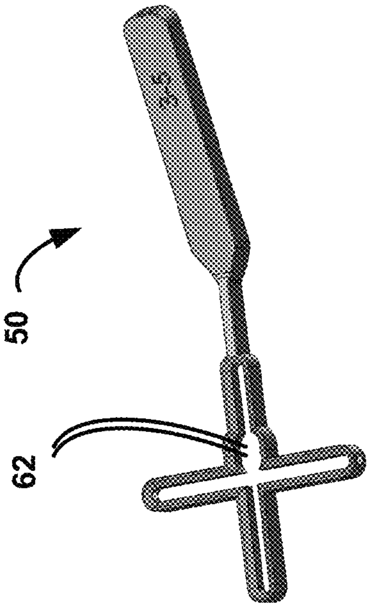

While incision guide 50 shown at FIG. 7A has only one pin receiving hole 62, in other examples, the incision guide may have two pin receiving holes (as shown in FIG. 7C), three receiving holes (as shown in FIG. 7D), or more pin receiving holes. The different pin receiving holes may be positions relative to the guide surface (e.g., channel 74) of guide 50 to enable some flexibility as to the location of the skin incision 102. In either case, once guide 50 is suitably positioned, the clinician can may an incision through the skin of the patient by guiding a cutting instrument along a guide surface of the guide. The clinician may remove pin 60 before and/or while making the incision to extend the incision through the space occupied by the pin.

Figure 5:
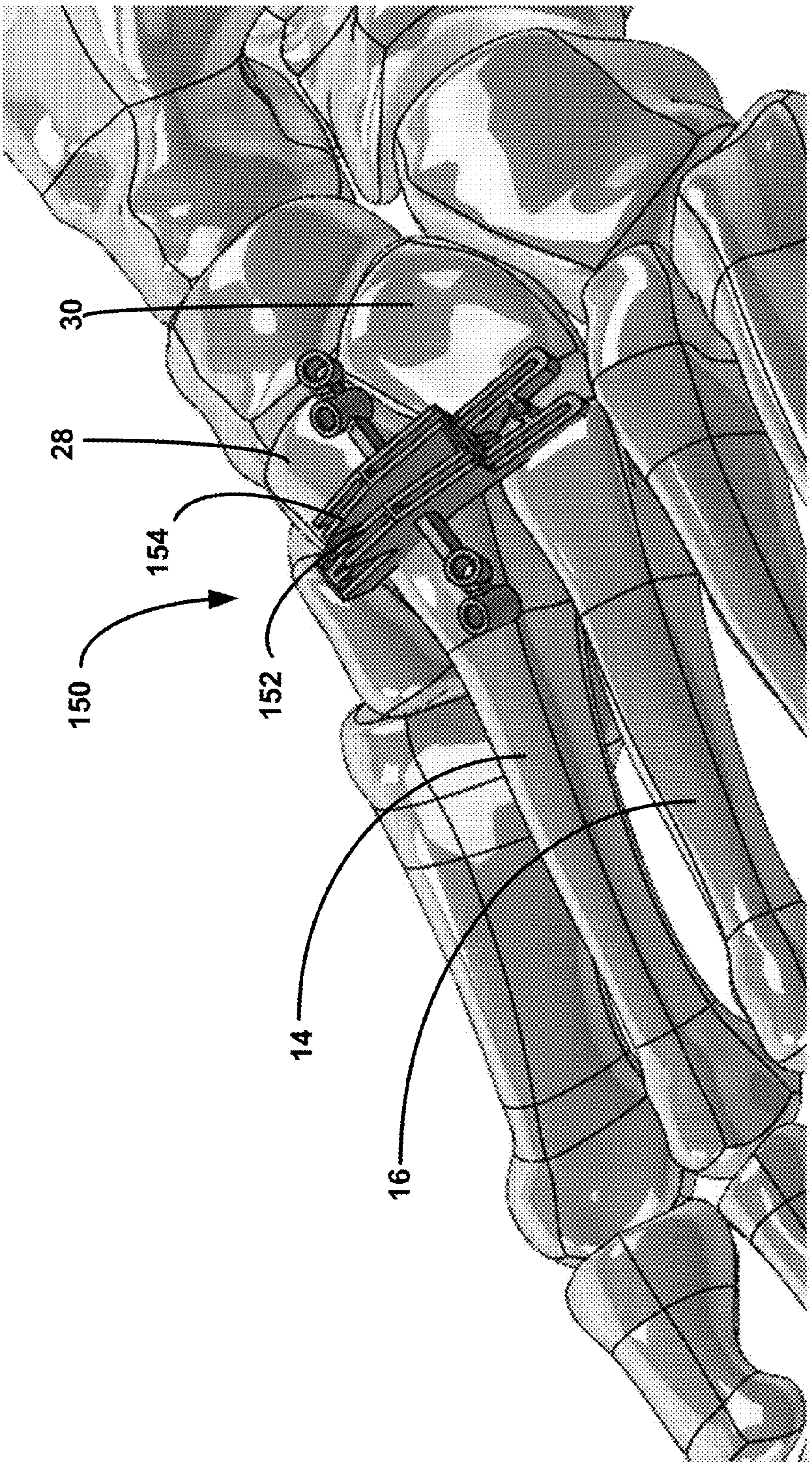
FIG. 5 is a top view of a foot showing an example cut guide positioned over the second and third TMT joints during joint preparation.
Figure 8:
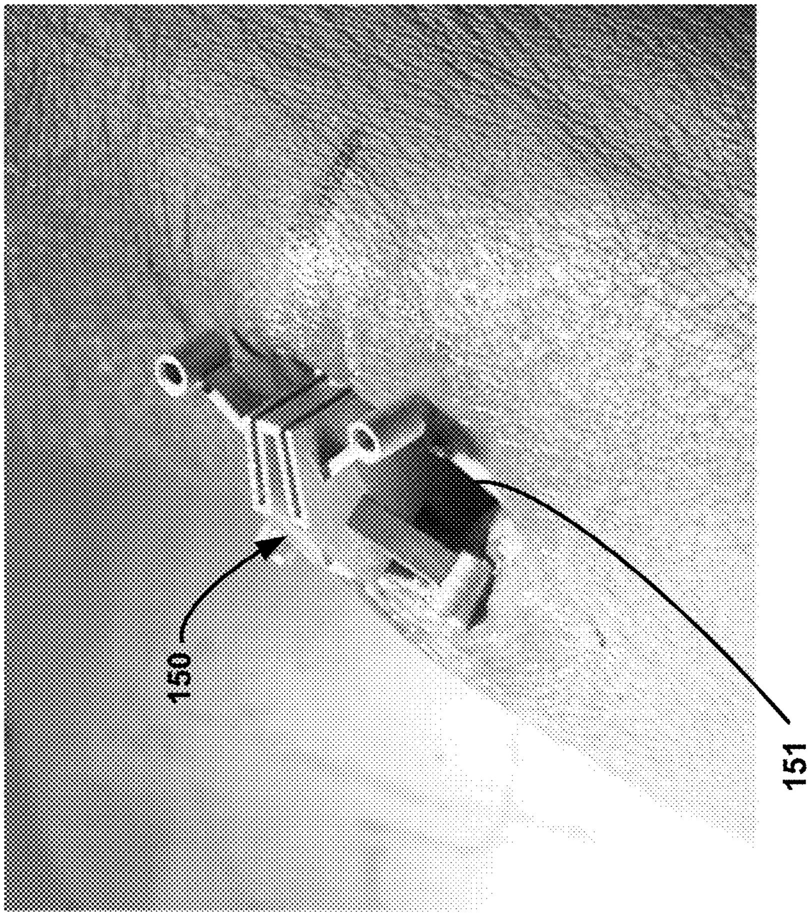
FIG. 8 illustrates an example bone cutting guide positioned through an incision.

The example technique of FIG. 4 also involves inserting a cut guide through the incision in the skin of the patient. For example, as shown in FIGS. 5 and 8, a cut guide 150 may be inserted through the incision 151 in the skin of the patient and positioned over the second and third TMT joints. In the illustrated example, cut guide 150 is shown defining a first guide surface 152 (which is illustrated as a cutting slot) positioned over a portion of a second metatarsal 14 and a portion of a third metatarsal 16 to be cut. Cut guide 150 is also shown as defining a second guide surface 154 (which is illustrated as a cutting slot) positioned over a portion of an intermediate cuneiform 28 and a lateral cuneiform 30 to be cut.

Optionally, the cut guide may be temporarily fixated through the use of pins. After insertion of the cut guide 150, the incision can be retracted to expose a joint/bone (106) as shown in FIG. 9A. A first end of the second metatarsal (108) and an end of the intermediate cuneiform (110) may be prepared, for example, by inserting a cutting instrument through the corresponding cut guide channels. At (112) the skin may be repositioned along the incision to expose an end of a third metatarsal and an end of the lateral cuneiform, for example, to allow subsequent preparation of the end of the third metatarsal (114) and the lateral cuneiform (116) without having to increase the size of the incision. While FIG. 4 illustrates an example technique order in which the bones forming the second tarsometatarsal joint are prepared before the bones forming the third tarsometatarsal joint, the order may be reversed, and any bone or combination of bone pairs may be prepared (e.g., cut) before or after any other bone or combination of bone pairs without departing from the scope of the disclosure.

Figure 11:
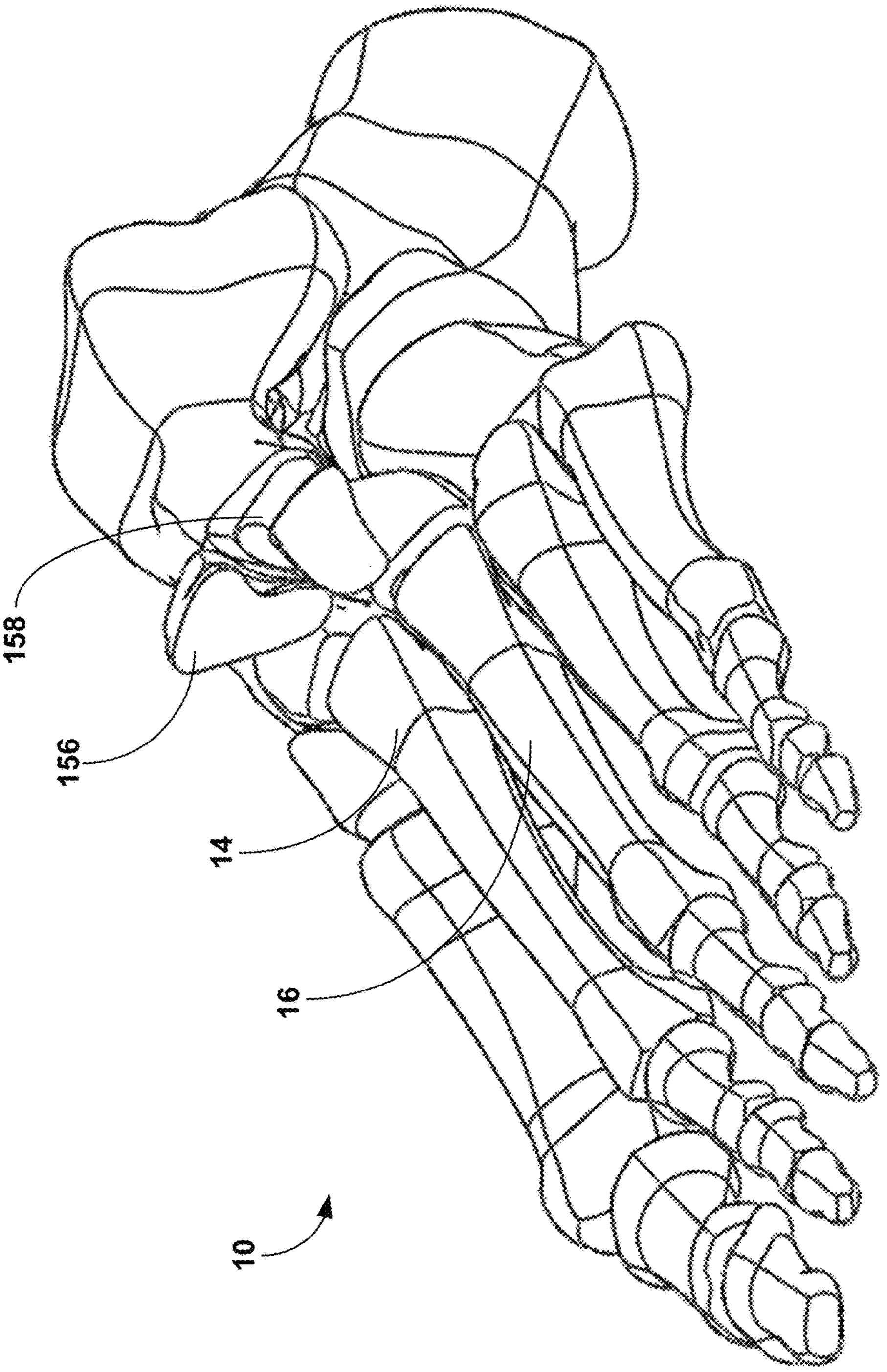
FIG. 11-14 illustrates exemplary bone wedge removal, realignment, and fixation steps that may be implemented in accordance to some aspects of the disclosure.
Figure 12:
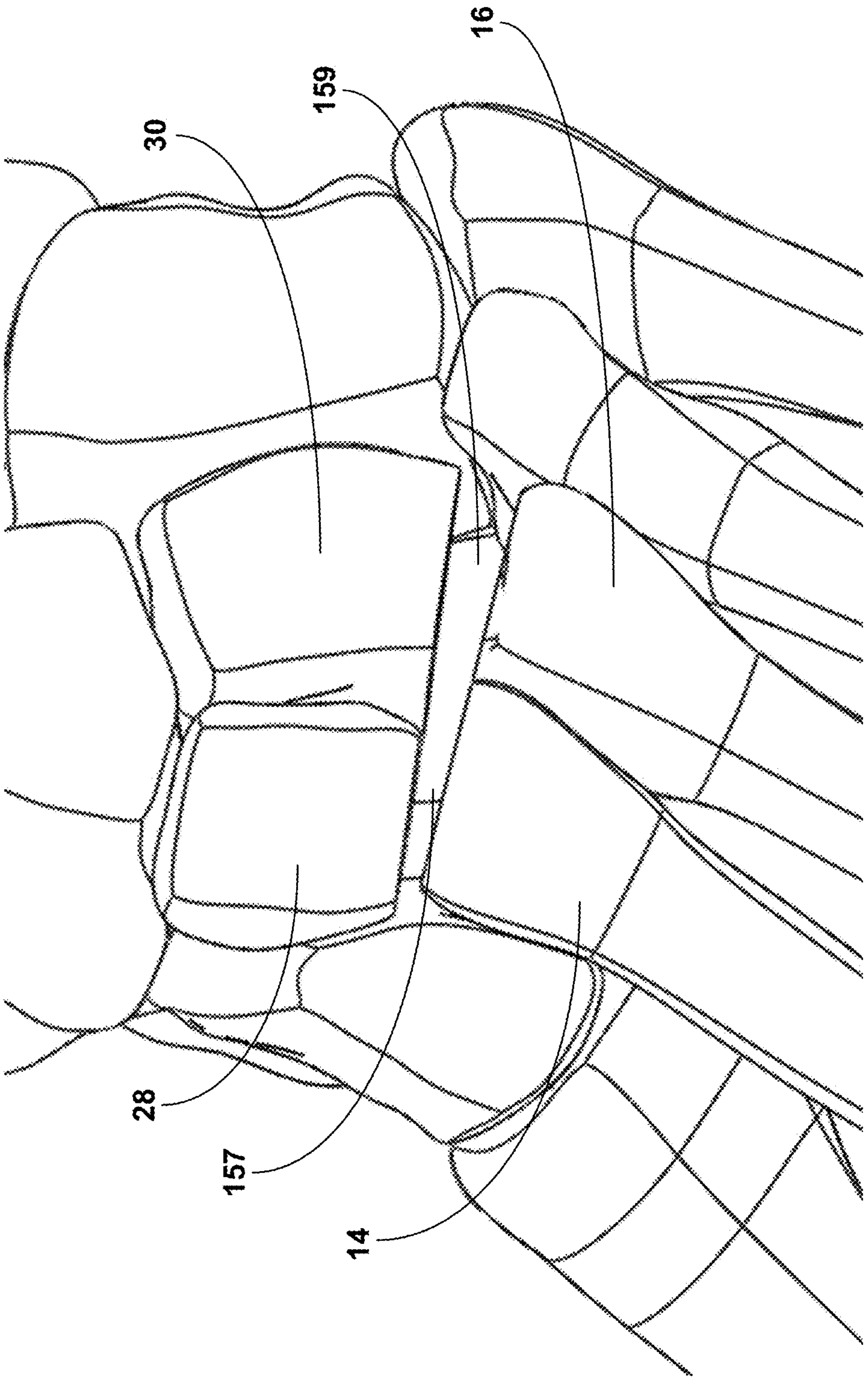
Figure 13:
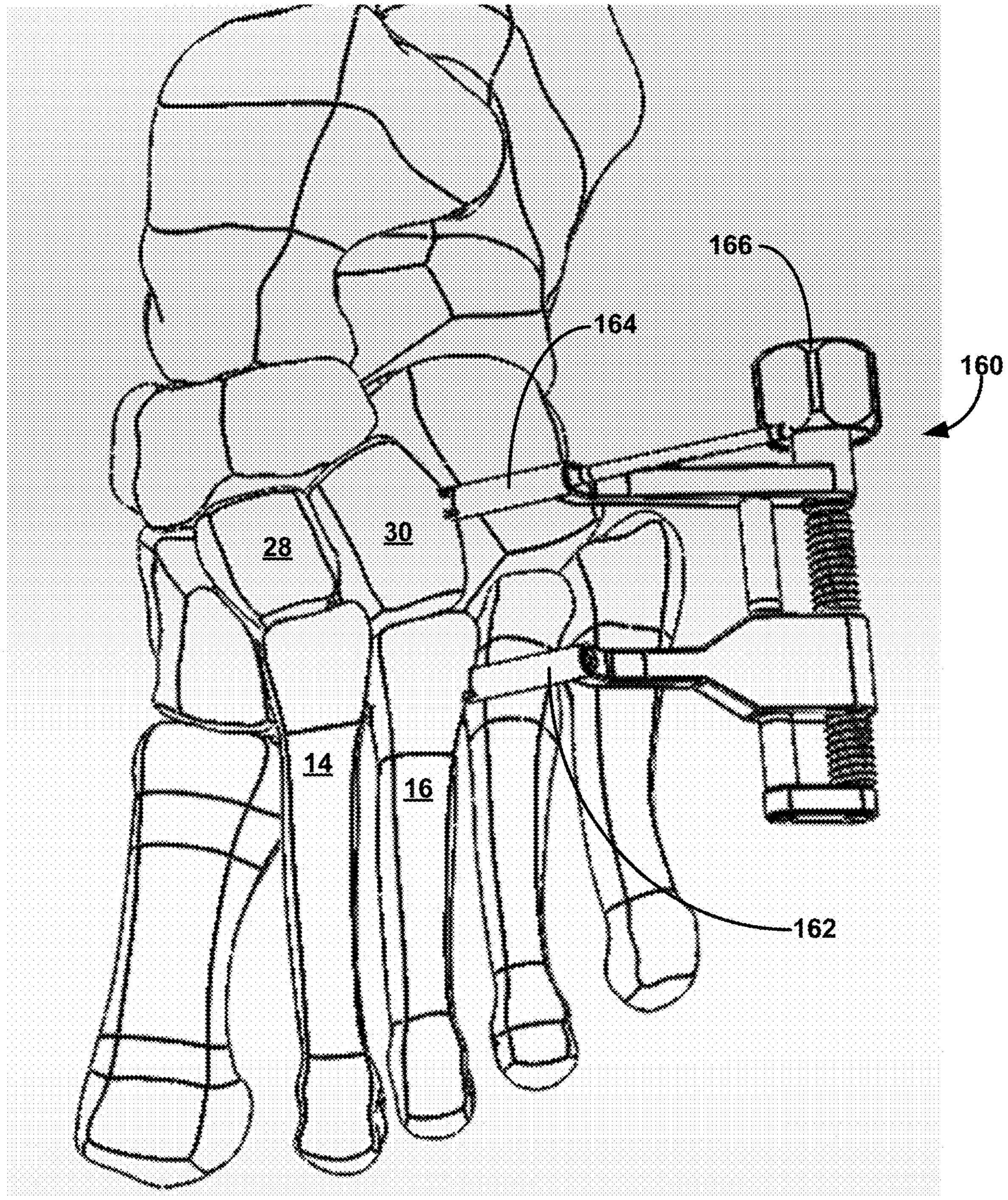

As shown in FIG. 11, a bone wedge corresponding to the sections cut using the guide may be removed (in one or more pieces) to enable adjustment of the second and third metatarsal (118). Adjustment may include the use of a compressor 160, as shown in FIG. 13 and described, for example, in U.S. Pat. No. 9,622,805, issued Apr. 18, 2017 and entitled "BONE POSITIONING AND PREPARING GUIDE SYSTEMS AND METHODS." Once the position of the second and third metatarsal has been corrected, the clinician may fixate (120) through the use of a bone plate 1400, for example. Other bone connectors, such as, a staple, a screw and such may be alternatively or additionally be used.

In general, the clinician can prepare the end of each bone forming a TMT joint so as to promote fusion of the bone ends across the TMT joint following realignment. Bone preparation may involve using a tissue removing instrument, which may also be referred to as a cutting instrument, to apply a force to the end face of the bone so as to create a bleeding bone face to promote subsequent fusion. Example tissue removing instruments that can be used include, but are not limited to, a saw, a rotary bur, a rongeur, a reamer, an osteotome, a curette, and the like. The tissue removing instrument can be applied to the end face of the bone being prepared to remove cartilage and/or bone. For example, the tissue removing instrument may be applied to the end face to remove cartilage (e.g., all cartilage) down to subchondral bone. Additionally or alternatively, the tissue removing instrument may be applied to cut, fenestrate, morselize, and/or otherwise reshape the end face of the bone and/or form a bleeding bone face to promote fusion. In instances where a cutting operation is performed to remove an end portion of a bone, the cutting may be performed frechand, with the aid of a cutting guide having a guide surface positionable over the portion of bone to be cut, and/or with the aid of a bone preparation template. When using a cutting guide, a cutting instrument can be inserted against the guide surface (e.g., between a slot defined between two guide surfaces) to guide the cutting instrument for bone removal.

In some examples, the clinician cuts at least one bone defining the second TMT joint (e.g., one or both of second metatarsal 14 and intermediate cuneiform 28) and also cuts at least one bone defining the third TMT joint (e.g., one or both of third metatarsal 16 and the lateral cuneiform 30). The clinician may cut both bones defining the second TMT joint or may cut only one bone defining the joint and perform a different preparation technique on the other bone. Similarly, the clinician may cut both bones defining the third TMT joint or may cut only one bone defining the joint and perform a different preparation technique on the other bone.

Where the clinician cuts at least one bone forming a TMT joint, each such cut may be parallel or non-parallel to the end of the bone being cut in one or more of the frontal, transverse, and sagittal planes. For example, the cut may be angled in the transverse plane relative to the end face of the bone and parallel to the end face of the bone in the frontal plane. As other examples, the cut may be curved, arced, spherical, zig-zag, or may define other desired cut shape to facilitate realignment and fusion of one bone relative to another bone portion. In some examples, the end faces of the two bones defining the TMT joint are each prepared by cutting an end portion of each bone to create a shaped opening between the end faces. The opening may have a shape that allows the bones to be repositioned relative to each other (e.g., partially or fully closing the opening created in the process of realignment) to facilitate realignment and subsequent fusion.

FIG. 5 is a top view of foot 10 showing an example cut guide 150 positioned over the second and third TMT joints. Cut guide 150 can be used to guide a cutting instrument to prepare the second TMT joint (e.g., one or both of second metatarsal 14 and intermediate cuneiform 28) and the third TMT joint (e.g., one or both of third metatarsal 16 and the lateral cuneiform 30). In the example of FIG. 5, cut guide 150 is shown defining a first guide surface 152 (which is illustrated as a cutting slot) positioned over a portion of a second metatarsal 14 and a portion of a third metatarsal 16 to be cut. Cut guide 150 is also shown as defining a second guide surface 154 (which is illustrated as a cutting slot) positioned over a portion of an intermediate cuneiform 28 and a lateral cuneiform 30 to be cut. The clinician can advance a cutting instrument parallel to first guide surface 152 to cut an end of second metatarsal 14 and also to cut an end of third metatarsal 16. The clinician can also advance the cutting instrument parallel to second guide surface 154 to cut an end of intermediate cuneiform 28 and lateral cuneiform 30. In different implementations, a guide surface of cut guide 150 may be linear, curved, and/or define yet other shapes. According, the step of guiding a cutting instrument parallel to the guide surface may result in a linear cut, a curved cut, or yet other shaped cut across the bone.

In the example of FIG. 5, first guide surface 152 is illustrated as being angled in the transverse plane across the second and third metatarsals 14, 16. The first guide surface 152 is illustrated as being angled from a medial-proximal side of second metatarsal 14 toward a lateral-distal side of third metatarsal 16. The lateral-distal side of third metatarsal 16 may still be on the proximal half of the metatarsal, albeit comparatively distal to the proximal location on the second metatarsal. By preforming an angled cut relative to the end faces of the bones being cut, a wedge-shaped bone portion may be released from the bone. For example, as shown in FIG. 11, a wedge-shaped section 156 of second metatarsal 14 is released upon cutting the second metatarsal. Further, a wedge-shaped section 158 of third metatarsal 16 is released upon cutting the third metatarsal. Each wedge-shaped section of bone removed via cutting may have a narrow width (e.g., apex) on a medial side of the bone being cut and a wider width (e.g., base) on a lateral side of the bone being cut. The degree of angulation in the specific dimensions of the bone wedge formed during cutting may vary depending on the anatomy of the patient and the extent of the deformity being corrected. In either case, the bone wedges so cut can be removed from the TMT joint spaces to define a wedge-shaped opening relative to an opposed bone.

In the example of FIG. 5, the clinician can use second guide surface 154 to guide the cutting instrument to cut an end of intermediate cuneiform 28 and lateral cuneiform 30 to promote fusion following realignment of the metatarsals. The cuts performed on the intermediate cuneiform 28 and lateral cuneiform 30 may be generally parallel to the end face of a bone being cut (e.g., in the transverse plane) or may be angled relative to an end face of the bone being cut. In still other examples, the end faces of one or both of intermediate cuneiform 28 and lateral cuneiform 30 may not be cut but may be prepared using a different technique as discussed above (e.g., fenestrated).

In some examples in which the second metatarsal 14 and the third metatarsal 16 are prepared by cutting, the metatarsals may be cut using a single continuous cut across both metatarsals. For example, the clinician may guide a cutting instrument linearly from a medial side of the second metatarsal 14 toward the lateral side of the third metatarsal 16 or from the lateral side of the third metatarsal to the medial side of the second metatarsal. In either case, the clinician may form a continuous cut line transecting the ends of the second and third metatarsals. Such a continuous cut across the bases of the second and third metatarsals may be useful to promote reliable reduction of the metatarsus adductus angle during subsequent bone realignment. In applications where the intermediate cuneiform 28 and the lateral cuneiform 30 are cut in addition to or in lieu of the ends of the metatarsals, the two cuneiforms may or may not be cut using such a continuous cut across the ends of the two metatarsals.

In other applications of the surgical technique, the ends of the second metatarsal 14 and third metatarsal 16 may be cut independently (e.g., without moving the cutting instrument in a continuous cutting line across the two metatarsals). For example, when the patient exhibits a significant step off (e.g., distal offset) between the end of the intermediate cuneiform 28 and the end of the lateral cuneiform 30, the ends of the opposed second and third metatarsals 14, 16 may be prepared independently (e.g., through two separate cuts) in lieu of forming a continuous cut across the ends of the two metatarsals. The ends of the opposed second and third metatarsals 14, 16 may be prepared independently for other reasons as well, such as to provide independent control/adjustability over the cut angles on the second and third metatarsals.

In instances where the clinician cuts the end face of the bone, the clinician may or may not perform one or more additional preparation steps on the end face prior to or after cutting the end face. In some examples, the clinician fenestrates the newly-formed end face of the bone after cutting the bone. The clinician may use a drill to fenestrate the end newly-formed end face of the bone being cut, which can help promote subsequent fusion of the bone following realignment. The clinician may fenestrate a bone face by making multiple openings (e.g., drill holes) in the bone face, providing multiple bleeding points in the end of the bone face. Each drill hole may be comparatively small relative to the cross-sectional area of the end face, such as less than 10% of the cross-sectional area of the end face, less than 5% of the cross-sectional area of the end face, or less than 1% of the cross-sectional area of the end face. The multiple openings can be arrayed at different locations across the end face to provide locations for promoting fusion across the end face. The number of holes formed during fenestration may vary and, in some examples, is greater than 5, such as greater than 10.

With further reference to FIG. 4, the example technique involves moving the second metatarsal 14 and the third metatarsal 16 in at least one plane (118). While FIG. 4 schematically illustrates an example order in which the second and third metatarsals 14, 16 are moved after preparing the end faces of metatarsals 14, 16 and opposed intermediate and lateral cuneiforms 28, 30, other orders of bone preparation and movement may be performed. For example, the clinician can move the second and/or third metatarsals 14, 16 before preparing one or more metatarsals and/or one or more cuneiforms (e.g., before preparing the end faces of all of the bones). For instance, the clinician may move the second and third metatarsals 14, 16 and then prepare the end faces of metatarsals 14, 16 and opposed intermediate and lateral cuneiforms 28, 30. In these implementations, the clinician may or may not further move the second and/or third metatarsals 14, 16 after preparing the end faces of the metatarsals and cuneiforms. As another example, the clinician may prepare the end face of one or more bones (e.g., one or more metatarsals and/or cuneiforms), move one or both of second metatarsal 14 and third metatarsal 16, and then prepare the end face of one or more other bones (e.g., one or more metatarsals and/or cuneiforms).

Independent of the order of movement and bone preparation, the clinician may move the second and third metatarsals 14, 16 in one or more planes, such as the transverse plane, e.g., by pivoting the metatarsals about their proximal ends, causing a distal end of the metatarsals to move laterally in the transverse plane. In instances where a wedge-shaped opening was formed at the second and/or third TMT joints during bone preparation, lateral rotation of the distal ends of the second and third metatarsals may close the wedge-shaped opening(s) (or close another shaped opening, in instances in which a non-wedge-shaped opening was created). For example, translation of the distal ends of the second and third metatarsals 14, 16 laterally in the transverse plane may bring the ends of the second metatarsal 14 and opposed intermediate cuneiform 28 as well as the ends of the third metatarsal 16 and opposed lateral cuneiform 30 in generally parallel alignment. The clinician may move the second and/or third metatarsal in the frontal plane and/or sagittal plane in addition to or in lieu of moving one or both bones in the transverse plane. For example, the clinician may rotate one or both bones in the frontal plane and/or translate one or both bones (e.g., dorsally) in the sagittal plane.

In general, movement of second metatarsal 14 and third metatarsal 16 in the transverse plane can close the metatarsus adductus angle. The metatarsus adductus angle may be the angular measurement formed between the line bisecting the second metatarsal and the longitudinal line bisecting the lesser tarsus on a dorsoplantar radiograph. In some examples, the second and third metatarsals 14, 16 are moved until the metatarsus adductus angle for each metatarsal is 15° or less, such as 12° or less, 10° or less, 7° or less, 5° or less, or 3° or less.

The second metatarsal 14 and third metatarsal 16 may be moved individually or jointly (e.g., as a bone block). Moving the second and third metatarsals 14, 16 as a joined group may be helpful to achieve a more natural realignment of the metatarsals and correction of the metatarsus adductus deformity. To help move the second and third metatarsals 14, 16 as a joined group, the ligaments between the two metatarsals may be preserved during preparation of the second and third TMT joints. For example, the plantar TMT ligaments and ligaments between the second and third metatarsals 14, 16 may be preserved (e.g., remain uncut or unbroken) during preparation and movement of the second and third metatarsals. Preserving the ligament structure can help avoid destabilization of the second and third TMT joints during deformity reduction, which may improve the anatomical realignment of the bone structure.

To move the second and third metatarsals 14, 16, either alone or in combination, the bones may be pivoted about their proximal base, causing the distal ends of the bones to translate laterally in the transverse plane. When moving the second and third metatarsals 14, 16 as a group, the clinician may pivot the second and third metatarsal bone block about the proximal medial portion of second metatarsal 14. The clinician may move the second and third metatarsals 14, 16 as a combined group in the transverse plane, with or without simultaneously rotating both bones in the frontal plane and/or adjusting the sagittal plane position of the bones. In some implementations, the clinician moves the second and third metatarsals 14, 16 as a group about the Lisfranc ligament while the second metatarsal remains attached to the Lisfranc ligament. Accordingly, the Lisfranc ligament may act as a hinge or pivot point about which the second and third metatarsal bone group can rotate in the transverse plane.

In other examples, the clinician may substantially independently move the second and third metatarsals 14, 16 (e.g., by applying a separate movement force to each metatarsal). For example, the clinician may apply a force to move third metatarsal 16 in one or more planes and subsequently apply a force to move the second metatarsal 14 in one or more planes (or, instead, move the second metatarsal 14 followed by the third metatarsal), such as in two or more, or all three planes. The clinician may or may not cut or otherwise release one or more ligamentous attachments interconnecting the second and third metatarsals 14, 16 to help facilitate independent repositioning of the two bones.

Independent of whether the clinician moves the second and third metatarsals 14, 16 together or independently, the intermetatarsal angle between second and third metatarsals may or may not change during metatarsus adductus correction. In other words, the intermetatarsal angle between second metatarsal 14 and third metatarsal 16 may or may not compress from a pre-corrected intermetatarsal angle to the intermetatarsal angle exhibited after correction. In some implementations, the second and third metatarsals 14, 16 are pivoted as a group within the transverse plane without substantially changing the intermetatarsal angle between the second and third metatarsals. For example, the intermetatarsal angle between the second and third metatarsals may change (e.g., reduce) less than 5°, such as less than 2°, or less than 1° from the angle exhibited before metatarsus adductus correction to the angle exhibited after the correction technique is performed.

To help facilitate movement of the second and third metatarsals in the transverse plane, the clinician may perform a soft tissue release between third metatarsal 16 and fourth metatarsal 18. The soft tissue release may mobilize the third metatarsal relative to the adjacent fourth metatarsal, allowing the joined second-third metatarsal bone block to be pivoted in the transverse plane.

In addition to moving the second metatarsal and the third metatarsal in the transverse plane, the clinician can also move fourth metatarsal 18 and fifth metatarsal 20 in one or more planes (e.g., one or more of the transverse plane, the frontal plane, and the sagittal plane), e.g., to close the metatarsus adductus angle exhibited by those lesser metatarsals. In practice, movement of second metatarsal 14 and third metatarsal 16 in one or more planes (e.g., the transverse plane) may cause the fourth and fifth metatarsals to naturally correct in same one or more planes (e.g., the transverse plane) without requiring separate surgical intervention on the fourth and fifth metatarsals 18, 20. For example, as the clinician rotates the distal end of second metatarsal 14 and third metatarsal 16, either alone or in combination, the distal ends of fourth metatarsal 18 and fifth metatarsal 20 may also move laterally. The proximal base of fourth metatarsal 18 and the proximal base of fifth metatarsal 20 may reorient relative to the cuboid bone 32, closing the metatarsus adductus angle of the fourth and fifth metatarsals. Without wishing to be bound by any particular theory, it is believed that force applied to the second and/or third metatarsal during movement may translate through the tissue and ligament structure interconnecting such metatarsal(s) to the fourth and fifth metatarsals, pulling the lesser metatarsals into realignment.

The position of fourth metatarsal 18 and fifth metatarsal 20 may correct without surgically accessing and preparing the metatarsal (in response to correction of second metatarsal 14 and/or third metatarsal 16). In other applications, however, the clinician may surgically access and prepare the bones defining fourth TMT joint 40 and/or fifth TMT joint 42 in addition to or in lieu of preparing one or more other TMT joints. For example, before or after moving the fourth metatarsal 18 and/or fifth metatarsal 20 in one or more planes (e.g., separate from or in combination with movement of the second metatarsal 14 and/or third metatarsal 16), the clinician can surgically access and prepare the bones defining fourth TMT joint 40 and/or fifth TMT joint 42. The clinician may decide whether to access and prepare the bones defining fourth TMT joint 40 and/or fifth TMT joint 42 depending, for example, on the nature of the deformity being corrected and the perceived need prepare the joints for bone realignment and/or fusion With typical metatarsus adductus deformities, the metatarsals may exhibit a substantially uniplanar misalignment in the transverse plane (although may be misaligned in the frontal plane and/or sagittal plane). For this reason, the example technique of FIG. 4 has generally been described as correcting the second and third metatarsals 14, 16 (and, optionally, fourth and fifth metatarsals 18, 20) in the transverse plane. The clinician may move the metatarsals in only the transverse plane to correct the generally uniplanar misalignment. Alternatively, the clinician may move one or more of the metatarsals being realigned (e.g., multiple or all of the metatarsals been realigned) in more than one plane. For example, in addition to or in lieu of realigning the metatarsal(s) in the transverse plane, the clinician may adjust the rotational angle of the metatarsal(s) in the frontal plane and/or adjust the angle of the metatarsal(s) in the sagittal plane.

Where the clinician performs a multi-planar realignment, the clinician may move one or more metatarsals in multiple planes simultaneously through a single movement, e.g., by moving the metatarsal in an arc or other movement pathway to adjust the position of the metatarsal in multiple planes. The clinician may optionally perform further fine adjustment of the moved position of the one or more metatarsals, e.g., with the aid of a bone positioning device and/or by grasping the metatarsal by hand (e.g., with the aid of a pin inserted into the metatarsal) to finalize the position of the metatarsal prior to fixation.

In other examples, the clinician may perform different movement steps to move the one or more metatarsals in different planes. For example, the clinician may initially move the one or more metatarsals in one or two planes (e.g., transverse plane, frontal plane, sagittal plane) then move the one or more metatarsals in one or two other planes (e.g., the other of the transverse plane, frontal plane, sagittal plane), optionally followed by movement of the one or more metatarsals in a third plane. In other words, the clinician may perform different actions to move the one or more metatarsals in different planes. Each movement step may be performed with the aid of a bone positioning device (which may be the same or different device for different movement steps) and/or by grasping the metatarsal by hand (e.g., with the aid of a pin inserted into the metatarsal).

In some examples, the clinician may move one or more of the metatarsals being realigned (e.g., second metatarsal 14 and/or third metatarsal 16) proximally in the transverse plane toward the opposed bone in addition to or in lieu of moving the metatarsal(s) laterally. For example, the clinician may simultaneously move the metatarsal being realigned (e.g., second metatarsal 14 and/or third metatarsal 16) laterally and proximally in an arc (e.g., parabola) to establish a moved position of one or both metatarsals. As another example, the clinician may move one or more of the metatarsals being realigned (e.g., second metatarsal 14 and/or third metatarsal 16) proximally in the transverse plane toward the opposed bone without moving the one or more of the metatarsals in any other planes. For example, during an arthritic joint fusion procedure, the clinician may prepare the end face of a metatarsal and opposed cuneiform and move the prepared end face of the metatarsal proximally against the prepared end face of the opposed cuneiform (e.g., during a compression step) without otherwise realigning the metatarsal.

The clinician can move the one or more metatarsals being realigned (e.g., second metatarsal 14 and/or third metatarsal 16) by hand and/or with the aid of one or more instruments. For example, the clinician can grasp the second and/or third metatarsal and advance the distal end of the metatarsal laterally to reduce the metatarsus adductus angle. The clinician may insert one or more pins into the metatarsal being moved (e.g., second and/or third metatarsal) to provide a joystick or structure that can be grasped to manipulate movement of the bones. Additionally or alternatively, the clinician may utilize a tenaculum or tong to grasp one or both of the second and third metatarsals to facilitate realignment.

In some examples, the clinician may use a bone positioning guide (also referred to as a bone positioning device) to help apply a force to a metatarsal (e.g., second metatarsal 14 and/or third metatarsal 16) to facilitate realignment. The bone positioning guide may include one end that engages with (e.g., contacts, with or without being provisionally fixated to) the metatarsal to which the force is being applied and another end that engages with (e.g., contacts, with or without being provisionally fixated to) a different bone.

One type of bone positioning guide that may be used to move a metatarsal in one or more planes, such as used to move second metatarsal 14 and third metatarsal 16, is a compressor instrument. For example, when an opening (e.g., wedge-shaped opening) is created at the second and third TMT joints during preparation of the bone ends, a compressor may be attached to the second and/or third metatarsal and another bone, such as the intermediate cuneiform and/or lateral cuneiform, respectively. The compressor may apply a distal-to-proximal force across the second and/or third TMT joints, causing the opening created across the joint to close. When the opening is wedge-shaped, causing the wedge-shaped opening to close can cause the distal end of second metatarsal 14 and/or third metatarsal 16 to pivot in the transverse plane. When used, the compressor may additionally or alternatively be used to compress the ends of the bone faces together, e.g., by compressing intermediate cuneiform 28 and second metatarsal 14 together and/or compressing lateral cuneiform 30 and third metatarsal 16 together, to facilitate subsequent fixation and fusion.

A variety of different compressor designs can be used to move one or more bones according to disclosure. In general, a compression instrument can provide compression functionality (e.g., moving bones towards each other) when actuated in one direction and distraction functionality (e.g., moving bones away from each other) when actuated in the opposite direction. For this reason, a compressor may also be referred to as a compressor-distractor. While compressor-distractor devices having a variety of configurations can be used to perform the techniques of the disclosure, in some examples, a compressor-distractor is configured relative to the anatomical profile of the foot to facilitate compression and/or distraction of one or more lesser metatarsals/TMT joints while positioning the compressor-distractor at a location that is unobtrusive to the incision site(s) where the clinician is working.

FIG. 13 is a perspective view of an example compressor-distractor 160 that can be used in systems and techniques. Compressor-distractor 160 is illustrated as having a first engagement arm 162 and a second engagement arm 164. Compressor-distractor 160 also includes an actuator 166 that is operably coupled to the first engagement arm 162 and the second engagement arm 164. Actuator 166 can be actuated to move the two engagement arms toward each other and away from each other to adjust a separation distance between the two arms. Further details on an example compressor-distractor that can be used according to the disclosure is described in U.S. Patent Publication No. 2023/0263536, filed on Feb. 24, 2023, and titled "DEVICES AND TECHNIQUES FOR TREATING LESSER METATARSALS OF THE FOOT," the entire contents of which are incorporated herein by reference.

With additional reference to FIG. 4, the example technique may involve provisionally fixating the moved position of the second metatarsal and the third metatarsal prior to permanent fixation (120). For example, after moving the second metatarsal and third metatarsal into a desired realigned position in one or more planes, such as the transverse plane (which may also involve moving the fourth metatarsal and fifth metatarsal), the clinician may optionally provisionally fixate the moved position. Provisional fixation can hold the moved position of one or more bones to facilitate subsequent surgical steps, such as application of one or more permanent fixation devices and/or the performance of additional surgical steps (e.g., first metatarsal realignment to correct a bunion deformity).

To provisionally fixate the moved position of the one or more bones, the clinician may insert one or more pins into and/or through a moved bone and into an adjacent bone. For example, the clinician may insert a pin through the second metatarsal and into an adjacent bone (e.g., a cuneiform) and/or insert a pin through the third metatarsal and into an adjacent bonc. The pin may be in the form of a rod and/or a wire (K-wire), and may or may not be configured to apply compression across a joint between the bones in which the pin is inserted, e.g., by having an enlarged region of the pin that presses against the outer surface of the bone through which the tip of the pin is inserted, thereby applying compression.

Independent of whether the clinician deploys a provisional fixation device, the clinician may apply one or more permanent fixation devices to facilitate fusion of the second and third TMT joints following reduction of the metatarsus adduction angle (step 120 in FIG. 4). The one or more fixation devices can extend across the second and/or third TMT joints to secure and hold opposed bone ends together for fusion (and/or other TMT joint in instances in which a different TMT joint is prepared for fusion). For example, the clinician may apply a first fixation device across the second TMT joint and apply a second fixation device across the third TMT joint.

Figure 14:
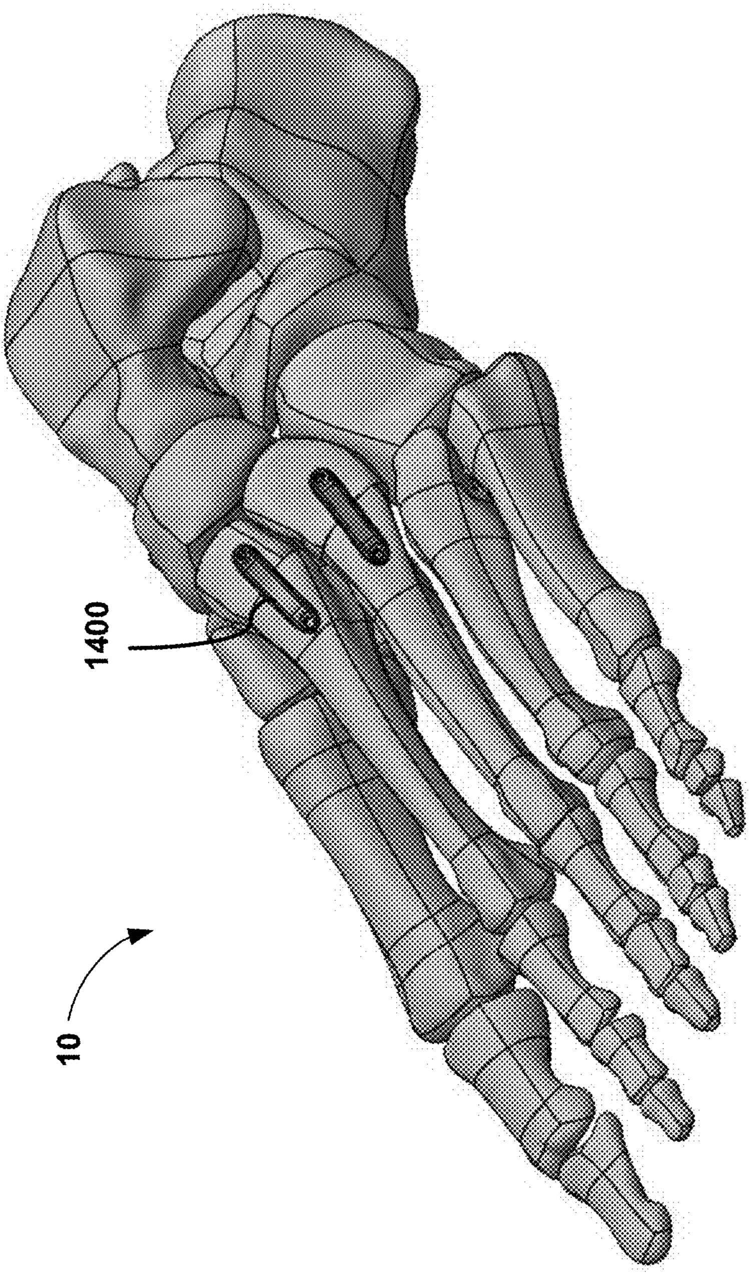

A bone fixation device may be any feature or combination of features that holds two bone portions in fixed relationship to each other to facilitate fusion of the bone portions during subsequent healing. Any one or more bone fixation devices that can be used include, but are not limited to, a bone screw (e.g., a compressing bone screw), a bone plate, a bone staple, an external fixator, an intramedullary implant, and/or combinations thereof. Depending on the type of bone fixation device selected, the bone fixation device may be attached to external surfaces of the bone portions being fixated or may be installed as an intramedullary device internal to the bone portions. FIG. 14 illustrates example bone fixation devices 1400 applied across the second and third TMT joints. Fixation devices 1400 may be in the form of a staple, such as that described in U.S. Patent Publication No. 2024/0081817, filed Sep. 14, 2023 and titled "BONE FIXATION TECHNIQUES AND IMPLANTS," the entire contents of which are incorporated herein by reference.

A metatarsus adduction deformity may present with a hallux valgus misalignment in some patients. Accordingly, a clinician performing a metatarsus adduction correction procedure may also perform a hallux valgus correction on the patient undergoing treatment. For example, the first metatarsal may be realigned prior to moving a lesser metatarsal (e.g., the second and third metatarsals), or may be realigned after moving the lesser metatarsal (e.g., the second and third metatarsals) but prior to permanently fixating the lesser TMT joint(s).

While the order of the surgical procedure may vary, in some applications, it is useful to reposition one or more lesser metatarsals (e.g., second and/or third metatarsals) prior to correcting the alignment of the first metatarsal. By initially repositioning the lesser metatarsal, such as the second and third metatarsals (and, in some examples, also correcting the position of the fourth and fifth metatarsals), the clinician may be able to better anatomically realign the first metatarsal relative to the aligned lesser metatarsals. Correction of the alignment of one or more of the lesser metatarsals may change the extent of misalignment of the first metatarsal, which can then be further corrected during a subsequent first metatarsal realignment step.

To correct the alignment of first metatarsal 12, the clinician may surgically access the first TMT joint. Once accessed the clinician may prepare an end of first metatarsal 12 and an opposed end of medial cuneiform 26. The clinician may prepare the ends of the bones with or without cutting, as discussed above with respect to preparation of the ends of second metatarsal 14 and third metatarsal 16 (e.g., using any preparation technique discussed herein). In instances in which the clinician prepares one or more bone ends using a cutting instrument, the clinician may or may not utilize a cut guide to guide controlled cutting of the bone ends and/or a bone preparation template to indicate where bone preparation should be performed.

Either before or after preparing one or both ends of first metatarsal 12 and medial cuneiform 26, the clinician may move first metatarsal 12 in at least one plane (e.g., the transverse plane, the frontal plane) to close an intermetatarsal angle between the first metatarsal and second metatarsal 14. In some examples, the clinician moves the first metatarsal in multiple planes, such as the transverse plane and/or frontal plane and/or sagittal plane. The clinician may or may not utilize a bone positioning guide to facilitate movement of the first metatarsal relative to the second metatarsal and/or medial cuneiform. With the first metatarsal moved to a desired position, the clinician can optionally provisionally fixate the moved position of the first metatarsal and then permanently fixate the moved position using one or more bone fixation devices, such as those described above. Additional details on example first metatarsal realignment instruments and techniques that can be used are described in U.S. Pat. No. 9,622,805, issued Apr. 18, 2017 and entitled "BONE POSITIONING AND PREPARING GUIDE SYSTEMS AND METHODS."

While the technique of FIG. 4 has generally been described with reference to preparation of second TMT joint 36 and third TMT joint 38 and movement of both second metatarsal 14 and third metatarsal 16 (optionally in combination with movement of fourth metatarsal 18 and fifth metatarsal 20), the techniques and/or devices may be performed on single TMT joints and/or different TMT joints without departing from the scope of the disclosure. For example, the technique of FIG. 4 may be performed on a single lesser TMT joint, such as only the second TMT joint 36, only the third TMT joint 38, only the fourth TMT joint 40, or only the fifth TMT joint 42, in each case optionally in combination with preparation of the first TMT joint 34 and realignment of the first metatarsal. Other combinations of joint preparation are also possible.

Further, while example techniques are described herein generally in connection with realigning one or more bone in, for example, a lateral direction in a transverse plane, in some applications, the clinician may reposition perform a procedure according to the disclosure without realigning in such plane(s). For example, in the case of an arthritic joint, the clinician may prepare the end faces of the metatarsal and opposed cuneiform for fusion, e.g., by making parallel cuts across the faces of the ends of the bones. The clinician can then compress the prepared end faces of the bones together and apply fixation to promote fusion across the joint without otherwise repositioning one bone relative to another bone.

In some applications where the clinician prepares only a single lesser TMT joint for fusion (again, optionally as part of a procedure that also prepares the first TMT joint), the clinician may move the lesser metatarsal associated with that TMT joint in one or more planes, e.g., using devices and/or techniques discussed herein. Repositioning of the metatarsal associated with the lesser TMT joint being prepared may or may not also move one or more adjacent metatarsals to the lesser metatarsal being moved through ligamentous tissue. For example, if the clinician prepares second TMT joint 36 and moves second metatarsal 14, the repositioning of the second metatarsal may or may not cause realignment of third metatarsal 16, fourth metatarsal 18, and/or fifth metatarsal 20.

As discussed above, a bone realignment technique according to the disclosure may involve cutting an end of a cuneiform and/or an end of an opposed metatarsal. In such applications, the clinician may perform the cuts freehand or with the aid of one or more cut guides (also referred to herein interchangeably as a cutting guide). The use of a cut guide may facilitate more accurate and repeatable cuts patient-to-patient, promoting more consistent clinical outcomes across a range of patients an anatomical deformities. When a cut guide is used, the cut guide may generally define at least one guide surface positionable over a side of the bone to be cut, such as a dorsal side. The clinician can place a cutting instrument adjacent to, and optionally in contact with, the guide surface and translate the cutting instrument relative to the guide surface to perform a cut in a plane parallel to the guide surface. For example, the clinician may place the cutting instrument in contact with the guide surface and then translate the cutting instrument relative to the guide surface, e.g., plantarly into a bone and/or in a medial or lateral direction. The guide surface may bound movement of the cutting instrument to a desired direction of cutting.

In accordance with some examples of the present disclosure, bone cutting guides and associated techniques are provided that facilitate a less invasive method for treating lesser metatarsals of a foot. The technique can involve making a comparatively small incision through the skin of a patient and positioning a portion of a bone cutting guide through the incision. The bone cutting guide can include a body extending lengthwise from a medial side to a lateral side, with defined medial and lateral side skin cutout features. The technique can allow for the retraction of skin along the incision to expose the bones, guiding a cutting instrument along the guide surfaces to cut the bones with precision.

In some examples, a bone cutting guide for a less invasive procedure incudes a body extending lengthwise from a medial sidewall to a lateral sidewall, with the body defining a cuneiform-side guide surface and a metatarsal-side guide surface. The inclusion of a cutout feature in at least one of the medial sidewall and the lateral sidewall can enable the positioning of the skin along the incision relative to the surfaces of the guide to selectively control the location of the opening provided by the incision relative to the underlying TMT joints.

In use, the clinician can use the bone preparation guide to retract the skin along the incision to expose at least a portion of a first bone under the medial or lateral portion of the bone cutting guide, and then guide a cutting instrument along a first side guide surface of the bone cutting guide to cut the first bone. The clinician can then reposition the skin along the incision to expose at least a portion of a second bone under the opposite portion of the bone cutting guide, and guide the cutting instrument along a second side guide surface to prepare the second bone.

In some configurations, the bone cutting guide includes a seeker element extending between a bone contacting surface of the metatarsal-side guide surface and a bone contacting surface of the cuneiform-side guide surface. The seeker element can provide a stable anchoring mechanism within the anatomical landmarks of the foot, minimizing the risk of the guide shifting or moving during the surgical procedure and/or orienting the guide surfaces of the bone cutting guide relative to the target anatomy to be cut. For example, the seeker element can help facilitate the identification and engagement of specific joints, such as the second and third tarsometatarsal joints.

In some examples, the bone cutting guide includes a plurality of pin holes. The guide can be temporarily fixed on or near one or both of at least one cuneiform and at least one metatarsal by inserting one or more pins through the pin holes. This temporary fixation can help ensure that the bone cutting guide remains securely in place during the surgical procedure, reducing the risk of movement or displacement that could lead to inaccurate cuts. One or more pins inserted through the pin holes can also help to hold the skin offset/retracted from the bone cutting guide during the surgical procedure.

FIG. 8 is a top view of foot 10 showing the example cut guide 150 introduced with respect to FIG. 5 above. With further reference to FIG. 5, cut guide 150 includes at least one guide surface 152 positionable over a dorsal side of a bone to be cut. For example, cut guide 150 can includes a metatarsal-side guide surface 152 positionable over a dorsal side of second metatarsal 14 and third metatarsal 16. The metatarsal-side guide surface 152 can extend straight (e.g., parallel) or an angle in a dorsal to plantar direction (in other words, in the sagittal plane) and can guide the cutting tool in a direction defined by the guide surface. In use, the clinician can place a cutting tool in abutting relationship with metatarsal-side guide surface and advance the cutting tool relative to the guide surface to remove an end of the metatarsal being cut (e.g., second metatarsal 14 and/or third metatarsal 16).

In some examples, cut guide 150 defines a single guide surface. In other examples, cut guide 150 may include multiple guide surfaces, for example spaced apart from each other to define a cutting slot between the guide surfaces. In the illustrated example, cut guide 150 is shown having first metatarsal-side guide surface and a second metatarsal-side guide surface parallel to the first guide surface to define a cutting slot between the two guide surfaces. A clinician can insert a cutting tool, such as a saw blade, in the cutting slot to guide removal of a portion of the end of second metatarsal 14 and a portion of the end of third metatarsal 16.

Cut guide 150 is also illustrated as having a guide surface 154 positionable over a dorsal side of intermediate cuneiform 28 and lateral cuneiform 30. The cuneiform-side guide surface 154 can extend straight (e.g., parallel) or an angle in a dorsal to plantar direction (in the sagittal plane) and can guide the cutting tool in a plane parallel to the guide surface. In use, the clinician can place a cutting tool in abutting relationship with guide surface 154 and advance the cutting tool relative to the guide surface to remove an end of an opposed cuneiform/cuboid bone, such as intermediate cuneiform 28 and lateral cuneiform 30.

As with the metatarsal-side guide surface 152, the cuneiform-side guide surface 154 may define a single guide surface or may include multiple guide surfaces, for example spaced apart from each other to define a cutting slot between the guide surfaces. In the illustrated example, cut guide 150 is shown having first cuneiform-side guide surface and a second cuneiform-side guide surface parallel to the first guide surface to define a cutting slot between the two guide surfaces. A clinician can insert a cutting tool, such as a saw blade, in the cutting slot to guide removal of a portion of the end of intermediate cuneiform 28 and lateral cuneiform 30.

In some examples, each guide surface (e.g., 152, 154) of bone cutting guide 1500 is configured as a continuous guide surface extending across multiple metatarsals (e.g., second metatarsal 14 and third metatarsal 16) and/or multiple cuneiforms (e.g., intermediate cuneiform 28 and later cuneiform 30). In other configurations, one or more of the guide surfaces are configured as a discontinuous guide surface, or two guide surfaces, separately positionable over each of the metatarsals and/or cuneiforms. When so configured, cut guide 150 may have a guide surface region positionable over each of two lesser metatarsals (e.g. second metatarsal 14 and third metatarsal 16) and/or positionable over each of two lesser cuneiforms (e.g., intermediate cuneiform 28 and lateral cuneiform 30) but a discontinuity, break, and/or stop between the guide surface regions that prevents a continuous cut from being made that transects both metatarsals and/or cuneiforms.

Figure 10B:
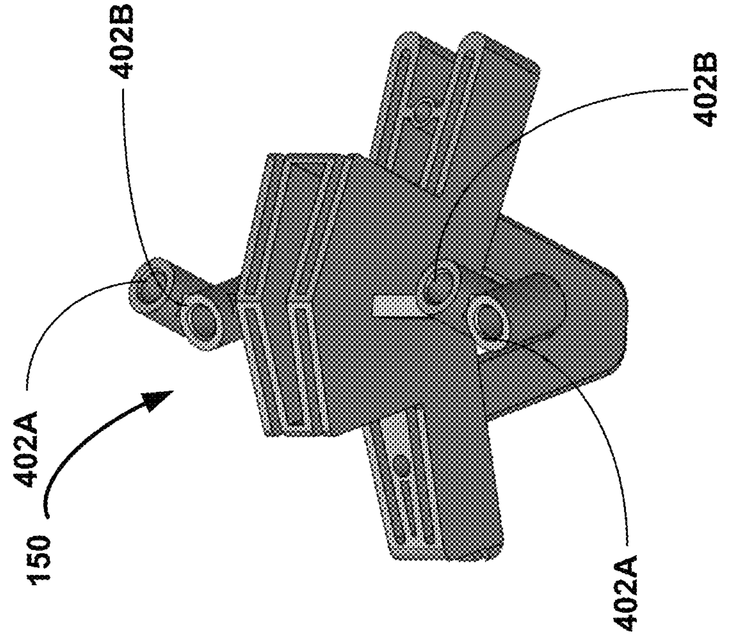
FIGS. 10A-10K illustrate example configurations of bone cutting guides including skin cut out and pin hole features.
Figure 10A:
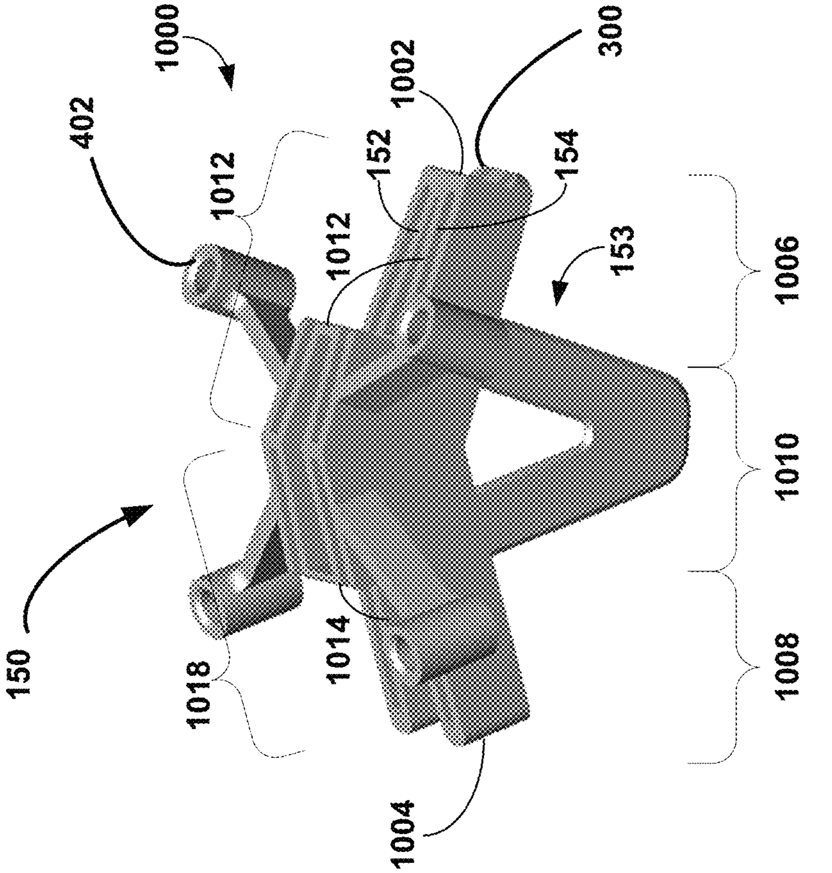
Figure 10C:
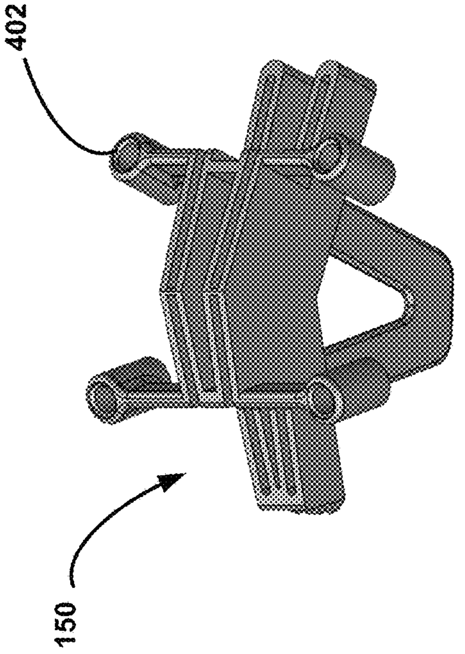
Figure 10E:
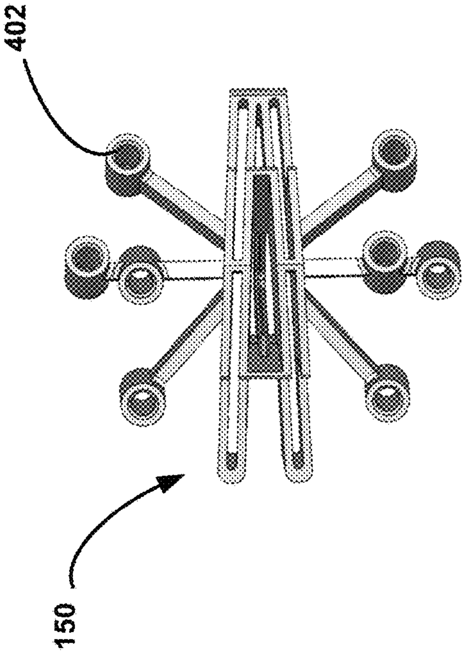
Figure 10D:
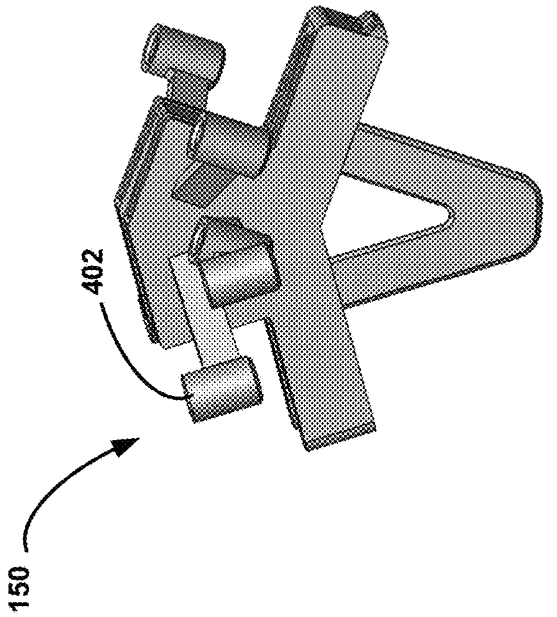
Figure 10G:
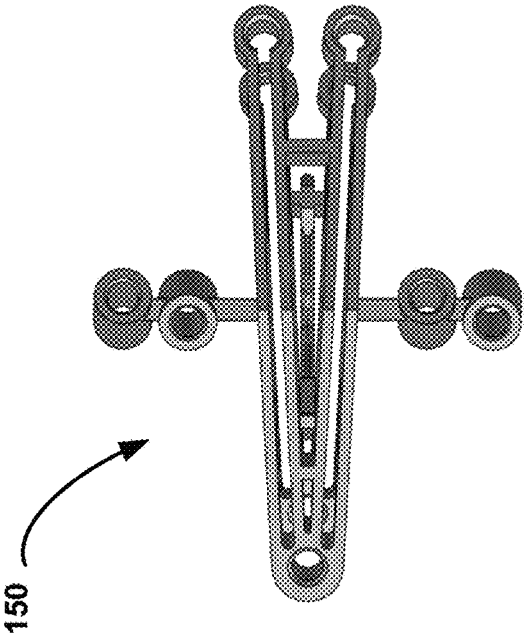
Figure 10F:
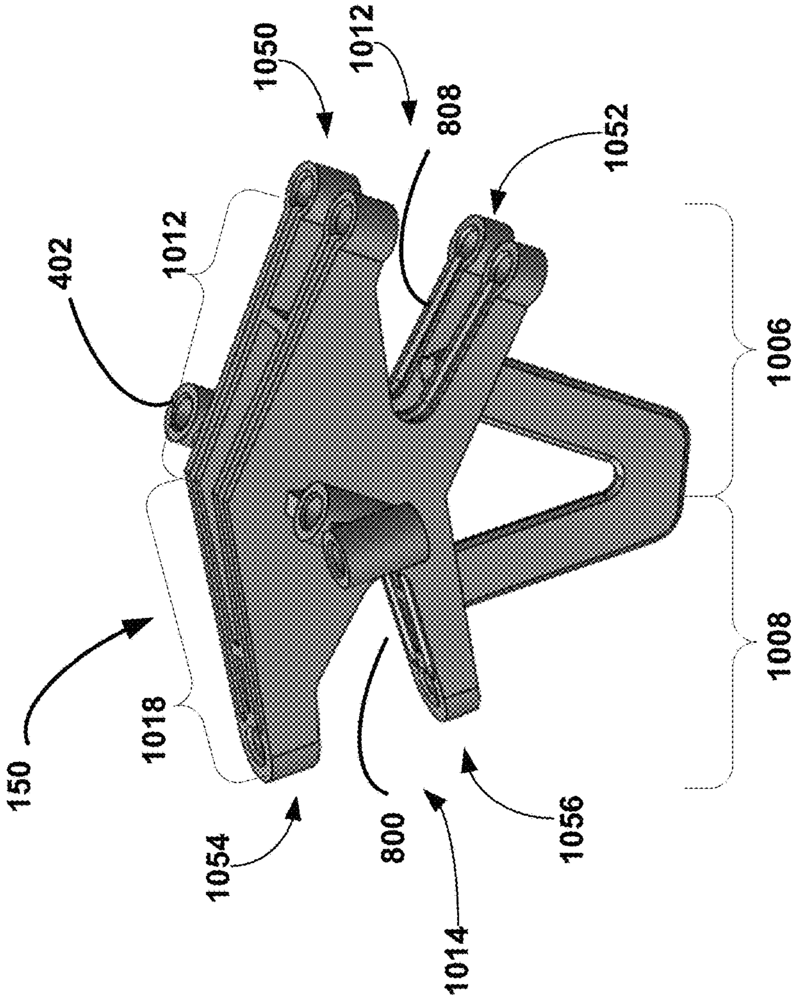
Figure 10I:
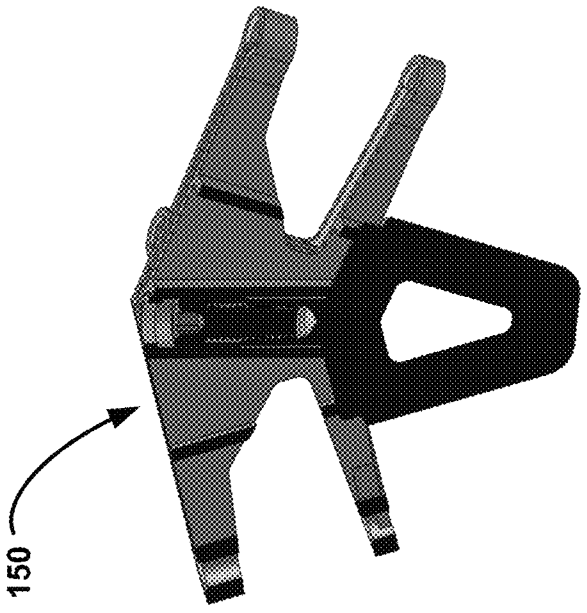
Figure 10H:
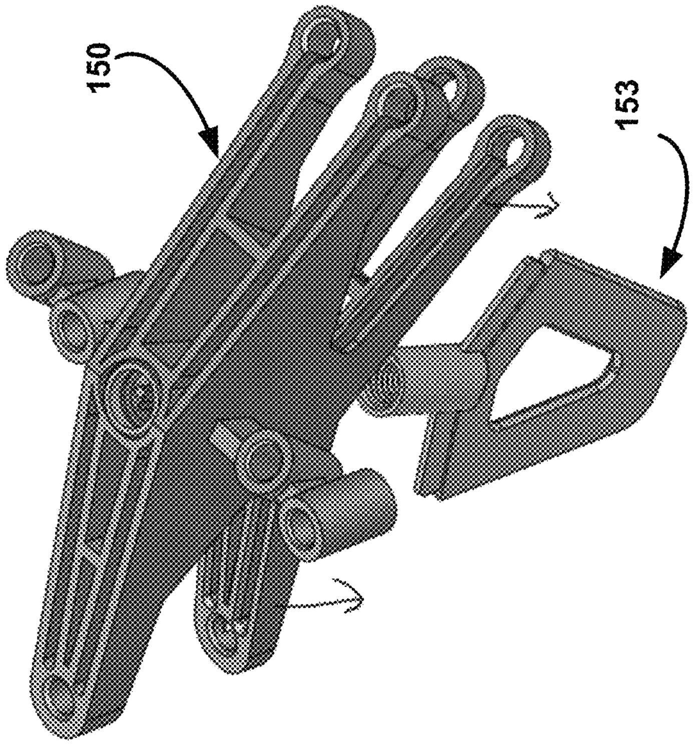

Referring now to FIGS. 10A-10K, exemplary cut guides 150 are illustrated in accordance with some aspects of the disclosure. Shown at FIGS. 10A-10G are one piece cut guides 150 that include various configurations of pin holes while FIG. 10H illustrates an exemplary two piece cut guide 150 (comprising removable guide elements 150A and projection feature 150B) and FIG. 10I illustrates a three piece cut guide 150 (comprising removable guide elements 153A and 153B and a projection feature 155 that may be inserted into the joint space).

With reference to the example configuration of FIGS. 10A and 10B, bone cutting guide 150 is illustrated as having a body 1000 that extends lengthwise from a medial side 1002 to a lateral side 1004. The example bone cutting guide includes a medial portion 1006, a lateral portion 1008, and an intermediate portion 1010. Medial portion 1006 can be positioned through incision 151 and under the skin of the patient and selectively exposed by repositioning the skin relative to cut guide 150 during a surgical procedure. Lateral portion 1008 can also be positioned through incision 151 and under the skin of the patient and selectively exposed by repositioning the skin relative to cut guide 150 during a surgical procedure. Intermediate portion 1010 can be configured to extend outwardly through incision 151 during a surgical procedure, e.g., with a top surface of intermediate portion 1010 above the skin and the skin retracted medially and/or laterally relative to intermediate portion 1010 during the procedure.

In the illustrated example, body 1000 defines a medial side skin cutout feature 1012, which is shown as being defined between medial portion 1006 and intermediate portion 1010. Body 1000 is also illustrated as defining a lateral side skin cutout feature 1014, which is shown as being defined between lateral portion 1008 of the bone cutting guide and intermediate portion 1010. Each feature described as a skin cutout feature may be region of bone cutting guide 150 against which skin can be retracted and retained, e.g., to expose the portion of the bone cutting guide on an opposite side of the body from the side defining the skin cutout feature providing retraction. In some examples, each skin cutout feature may have a depth from a side edge (e.g., medial-most side edge, lateral-most side edge) of body 1000 to an offset wall surface bounding a maximum depth of the feature of at least 0.5 mm, such as at least 1 mm, at least 2 mm, or at least 3 mm.

In use, a clinician can make incision 150 through a skin of a patient and insert at least a portion of bone cutting guide 150 through the incision and under the skin of the patient. For example, the clinician can insert at least a portion of medial portion 1006 under a portion of the skin covering second metatarsal 14 and/or intermediate cuneiform 28. The clinician can additionally or alternatively insert at least a portion of lateral portion 1008 under a portion of the skin covering third metatarsal 16 and/or lateral cuneiform 30.

The clinician can apply a force to the skin along the incision line (e.g., via a retractor) before and/or after inserting bone cutting guide 150 under the skin to retracting the skin along the incision. The clinician can retract the skin medially to expose some or all of the second TMT joint (e.g., the end of one or both of second metatarsal 14 and/or intermediate cuneiform 28) through the incision and the portion of the cut guide overlying the underlying bones. This can cause the skin on the lateral side of bone cutting guide 150 to cover the lateral portion 1008 of the bone cutting guide and third TMT joint, with the skin on the lateral side being retracted by and retained in the lateral side skin cutout feature 1014. After retraction, the clinician can guide a cutting instrument along a medial side guide surface 1016 of bone cutting guide 150, which can be a metatarsal-side guide surface and/or cuneiform-side guide surface extending on the medial side of the guide (e.g., extending on the medial half of the guide along medial portion 1006 and/or intermediate portion 1010 over second metatarsal 14 and/or intermediate cuneiform 30).

After preparing the second TMT joint, the clinician can apply a force to the skin along the incision line (e.g., via a retractor) to reposition the skin along the incision. The clinician can retract the skin laterally to expose some or all of the third TMT joint (e.g., the end of one or both of third metatarsal 16 and/or lateral cuneiform 30) through the incision and the portion of the cut guide overlying the underlying bones. This can cause the skin on the medial side of bone cutting guide 150 to cover the medial portion 1006 of the bone cutting guide and second TMT joint, with the skin on the medial side being retracted by and retained in the medial side skin cutout feature 1012. After retraction, the clinician can guide a cutting instrument along a lateral side guide surface 1018 of bone cutting guide 150, which can be a metatarsal-side guide surface and/or cuneiform-side guide surface extending on the lateral side of the guide (e.g., extending on the lateral half of the guide along lateral portion 1008 and/or intermediate portion 1010 over third metatarsal 16 and/or lateral cuneiform 30). While the foregoing example has described a technique in which the second TMT joint is exposed and prepared before the third TMT joint is exposed and prepared, the order of operation may be reversed and/or a different order of operation may be utilized without departing from the scope of the disclosure.

Figure 15B:
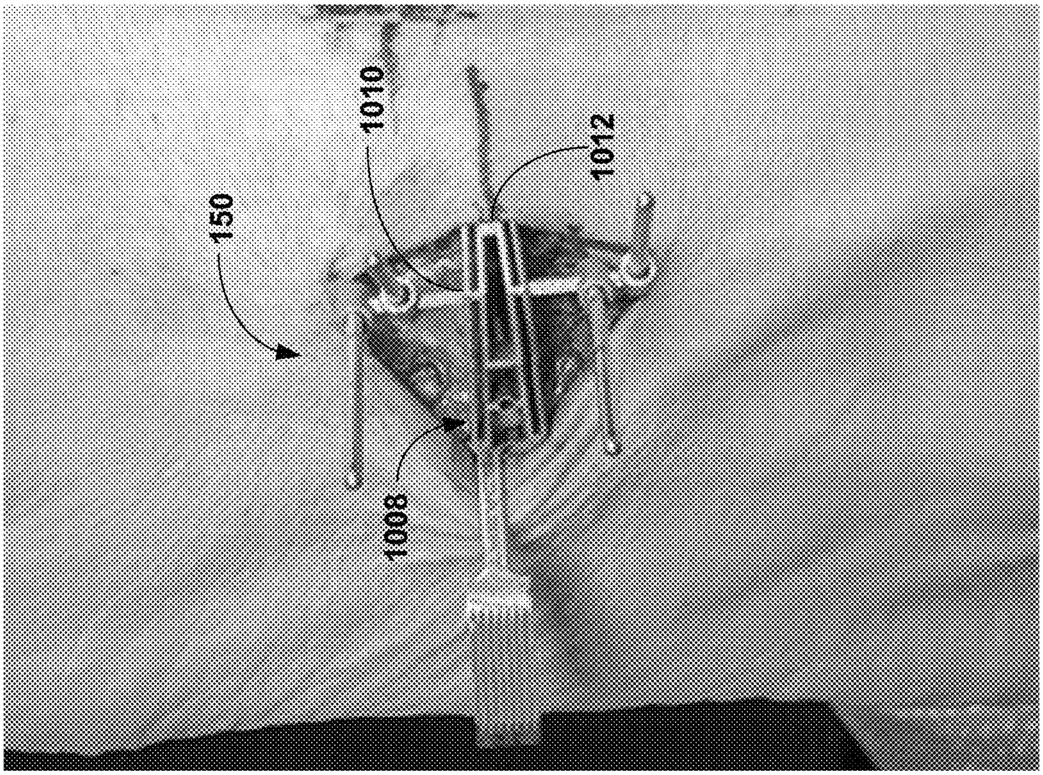
FIG. 15B is an illustration of the example cut guide of FIG. 15A showing the skin retracted in one direction to expose one portion of the cut guide through the incision while the second portion of the cut guide is positioned under the skin.
Figure 15A:
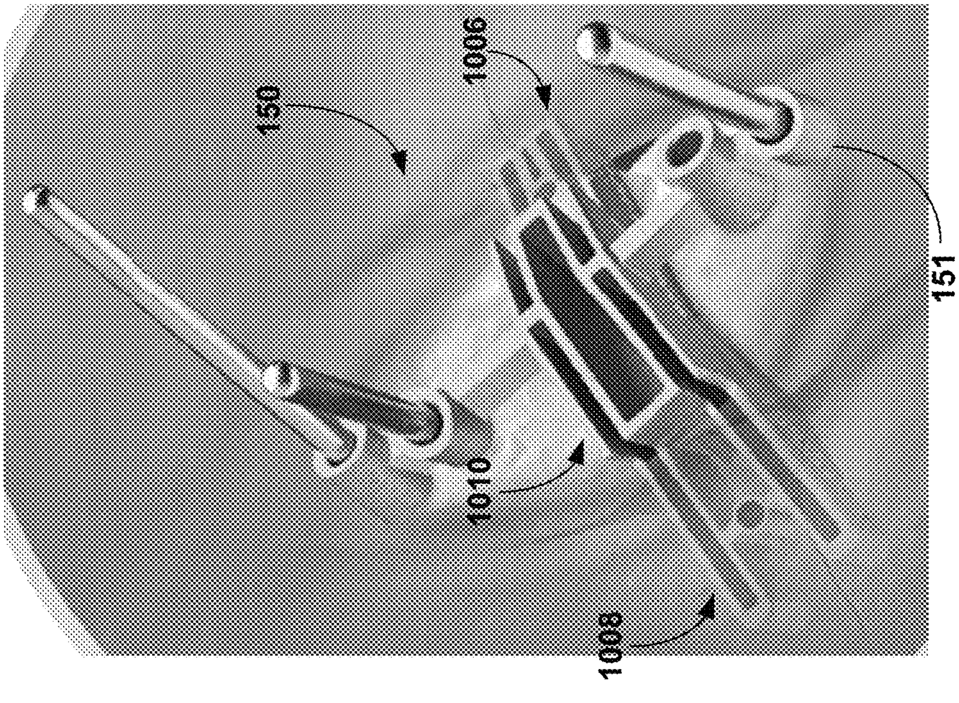
FIG. 15A is an illustration of an example configuration of a cut guide having a medial portion and a lateral portion each positioned under the skin on opposing sides of an incision with an intermediate portion having a top surface positioned above the skin aligned with the incision line.

FIG. 15A is an illustration of an example configuration of a cut guide 150 having a medial portion 1006 and a lateral portion 1008 each positioned under the skin on opposing sides of an incision 151 with an intermediate portion 1010 having a top surface positioned above the skin aligned with the incision line. FIG. 15B is an illustration of cut guide 150 of FIG. 15A showing the skin retracted one direction (which, in the illustrated configuration, is laterally) to expose the lateral portion 1008 of the cut guide through the incision 151. The skin on the medial side of the cut guide is retained at medial side skin cutout feature 1012 to hold the skin offset from the guide surfaces exposed on lateral portion 1008. A clinician can prepare the ends of the bones forming the third TMT joint when so positioned. FIG. 15A shows a supplemental retraction device on the lateral side of cut guide 150 to help hold the skin offset laterally from the guide surfaces of the cut guide.

Before or after preparing the ends of the bones forming the third TMT joint, the clinician can position the skin retracted medially to expose the medial portion 1006 of the cut guide through the incision 151. The skin on the lateral side of the cut guide can then be retained at lateral side skin cutout feature 1014 to hold the skin offset from the guide surfaces exposed on medial portion 1006. A supplemental retraction device can be positioned on the medial side of cut guide 150 to help hold the skin offset medially from the guide surfaces of the cut guide. A clinician can proceed to prepare the ends of the bones forming the second TMT joint when so positioned.

In some embodiments, cut guide 150 can include a tissue retraction cavity 300 on medial side of the cut guide, on lateral side of the cut guide, and/or on both sides of the cut guide. The tissue retraction cavity can define an offset region of medial sidewall 1002 and/or lateral sidewall 1004 against which the skin along incision 151 can be retracted.

In the illustrated arrangement of FIG. 10A, cut guide 150 includes at least two parallel fixation holes 402 extending outwardly via arms from the body defining the at least one guide surface of the cut guide. Additionally, in some embodiments, fixation holes 402 extend at a skewed angle relative to the parallel fixation holes and assist with temporarily fixing the bone cutting guide 150 and/or skin to one or more bones of the foot 10. The fixation holes 402 define the skewed angle may receive a fixation pin that, in use, extends in a dorsal-lateral direction (or a dorsal-medial direction) away from the bone portion being prepared.

FIG. 10B illustrates an example configuration of fixation holes 402 in which the fixation holes are positioned on intermediate portion 1010 of bone cutting guide 150. For example, the bone cutting guide may include a first pair of fixation holes 402A on each side of intermediate portion 1010 that are angled medially and a second pair of fixation holes 402B on each side of intermediate portion 1010 that are angled laterally. A clinician can use the different pairs of fixation holes to pin the guide to the underlying bones depending on whether the clinician is preparing the second TMT joint or third TMT joint during the procedure.

Figure 9B:
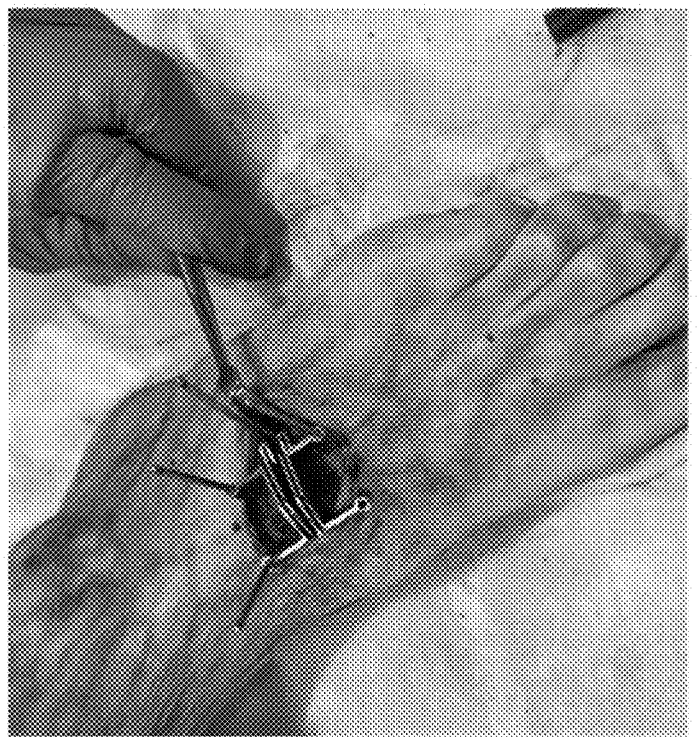
FIGS. 9A and 9B illustrate example skin cut outs of a bone cutting guide being used to reposition the tissue of the incision and expose different bone sections.
Figure 9A:
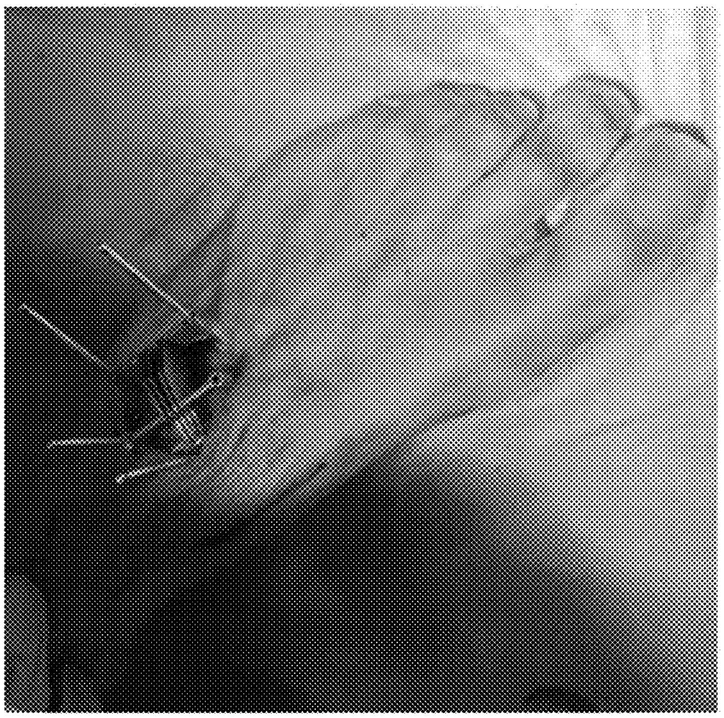

According to some aspects, skin cutout portions 800 and 808 may be included in some guides to facilitate skin at the incision to be repositioned as shown in FIGS. 9A and 9B. The shape of the skin cutout portions may vary, as shown in the different exemplary embodiments in FIGS. 10A-10K. In FIG. 10K, for example, skin cutout portion 808 includes a top portion 801 that is designed to stick out of the incision and a bottom portion 802 that is designed to be inserted into the incision. In some embodiments the size of the bottom portion may be 30-60% of the overall height of the cut channel depending on the overall height of the cut channel. In some embodiments, for example, bottom portion of a short guide may be within a range from 4 mm to 7 mm, such as from about 5.5 mm to 6.5 mm, or equal to or about 5.8 mm and the top portion may be within a range from 3 mm to 5 mm, such as equal to or about 4.2 mm. In a tall guide the bottom portion of a short guide may be within a range from 4 mm to 7 mm, such as from about 5.5 mm to 6.5 mm, or equal to or about 5.8 mm and the top portion may be within a range from 8 mm to 11 mm, such as from 8.5 mm to 10 mm, or equal to or about 9.2 mm.

With further reference to FIGS. 10A and 10B, bone cutting guide is illustrated as being configured with medial portion 1006 in the form of a medial side shelf positionable under the skin of the patient and lateral portion 1008 in the form of a lateral side shelf positionable under the skin of the patient. In this configuration, intermediate portion 1010 is positionable projecting outwardly through the incision between the medial side shelf and the lateral side shelf.

In some configurations, the medial and/or lateral portions of bone cutting guide 150 may include separate portions positionable over and under the skin of the patient. For example, FIGS. 10F and 10G are side and top views, respectively, of another example configuration of bone cutting guide 150 where like features refer to like elements discussed above. In the illustrated example of FIGS. 10F and 10G, the medial portion 1006 of the bone cutting guide includes an upper guide surface 1050 and a lower guide surface 1052. Medial side skin cutout feature 1012 is defined between the upper guide surface 1050 and the lower guide surface 1052. In this example, the lateral portion 1008 of the bone cutting guide also includes an upper guide surface 1054 and a lower guide surface 1056. In this example, lateral side skin cutout feature 1014 is defined between the upper guide surface 1054 and the lower guide surface 1056.

In use, the clinician can retract the skin medially along incision 151 to expose some or all of the second TMT joint (e.g., the end of one or both of second metatarsal 14 and/or intermediate cuneiform 28) through the incision and the portion of the cut guide overlying the underlying bones. This can cause the skin on the lateral side of bone cutting guide 150 to cover the lateral portion 1008 of the bone cutting guide and third TMT joint, with the skin on the lateral side being retracted by and retained in the lateral side skin cutout feature 1014. With the skin on the lateral side retained in lateral side skin cutout feature 1014, the skin can be retained between upper guide surface 1054 and lower guide surface 1056, with the lower guide surface under the skin and the upper guide surface over the skin. The upper guide surface 1050 and lower guide surface 1052 of medial portion 1006 can each define guide surfaces that are co-planar with each other, e.g., such that a cutting instrument guided by the bone cutting guide is guided by a surface of upper guide surface 1050 and a corresponding and aligned surface of lower guide surface 1052.

The clinician can also retract the skin laterally along incision 151 to expose some or all of the third TMT joint (e.g., the end of one or both of third metatarsal 16 and/or lateral cuneiform 30) through the incision and the portion of the cut guide overlying the underlying bones. This can cause the skin on the medial side of bone cutting guide 150 to cover the medial portion 1006 of the bone cutting guide and second TMT joint, with the skin on the medial side being retracted by and retained in the medial side skin cutout feature 1012. With the skin on the medial side retained in medial side skin cutout feature 1012, the skin can be retained between upper guide surface 1050 and lower guide surface 1052, with the lower guide surface under the skin and the upper guide surface over the skin. The upper guide surface 1054 and lower guide surface 1056 of lateral portion 1008 can each define guide surfaces that are co-planar with each other, e.g., such that a cutting instrument guided by the bone cutting guide is guided by a surface of upper guide surface 1054 and a corresponding and aligned surface of lower guide surface 1056.

Bone cutting guide 150 according to the disclosure can have a variety of additional or different features or configurations. As one example, bone cutting guide 150 may include a seeker 153 insertable into a TMT joint (e.g., second TMT joint, third TMT joint, and/or some or all of both the second TMT joint and third TMT joint). This can help orient bone cutting guide 150 relative to the underlying anatomy. Seeker 153 can be integrally attached to body 1000 and extend therefrom, e.g., to define a unitary or monolithic structure. Alternatively, seeker 153 can be detachably attached to body 1000. This can allow the seeker to optionally be inserted separately from body 1000 of bone cutting guide 150 and/or allow the body to be selected from a system of different available bodies and attached to seeker 150. FIGS. 10H and 10I illustrate an example configuration of bone cutting guide 150 have a body 1000 that is detachably connectable to seeker 153.

Figure 10J:
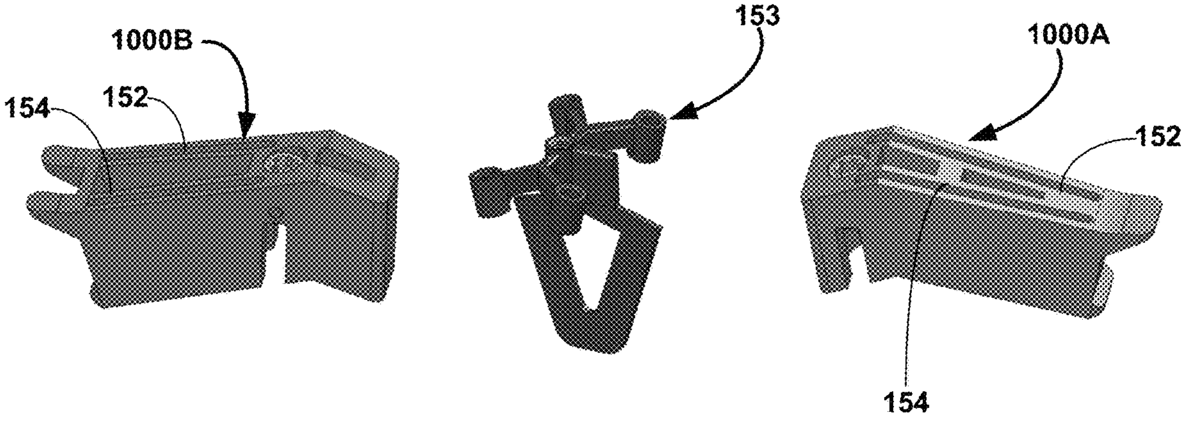
Figure 10K:
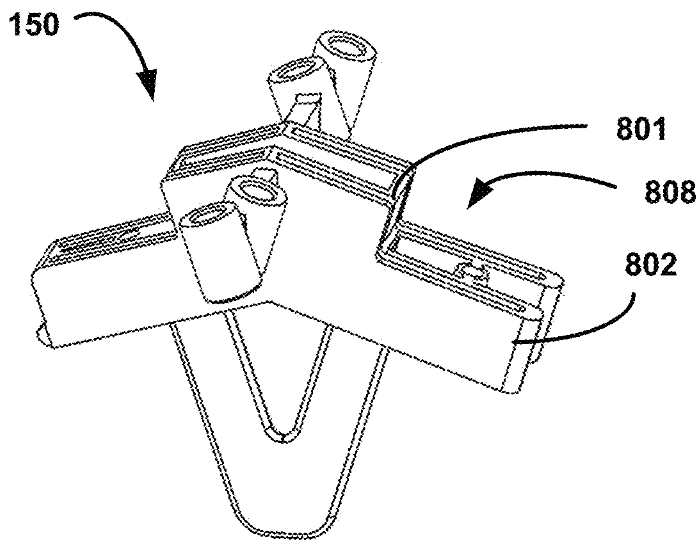

FIG. 10J illustrates a configuration of bone cutting guide 150 in which the bone cutting guide includes a medial body 1000A, a lateral body 1000B, and a seeker 153. Medial body 1000A defines a medial portion of a cuneiform-side guide surface 154, a medial portion of a metatarsal-side guide surface 152, and a medial side skin cutout feature 1012. Lateral body 1000B defines a lateral portion of a cuneiform-side guide surface 154, a lateral portion of a metatarsal-side guide surface 152, and a lateral side skin cutout feature 1014. The medial body 1000A and the lateral body 1000B can be independently attachable to the seeker. During a procedure, a clinician can attach either medial body 1000A or lateral body 1000B to seeker and use the attached body to prepare either second TMT joint or third TMT joint. After preparing that joint, the clinician can detach the body and attach the other body (e.g., while the seeker remains inserted into the joint space). The clinician can then use the other attached body to prepare the other of the second TMT joint or third TMT joint.

While the foregoing description of cut guide 150 and associated feature(s) has generally focused on a configuration for positioning over the second tarsometatarsal joint and the third tarsometatarsal joint, the cut guide can be configured to cut any tarsometatarsal joint or combination of joints. For example, cut guide 150 and associated locating feature(s) (when used) can be configured for positioning one or more guide surfaces over one or more bone ends defining the third tarsometatarsal joint and fourth tarsometatarsal joint, or the fourth tarsometatarsal joint and fifth tarsometatarsal joint, instead of the second and third tarsometatarsal joints. Accordingly, discussion of instruments and techniques for preparing an end of second metatarsal 14 and/or and end of intermediate cuneiform 28 (and/or an end of third metatarsal 16 and/or an end of lateral cuneiform 30) should be understood to apply equally to other lesser tarsometatarsal joint spaces and/or other bone ends.

Reference to a metatarsal-side and cuneiform-side for any device herein (e.g., bone positioner, cut guide) is intended to describe relative positions and orientations of features where the device crosses a TMT joint with a metatarsal on one side and a cuneiform on another side. Where the device is deployed across two different bones, such as the fourth metatarsal and the cuboid bone or yet other two bones or bone portions (e.g., two bone portions separated by a joint), the terminology can be changed based on that anatomy.

Embodiments of any instrument described herein (e.g., cutting guide, bone preparation template, bone positioning device) may include or be fabricated from any suitable materials (e.g., metal, plastic). In certain embodiments, an instrument is fabricated at least partially from a radiolucent material such that it is relatively penetrable by X-rays and other forms of radiation, such as thermoplastics and carbon-fiber materials. Such materials are useful for not obstructing visualization of bones using an imaging device when the instrument is positioned on bones.

Various examples have been described. These and other examples are within the scope of the following claims.

The invention claimed is:

1. A less invasive technique for treating lesser metatarsals of a foot, the technique comprising:

making an incision through a skin of a patient;

positioning at least a portion of a bone cutting guide comprising a body extending lengthwise from a medial side to a lateral side through the incision;

retracting the skin along the incision to expose at least a portion of the bone cutting guide positioned over a first joint;

guiding a cutting instrument along a first guide surface of the bone cutting guide to prepare the first joint;

repositioning the skin along the incision to expose at least a portion of the bone cutting guide positioned over a second joint, thereby covering the portion of the first joint with the skin; and guiding a cutting instrument along a second guide surface of the bone cutting guide to prepare the second joint.

2. The technique of claim 1, wherein the positioning of the skin along the incision is done using at least one of a skin feature on the medial side of the body of the bone cutting guide and a second skin feature on the lateral side of the body of the bone cutting guide.

3. A minimally invasive technique for treating lesser metatarsals of a foot, the technique comprising:

making an incision through a skin of a patient;

positioning a portion of a bone cutting guide comprising a body extending lengthwise from a medial side to a lateral side through the incision, wherein the bone cutting guide comprises a medial side skin cutout feature and a lateral side skin cutout feature;

retracting the skin along the incision to expose at least a portion of a first bone under (a) a medial portion of the bone cutting guide with the skin positioned in the lateral side skin cutout feature or (b) a lateral portion of the bone cutting guide with the skin positioned in the medial side skin cutout feature;

guiding a cutting instrument along a first side guide surface of the bone cutting guide to cut the first bone;

repositioning the skin along the incision to expose at least a portion of a second bone under an other of (a) the medial portion of the bone cutting guide with the skin positioned in the lateral side skin cutout feature or (b) the lateral portion of the bone cutting guide with the skin positioned in the medial side skin cutout feature; and guiding the cutting instrument along a second side guide surface of the bone cutting guide to cut the second bone.

4. The minimally invasive technique of claim 3, wherein positioning the portion of the bone cutting guide through the incision comprises positioning the medial side of the bone cutting guide under the skin, positioning the lateral side of the bone cutting guide under the skin, and positioning an intermediate portion of the bone cutting guide extending outwardly through the incision.

5. The minimally invasive technique of claim 4, wherein the medial side skin cutout feature is defined between the medial portion of the bone cutting guide and the intermediate portion of the bone cutting guide, and the lateral side skin cutout feature is defined between the lateral portion of the bone cutting guide and the intermediate portion of the bone cutting guide.

6. The minimally invasive technique of claim 3, wherein:

the medial portion of the bone cutting guide comprises an upper guide surface and a lower guide surface, with the medial side skin cutout feature defined between the upper guide surface and the lower guide surface; and the lateral portion of the bone cutting guide comprises an upper guide surface and a lower guide surface, with the lateral side skin cutout feature defined between the upper guide surface and the lower guide surface.

7. The minimally invasive technique of claim 3, wherein the bone cutting guide comprises a medial side shelf positionable under the skin, a lateral side shelf positionable under the skin, and an intermediate portion positionable projecting outwardly through the incision between the medial side shelf and the lateral side shelf.

8. The minimally invasive technique of claim 3, wherein positioning the portion of the bone cutting guide through the incision comprises positioning a seeker of the bone cutting guide through the incision into a portion of both a second tarsometatarsal joint and a third tarsometatarsal joint.

9. The minimally invasive technique of claim 3, wherein making the incision comprises making the incision shorter than a length necessary to simultaneously expose both the first bone and the second bone.

10. The minimally invasive technique of claim 3, wherein making the incision comprises making the incision less than or equal to 5.0 mm.

11. The minimally invasive technique of claim 3, wherein:

the first bone is a second metatarsal or a third metatarsal; and the second bone is an other of the second metatarsal or the third metatarsal.

12. The minimally invasive technique of claim 11, wherein:

retracting the skin along the incision to expose at least a portion of the first bone further comprises exposing at least a portion of a cuneiform separated from the first bone by a tarsometatarsal joint;

the first side guide surface is a first metatarsal side guide surface, and further comprising guiding the cutting instrument along a first cuneiform side guide surface of the bone cutting guide to cut the cuneiform separated from the first bone by the tarsometatarsal joint;

repositioning the skin along the incision to expose at least a portion of a second bone further comprises exposing at least a portion of a cuneiform separated from the second bone by a tarsometatarsal joint; and the second side guide surface is a second metatarsal side guide surface, and further comprising guiding the cutting instrument along a second cuneiform side guide surface of the bone cutting guide to cut the cuneiform separated from the second bone by the tarsometatarsal joint.

13. The minimally invasive technique of claim 3, wherein retracting the skin along the incision to expose at least the portion of the first bone and guiding the cutting instrument along the first side guide surface of the bone cutting guide to cut the first bone comprises retracting the skin along the incision to expose at least the portion of the first bone and guiding the cutting instrument along the first side guide surface of the bone cutting guide to cut the first bone while the second bone remains at least partially covered with the skin.

14. The minimally invasive technique of claim 3, wherein repositioning the skin along the incision to expose at least the portion of the second bone and guiding the cutting instrument along the second side guide surface of the bone cutting guide to cut the second bone comprises retracting the skin along the incision to expose at least the portion of the second bone and guiding the cutting instrument along the second side guide surface of the bone cutting guide to cut the second bone while the first bone remains at least partially covered with the skin.

15. The minimally invasive technique of claim 3, further comprising:

adjusting a separation distance between the first bone and the second bone; and fixating a moved position of the first bone and the second bone using one or more bone connectors.

16. The minimally invasive technique of claim 15, wherein the adjusting of the separation distance between the first bone and the second bone comprises correcting an alignment of the first bone in relation to the second bone in at least one plane.

17. The minimally invasive technique of claim 3, further comprising, prior to making the incision, positioning an incision guide over a joint locator pin, wherein the incision guide defines a length of the incision, and making the incision via the incision guide.

* * * * *